(12) United States Patent
Liu et al.

(10) Patent No.: US 8,470,784 B2
(45) Date of Patent: Jun. 25, 2013

(54) METHODS AND COMPOSITIONS FOR PREVENTING OR TREATING OPHTHALMIC CONDITIONS

(75) Inventors: Liping Liu, Manassas, VA (US); Shibo Tang, Guangzhou (CN); Xiaoling Liang, Guangzhou (CN)

(73) Assignee: Stealth Peptides International, Inc. (MC)

( * ) Notice: Subject to any disclaimer, the term of this patent is extended or adjusted under 35 U.S.C. 154(b) by 0 days.

(21) Appl. No.: 12/861,593

(22) Filed: Aug. 23, 2010
(Under 37 CFR 1.47)

(65) Prior Publication Data
US 2011/0177047 A1   Jul. 21, 2011

Related U.S. Application Data

(60) Provisional application No. 61/236,440, filed on Aug. 24, 2009, provisional application No. 61/237,745, filed on Aug. 28, 2009, provisional application No. 61/348,470, filed on May 26, 2010.

(51) Int. Cl.

| A61K 38/00 | (2006.01) |
|---|---|
| A61K 38/13 | (2006.01) |
| A61K 38/06 | (2006.01) |
| A61K 38/07 | (2006.01) |
| A61P 9/10 | (2006.01) |
| A61P 27/02 | (2006.01) |

(52) U.S. Cl.
USPC .................. 514/20.8; 514/20.5; 514/21.9

(58) Field of Classification Search
None
See application file for complete search history.

(56) References Cited

U.S. PATENT DOCUMENTS

| 4,522,811 | A | 6/1985 | Eppstein et al. |
|---|---|---|---|
| 5,312,899 | A | 5/1994 | Schiller |
| 5,602,100 | A | 2/1997 | Brown et al. |
| 5,652,122 | A | 7/1997 | Frankel et al. |
| 5,674,534 | A | 10/1997 | Zale et al. |
| 5,716,644 | A | 2/1998 | Zale et al. |
| 5,885,958 | A | 3/1999 | Zadina et al. |
| 5,993,848 | A | 11/1999 | Suzuki et al. |
| 5,994,372 | A | 11/1999 | Yaksh |
| 6,221,355 | B1 | 4/2001 | Dowdy |
| 6,268,398 | B1 | 7/2001 | Ghosh et al. |
| 6,468,798 | B1 | 10/2002 | Debs et al. |
| 6,503,713 | B1 | 1/2003 | Rana |
| 6,703,483 | B1 | 3/2004 | Schiller |
| 6,759,520 | B1 | 7/2004 | Carr et al. |
| 6,900,178 | B2 | 5/2005 | Oeltgen et al. |
| 7,498,297 | B2 | 3/2009 | Szeto et al. |
| 7,541,340 | B2 | 6/2009 | Szeto et al. |
| 7,550,439 | B2 | 6/2009 | Szeto |
| 7,576,061 | B2 | 8/2009 | Szeto et al. |
| 7,704,954 | B2 | 4/2010 | Szeto et al. |
| 7,718,620 | B2 | 5/2010 | Szeto et al. |
| 7,732,398 | B2 | 6/2010 | Szeto et al. |
| 7,781,405 | B2 | 8/2010 | Szeto |
| 7,811,987 | B2 | 10/2010 | Szeto et al. |
| 8,143,219 | B2 * | 3/2012 | Szeto et al. .................. 514/15.4 |
| 2005/0096333 | A1 | 5/2005 | Dugar et al. |
| 2005/0192215 | A1 | 9/2005 | Ghosh et al. |
| 2007/0015711 | A1 * | 1/2007 | Szeto .............................. 514/13 |
| 2007/0093969 | A1 | 4/2007 | Mendrick et al. |
| 2007/0259377 | A1 | 11/2007 | Urdea et al. |
| 2008/0014604 | A1 | 1/2008 | Devarajan et al. |
| 2008/0027082 | A1 | 1/2008 | Hocher et al. |
| 2009/0221514 | A1 | 9/2009 | Szeto et al. |
| 2009/0253641 | A1 | 10/2009 | Neufer et al. |

FOREIGN PATENT DOCUMENTS

| WO | WO-96/40073 | 12/1996 |
|---|---|---|
| WO | WO-99/15154 | 4/1999 |
| WO | WO-00/38651 | 7/2000 |
| WO | WO-2007/035640 | 3/2007 |
| WO | WO-2009/100363 | 8/2009 |
| WO | WO-2009/108695 | 9/2009 |
| WO | WO-2010/120431 | 10/2010 |
| WO | WO-2011/019809 | 2/2011 |
| WO | WO-2011/091357 A1 | 7/2011 |
| WO | WO-2011/139992 A1 | 11/2011 |
| WO | WO-2012/174117 A2 | 12/2012 |

OTHER PUBLICATIONS

Yildirim et al. Antioxidant Enzymes and Diabetic Retinopathy. Ann. N. Y. Acad. Sci. 2007, vol. 1100, pp. 199-206.*
Anderson et al.; "Mitochondrial production of reactive oxygen species contributes to the β adrenergic stimulation of mouse cardiomyocytes"; J. Physiol. (2011); vol. 589(7); pp. 1791-1801.
Calkins et al.; "Impaired mitochondrial biogenesis, defective axonal transport of mitochondria, abnormal mitochondrial dynamics and synaptic degeneration in a mouse model of Alzheimer's disease"; Hum. Mol. Genet. (2011); vol. 20(23); pp. 4515-4529.
Cao et al.; "Mitochondria-targeted antioxidant attenuates high glucose-induced P38 MAPK pathway activation in human neuroblastoma cells"; Mol. Med. Report. (2012); vol. 5(4); pp. 929-934.
Carter et al.; "Evaluation of the antioxidant peptide SS31 for treatment of burn-induced insulin resistance"; Int. J. Mol. Med. (2011); vol. 28(4); pp. 589-594.
Chen et al.; "Mitochondria-targeted peptide MTP-131 alleviates mitochondrial dysfunction and oxidative damage in human trabecular meshwork cells"; Invest. Ophthalmol. Vis. Sci. (2011); vol. 52(10); pp. 7027-7037.
Dai et al.; "Mitochondrial targeted antioxidant peptide ameliorates hypertensive cardiomyopathy"; J. Am. Coll. Cardiol. (2011); vol. 58(1); pp. 73-82.
Eirin et al.; "A mitochondrial permeability transition pore inhibitor improves renal outcomes after revascularization in experimental atherosclerotic renal artery stenosis" J. Am. Heart Assoc. (2012) (manuscript) 35 pages.

(Continued)

*Primary Examiner* — Marcela M Cordero Garcia
(74) *Attorney, Agent, or Firm* — Foley & Lardner LLP

(57) ABSTRACT

The disclosure generally describes methods of preventing or treating ophthalmic diseases or conditions in a mammalian subject, such as diabetic retinopathy, cataracts, retinitis pigmentosa, glaucoma, macular degeneration, choroidal neovascularization, retinal degeneration, and oxygen-induced retinopathy. The methods comprise administering an effective amount of an aromatic-cationic peptide to subjects in need thereof.

6 Claims, 46 Drawing Sheets

OTHER PUBLICATIONS

Gilliam et al.; "Doxorubicin acts via mitochondrial ROS to stimulate catabolism in C2C12 Myotubes"; Am. J. Physiol. Cell Physiol. (2012); vol. 302(1); pp. C195-C202.

Kloner et al.; "Reduction of ischemia/reperfusion injury With Bendavia, a mitochondria-targeting cytoprotective peptide"; J. Am. Heart Assoc. (2012) (proof) 15 pages.

Lee et al.; "Novel mitochondria-targeted antioxidant peptide ameliorates burn-induced apoptosis and endoplasmic reticulum stress in the skeletal muscle of mice"; Shock (2011); vol. 36(6); pp. 580-585.

Li et al.; "Mitochondria-targeted antioxidant peptide SS31 attenuates high glucose-induced injury on human retinal endothelial cells"; Biochem. Biophys. Res. Commun. (2011); vol. 404(1); pp. 349-356.

Ma et al.; "Superoxide flashes: early mitochondrial signals for oxidative stress-induced apoptosis"; J. Biol. Chem. (2011); vol. 286(31); pp. 27573-27581.

Manczak et al.; "Mitochondria-targeted antioxidants protect against amyloid-β toxicity in Alzheimer's Disease neurons"; J. Alzheimer's Dis. (2010); vol. 20(2); pp. S609-S631.

Min et al.; "Mitochondrial-targeted antioxidants protect skeletal muscle against immobilization-induced muscle atrophy"; J. Appl. Physiol. (2011); vol. 111(5); pp. 1459-1466.

Nieborowska-Skorska et al.; "Rac2-MRC-cIII-generated ROS cause genomic instability in chronic myeloid leukemia stem cells and primitive progenitors"; Blood (2012); vol. 119(18); pp. 4253-4263.

Petri et al.; "Cell-permeable peptide antioxidants as a novel therapeutic approach in a mouse model of amyotrophic lateral sclerosis"; J. Neurochem. (2006); vol. 98(4); pp. 1141-1148.

Powers et al.; "Mitochondria-targeted antioxidants protect against mechanical-ventilation-induced diaphragm weakness"; Crit. Care Med. (2011); vol. 39(7); pp. 1749-1759.

Reddy et al.; "Toxicity of neurons treated with herbicides and neuroprotection by mitochondria-targeted antioxidant SS31"; Int. J. Environ. Res. Public Health. (2011); vol. 8(1); pp. 203-221.

Sharma et al.; "Mitochondrial respiratory complex I dysfunction promotes tumorigenesis through ROS alteration and AKT activation"; Hum. Mol. Genet. (2011); vol. 20(23); pp. 4605-4616.

Sloan et al.; "Mitochondrial permeability transition in the diabetic heart: Contributions of thiol redox state and mitochondrial calcium to augmented reperfusion injury"; J. Mol. Cell. Cardiol. (2012); vol. 52(5); pp. 1009-1018.

Szeto et al.; "Mitochondria-targeted peptide accelerates ATP recovery and reduces ischemic kidney injury"; J. Am. Soc. Nephrol. (2011); vol. 22(6); pp. 1041-1052.

Szeto, H. & Schiller, P.; "Novel therapies targeting inner mitochondrial membrane—from discovery to clinical development"; Pharm. Res. (2011); vol. 28(11); pp. 2669-2679.

Wang et al.; "Elevated mitochondrial reactive oxygen species generation affects the immune response via hypoxia-inducible factor-1 α in long-lived Mclk1+/− mouse mutants"; J. Immunol. (2010); vol. 184(2); pp. 582-590.

Whiteman et al.; "Do mitochondriotropic antioxidants prevent chlorinative stress-induced mitochondrial and cellular injury?"; Antioxid. Redox Signal. (2008); vol. 10(3); pp. 641-650.

Zhu et al.; "Histone deacetylase-3 activation promotes tumor necrosis factor-alpha (TNF-α) expression in cardiomyocytes during lipopolysaccharide stimulation"; J. Biol. Chem. (2010); vol. 285(13); pp. 9429-9436.

Zhu et al.; "MicroRNA-195 promotes palmitate-induced apoptosis in cardiomyocytes by down-regulating Sirt1"; Cardiovasc. Res. (2011); vol. 92(1); pp. 75-84.

"A randomized, placebo-controlled, clinical trial of high-dose supplementation with vitamins C and E, beta carotene, and zinc for age-related macular degeneration and vision loss: AREDS report No. 8"; Age-Related Eye Disease Study Research Group; Arch. Ophthalmol. (Oct. 2001), vol. 119(10), pp. 1417-1436.

Aitman, et al.; "Identification of CD36 (Fat) as an insulin resistance gene causing defective fatty acid and glucose metabolism in hypertensive rats"; Nature Genetics (Jan. 1999); vol. 21(1), pp. 76-83.

Allikmets, et al.; "Mutation of the Stargardt Disease Gene (ABCR) in Age-Related Macular Degeneration"; Science (Sep. 19, 2007); vol. 277, pp. 1805-1807.

Allikmets, Rando; "Simple and Complex ABCR: Genetic Predisposition to Retinal Disease"; Am. J Hum. Genet. (2000); vol. 67, pp. 793-799.

Anderson, et al.; "Mitochondrial H2O2 emission and cellular redox state link excess fat intake to insulin resistance in both rodents and humans"; J. Clin. Invest. (Mar. 2009); vol. 119(3), pp. 573-581.

Beauchamp, et al.; "Role of thromboxane in retinal microvascular degeneration in oxygen-induced retinopathy"; J. Appl. Physiol. (2001); vol. 90: pp. 2279-2288.

Cho, et al.; "A novel cell-permeable antioxidant peptide, SS31, attenuates ischemic brain injury by down-regulating CD36"; J. Biol. Chem. (2007); vol. 282(7), pp. 4634-4642.

Cho, et al.; "Potent mitochondria-targeted peptides reduce myocardial infarction in rats"; Coron Artery Dis. (May 2007); vol. 18(3), pp. 215-220.

Corpeleijn, et al.; "Direct association of a promoter polymorphism in the CD36/FAT fatty acid transporter gene with Type 2 diabetes mellitus and insulin resistance"; Diabet Med. (2006); vol. 23(8), pp. 907-911.

Drin, et al.; "Studies on the Internalization Mechanism of Cationic Cell-penetrating Peptides"; Journal of Biological Chemistry (2003); vol. 278(33), pp. 31192-31201.

Dunn, et al.; "ARPE-19, A human Retinal Pigment Epithelial Cell Line with Differentiated Properties"; Experimental Eye Research(1995); vol. 62, pp. 155-169.

Fuhrman, et al.; "Oxidative stress increases the expression of the CD36 scavenger receptor and the cellular uptake of oxidized low-density lipoprotein in macrophages from atherosclerotic mice: protective role of antioxidants and of paraoxonase"; Atherosclerosis (2002); vol. 161(2), pp. 307-316.

Han, et al.; "Mitochondria-Derived Reactive Oxygen Species Mediate HemeOxygenase-1 Expression in Sheared Endothelial Cells"; J. Pharmacol. and Exp. Therapeutics (Apr. 2009); vol. 329(1), pp. 94-101.

Heckenlively, et al.; "Clinical Findings and Common Symptoms in Retinitis Pigmentosa," AM. J. Ophthalmol. (May 1988); vol. 105, pp. 504-511.

Ignarro, et al.; "Endothelium-derived relaxing factor produced and released from artery vein is nitric oxide"; Proc. Natl. Acad. Sci. USA, (Dec. 1987); vol. 84, pp. 9265-9269.

International Search Report & Written Opinion; PCT International Patent Application No. PCT/US2010/046338; Applicant: Stealth Peptides International, Inc.; Mailed: Oct. 8, 2010.

Klevering, et al.; "Three Families Displaying the Combination of Stargardt's Disease with Cone-Rod Dystrophy or Retinitis Pigmentosa"; Ophthalmology (Mar. 2004); vol. 111(3), pp. 546-553.

Lewis, et al.; "Genotype/Phenotype Analysis of a Photoreceptor-Specific ATP-Binding Cassette Transporter Gene, ABCR, in Stargardt Disease"; Am. J. Hum. Genet. (1999); vol. 64, pp. 422-434.

Mizuguchi, et al.; "A novel cell-permeable antioxidant peptide decreases renal tubular apoptosis and damage in unilateral ureteral obstruction"; Am. J. Physiol. Renal Physiol.(epublished Sep. 10, 2008); vol. 295(5), pp. F1545-F1553.

Moosmann, et al.; "Secretory Peptide Hormones Are Biochemical Antioxidants: Structure-Activity Relationship"; Mol. Pharmacol. (2002); vol. 61(2), pp. 260-268.

Palmer, et al.; "Nitric oxide release accounts for the biological activity of endothelium-derived relaxing factor"; Nature (Jun. 11, 1987); vol. 327, pp. 524-526.

Richard, et al.; "Cell-penetrating Peptides"; Journal of Biological Chemistry (Jan. 2003); vol. 278(1), pp. 585-590.

Shaban, et al.; "A2E and Blue Light in the Retina: The Paradigm of Age-Related Macular Degeneration"; Biol. Chem. (Mar./Apr. 2002); vol. 383, pp. 537-545.

Sparrow, et al.; "A2E-epoxides Damage DNA in Retinal Pigment Epithelial Cells"; J. Biol. Chem. (May 2003); vol. 278(20), pp. 18207-18213.

Stone, et al.; "Allelic variation in ABCR associated with Stargardt disease but not age-related macular degeneration"; Nature Genetics (Dec. 1998); vol. 20, pp. 328-329.

Szeto, et al.; "In Vivo Disposition of Dermorphin Analog (DALDA) in Nonpregnant and Pregnant Sheep"; The Journal of Pharmacology and Experimental Therapeutics (1998); vol. 284(1), pp. 61-65.

Szeto, et al.; "In vivo Pharmacokinetics of Selective μ-Opioid Pptide Agonists"; The Journal of Pharmacology and Experimental Therapeutics (Jul. 2001); vol. 298(1), pp. 57-61.

Szeto, et al.; "Respiratory depression after intravenous administration of δ-Selective opioid peptide analogs"; Peptides (1999); vol. 20, pp. 101-105.

Szeto, Hazel H.; "Cell-permeable, Mitochondrial-targeted, Peptide Antioxidants"; The AAPS Journal (2006); vol. 8(2), Article 32, pp. E277-E283.

Szeto, Hazel H.; "Development of Mitochondria-targeted Aromatic-cationic Peptides for Neurodegenerative Diseases"; Annals of the New York Academy of Sciences (2008); vol. 1147, pp. 112-121.

Szeto, Hazel H.; "Mitochondria-Targeted Peptide Antioxidants: Novel Neuroprotective Agents"; The AAPS Journal (2006); vol. 8(3), Article 62, pp. E521-E531.

Szeto, Hazel H.; "Mitochondria-Targeted Cytoprotective Peptides for Ischemia-Reperfusion Injury"; Antioxidants & Redox Signaling (Nov. 2008); vol. 10(3), pp. 601-619.

Thomas, et al.; "Mitochondrial Targeting with Antioxidant Peptide SS-31 Prevents Mitochondrial Depolarization, Reduces Islet Cell Apoptosis, Increases Islet Cell Yield, and Improves Posttransplantation Function"; J. Am. Soc. Nephrol. (2007); vol. 18, pp. 213-222.

Tuohy, et al.; "Sensitivity of Photoreceptor-Derived Cell Line (661 W) to Baculoviral p 35, Z-VAD.FMK, and Fas-Associated Death Domain"; Investigative Ophthalmology and Visual Science (Nov. 2002); vol. 43(11), pp. 3583-3589.

Unger, et al.; "Hyperglycaemia as an inducer as well as a consequence of impaired islet cell function and insulin resistance: implications for the management of diabetes"; Diabetologia (1985); vol. 28, pp. 119-121.

Wells, James A.; "Additivity of Mutational Effects in Proteins"; Biochemistry, American Chemical Society (Sep. 18, 1990); vol. 29(37), pp. 8509-8517.

Whittaker, et al.; "Design and Therapeutic Application of Matrix Metalloproteinase Inhibitors"; Chemical Reviews (1999); vol. 99(9), pp. 2735-2776.

Wu, et al.; "A highly potent peptide analgesic that protects against ischemia-reperfusion-induced myocardial stunning"; Am. J. Physioll Heart Circ. Physiol. (2002); vol. 283, pp. H783-H791.

Yang, et al.; "Mitochondria Targeted Peptides Protect against 1-Methyl-4-Phenyl-1, 2, 3, 6-Tetrahydropyridine Neurotoxicity"; Antioxidant & Redox Signaling (2009); vol. 11(8), (epublished ahead of print).

Zhao et al., Mitochondrial-targeted peptide prevents mitochondrial depolarization and apoptosis induced by tert-butyl hydroperoxide in neuronal cell lines, Biochem Pharmacol., 70(12):1796-1806, Oct. 10, 2005 (epublished).

Zhao, et al.; "Cell-permeable Peptide Antioxidants Targeted to Inner Mitochondrial Membrane Inhibit Mitochondrial Swelling, Oxidative Cell Death, and Reperfusion Injury"; J. Biol. Chem. (Aug. 2004); vol. 279(33). pp. 34682-34690.

Zhao, et al.; "Transcellular Transport of a Highly Polar 3+ Net Charge Opioid Tetrapeptide"; Journal of Pharmacology and Experimental Therapeutics (2003); vol. 304(1), pp. 425-432.

Alam, N.M. et al., "A Novel Peptide (MTP-131) that Improves Mitochondrial Function Reverses Visual Decline in Mouse Models of Metabolic Dysfunction Leading to Diabetes," American Diabetes Association, (2012), Poster Presentation (1 page).

Alam, N.M. et al., "Reducing Mitochondrial Oxidative Stress to Treat Diabetes and Age-related Visual Decline," Society of Neuroscience, (2011), Poster Presentation (1 page).

Alam, Nazia et al., "A novel Peptide that Improves Mitochondrial Function Reverses Diabetes- and Age-Related Visual Decline," American Aging Association, (2012), Abstract (1 page).

Brown, David A. et al., "Bendavia, a mitochondria-targeting peptide, reduces reperfusion injury and reactive oxygen species levels through a mechanism independent of direct oxygen radical scavenging: A multicenter study," American Heart Association, (2012), Abstract (1 page).

Brown, David A., Ph.D., "Mitochondrial Derived Cardioprotection in Exercised Hearts: Role of Cardiac Glutathione," American College of Sports Medicine, (2012), DB Lab Presentation (28 pages).

Chonn, Arcadio et al., "Recent Advances in Liposomal Drug-Delivery Systems," Current Opinion in Biotechnology, (1995), vol. 6, pp. 698-708.

Eirin, Alfonso et. al., "Chronic Treatment with Bendavia Preserves the Stenotic Kidney in Swine Atherosclerotic Renovascular Disease (ARVD)," American Society of Nephrology, (2012), Abstract & figures (2 pages).

Eirin, Alfonso et. al., "Mitochondrial Targeted Peptides Attenuate Myocardial Damage after Renal Revascularization in Experimental Atherosclerotic Renovascular Hypertension," American Society of Nephrology, (2012), Abstract & figures (2 pages).

Eirin, Alfonso, et. al., "MTP-131 reduces renal injury after percutaneous transluminal renal angioplasty (PTRA) in swine atherosclerotic renal artery stenosis (ARAS)," American Society of Nephrology, (2011), Poster Presentation (1 page).

Gregoriadis, Gregory, "Engineering Liposomes for Drug Delivery: Progress and Problems," TIBTECH, (Dec. 1995), vol. 13, pp. 527-537.

Hale, Sharon L. et. al., "A Novel Mitochondrial Permeability Transition Pore Inhibitor, Bendavia, Reduces, Microvascular Obstruction (No-Reflow) due to Myocardial Ischemia/Reperfusion Injury in the Rabbit," Basic Cardiovascular Sciences, (2011), Poster Presentation (1 page).

International Preliminary Report on Patentability received for PCT/US2010/046338 dated Mar. 8, 2012 (5 pages).

Kloner, Robert A., et. al., "Bendavia, a Novel Mitochondrial-Targeted Cytoprotective Compound Reduces Ischemia/Reperfusion Injury: Experience in 3 Independent Laboratories," American Heart Association, (2011), Abstract (2 pages).

Liang, XL., et. al., "SS31 protects human RPE cells from oxidative damage and reduces laser-induced choroidal neovascularization," Association for Research in Vision and Opthamology, (2010), Poster Presentation (1 page).

Lichtenberg, Dov et al., "Liposomes: Preparation, Characterization and Preservation," Methods of Biochemical Analysis, (1988), vol. 33, pp. 337-462.

Liu, Shaoyi et. al., "Boosting mitochondrial function to minimize ischemia-reperfusion injury," Experimental Biology, (2011), Poster Presentation (1 page).

Liu, Shaoyi et. al., "Mitochondria-targeting peptide (SS-31) promotes rapid repair of actin cytoskeleton following ischemia and protects tubular epithelial cell architecture," American Society of Nephrology, (2012), Abstract (2), (1 page).

Marcinek, David J., et al., "Acute pharmacological intervention reverses mitochondrial deficits and improves function in aged skeletal muscle," American Aging Association, (2012), Abstract (1 page).

Min, Kisuk et. al., "Mitochondrial-targeted antioxidants attenuate immobilization-induced skeletal muscle atrophy," Experimental Biology, (2011), Abstract (1 page).

Mizuguchi, Hiroyuki et al., "Intratumor administration of fusogenic liposomes containing fragment A of diphtheria toxin suppresses tumor growth," Cancer Lett., (1996), vol. 100, Issue 1, pp. 63-69.

Putney, Scott D., "Encapsulation of proteins for improved delivery," Current Opinion in Chemical Biology, (1998), vol. 2, No. 4, pp. 548-552.

Rabinovitch, Peter, "Mitochondrial Oxidative Stress and Cardiac Aging," Basic Cardiovascular Sciences, (2011), Presentation (19 pages).

Reddy, P. Hemachandra, "Amyloid beta Toxicity, Mitochondrial Dysfunction and Synaptic Damage in Alzheimer's Disease: Implications for Mitochondria-Targeted Antioxidant Therapeutics," New York Academy of Sciences, (2010), Abstract (1 page).

Sabbah, Hani N. et al., "Acute Intravenous Infusion of Bendavia (MTP-131), A Novel Mitochondria-Targeting Peptide, Improves Left Ventricular Systolic Function in Dogs With Advanced Heart Failure," American Heart Association, (2012), Abstract (1 page).

Schiller, Peter W. et al., "Synthesis and in Vitro Opioid Activity Profiles of DALDA Analogues," European Journal of Medicinal Chemistry, (Oct. 2000), vol. 35, Issue 10, pp. 895-901.

Szeto, Hazel H. et. al., "Mitochondria-targeting peptide (SS-31, Bendavia®) prevents microvascular rarafaction, inflammation, and fibrosis caused by ischemia-reperfusion injury," American Society of Nephrology, (2012), Abstract (1 page).

Szeto, Hazel H., "Mitochondrial Protection as Strategy to treat Ischemia-Reperfusion Injury," American Society of Nephrology, (2010), Presentation (17 pages).

Szeto, Hazel H., "The development of a therapeutic peptide for mitochondrial protection—from bench to bedside," Experimental Biology, (2011), Poster Presentation (1 page).

Szeto, Hazel H., et. al., "Rapid Restoration of ATP by SS-31, an Inhibitor of Mitochondrial Permeability Transition, Prevents Tubular Cytoskeletal Rearrangement in Renal Ischemia-Reperfusion Injury," American Society of Nephrology, (2010), Poster Presentation (1 page).

Tiganis, Tony, "Reactive Oxygen Species & NAPDH Oxidases in Insulin Signalling," NOX Gordon Research Conference, (Jun. 3-8, 2012), Presentation (44 pages).

Weiner, Alan L., "Liposomes for Protein Delivery: Selecting Manufacture and Development Processes," Immunomethods, (1994), vol. 4., pp. 201-209.

Brennan, Lisa A. et al., "Mitochondrial function and redox control in the aging eye: Role of MsrA and other repair systems in cataract and macular degenerations," Experimental Eye Research, vol. 88, No. 2, (Feb. 2, 2009), pp. 195-203.

Chaturvedi, Rajnish K. et al., "Mitochondrial Approaches for Neuroprotection," Annals of the New York Academy of Sciences, vol. 1147, (Dec. 2008), pp. 395-412.

Extended Search Report issued in European Patent Application No. 10812524.6 dated Mar. 14, 2013 (12 pages).

Jarrett, Stuart G. et al., "Mitochondrial DNA damage and its potential role in retinal degeneration," Progress in Retinal and Eye Research, Oxford, GB., vol. 27, No. 6, (Nov. 1, 2008), pp. 596-607.

Yousif, Lema F. et al., "Targeting Mitochondria with Organelle-Specific Compounds: Strategies and Applications," Chembiochem—A European Journal of Chemical Biology, Wile Weinheim, DE, vol. 10, No. 12, (Aug. 17, 2009), pp. 1939-1950.

\* cited by examiner

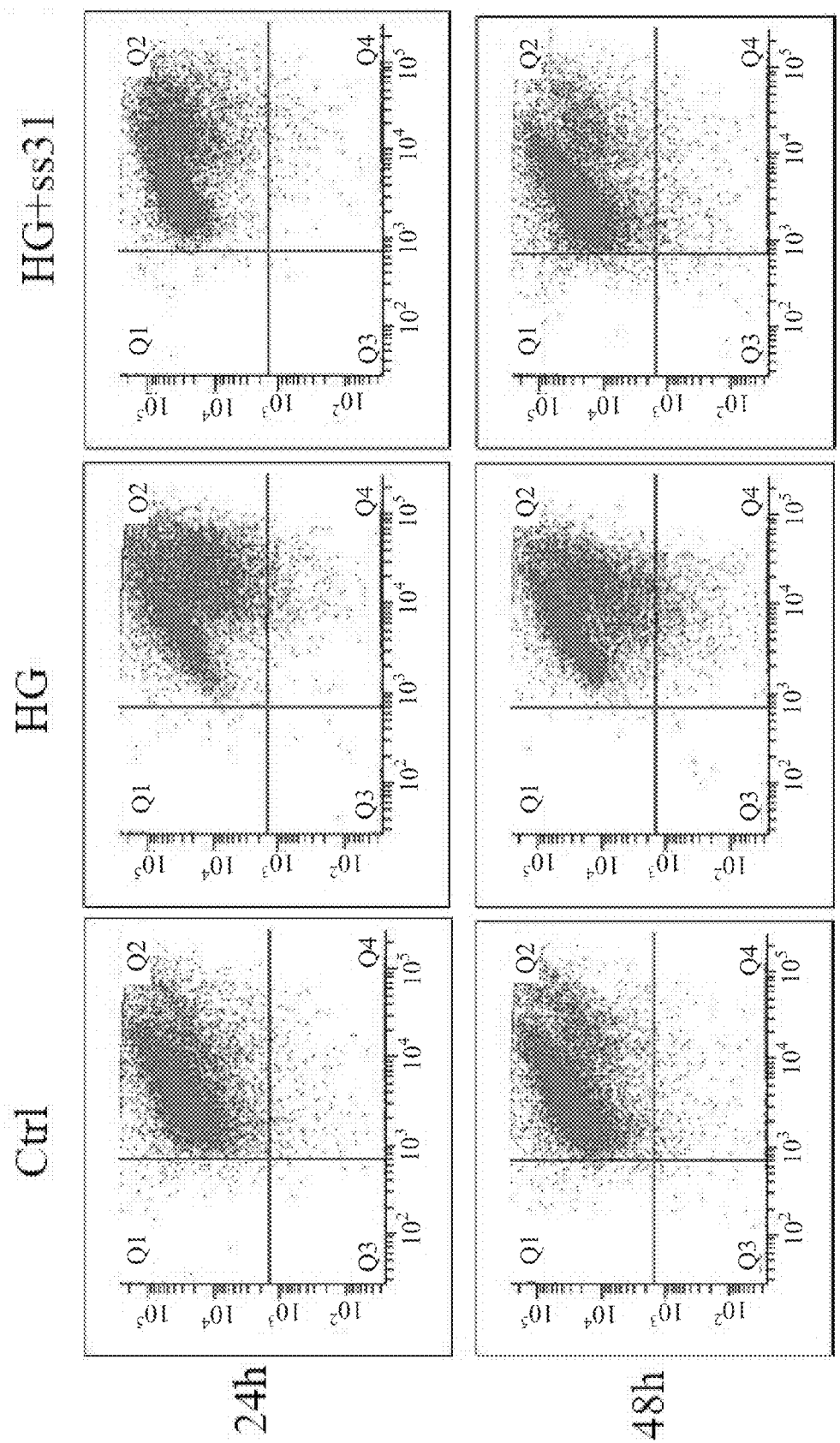

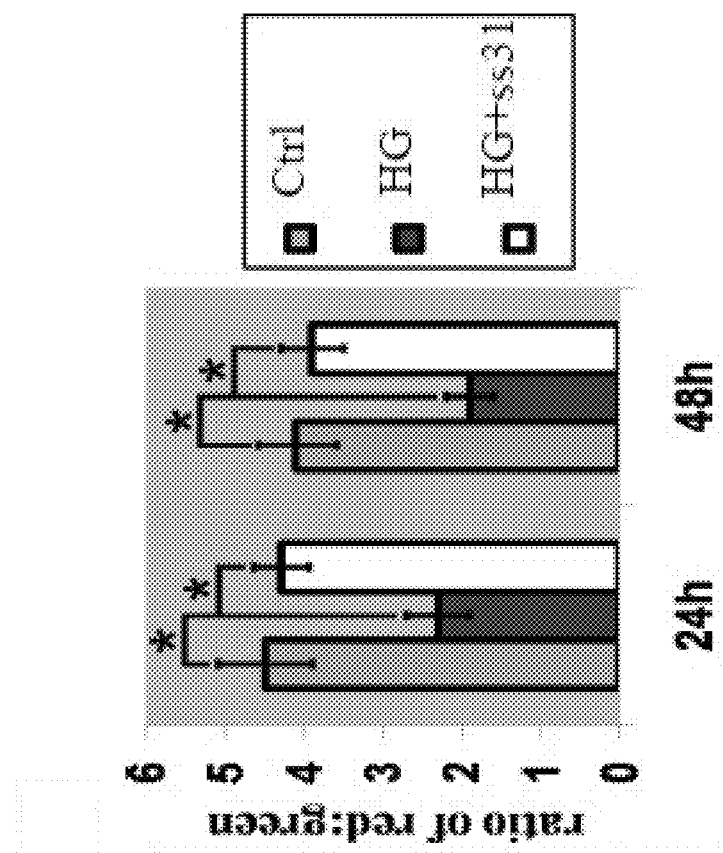

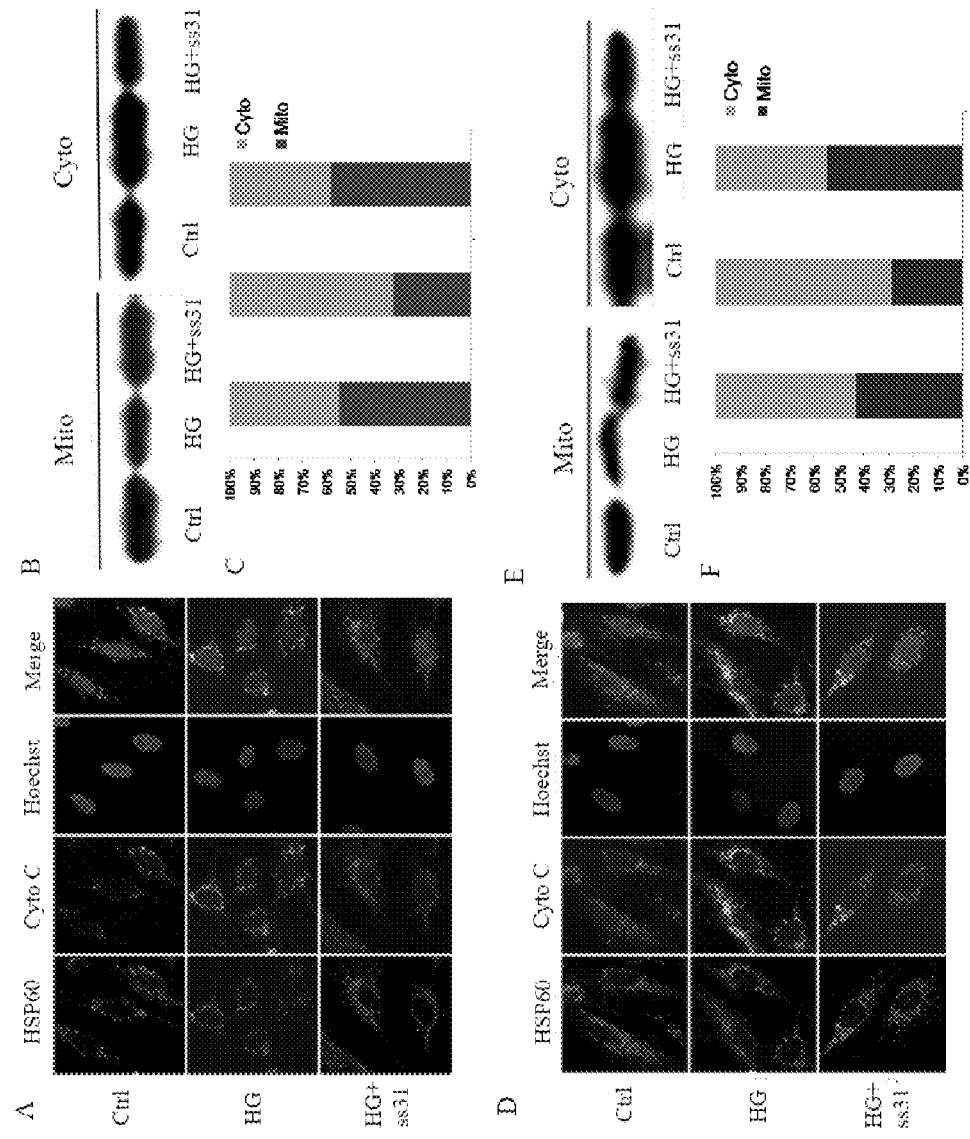

A: STZ rat model;
B: HFD/STZ rat model

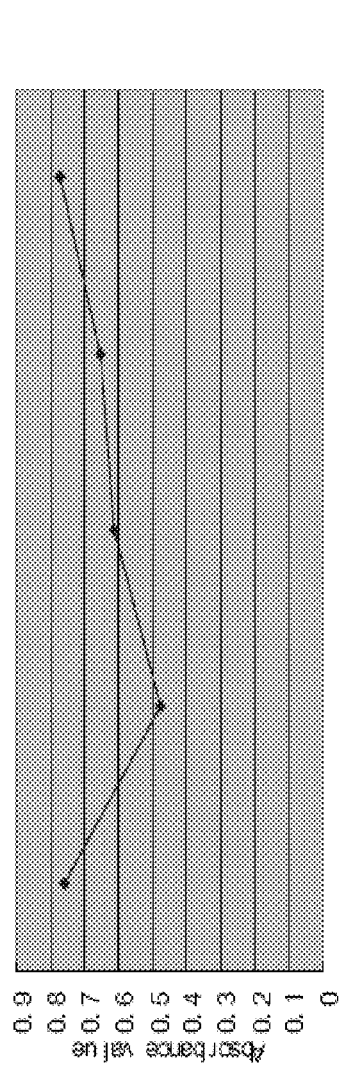
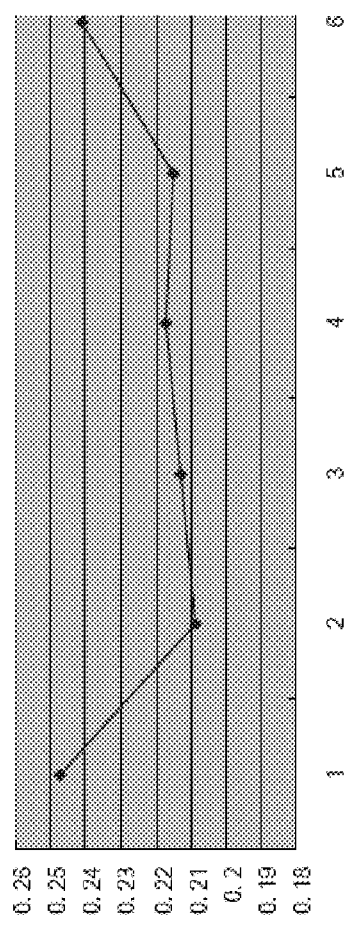
FIG. 27A
FIG. 27B

FIG. 40
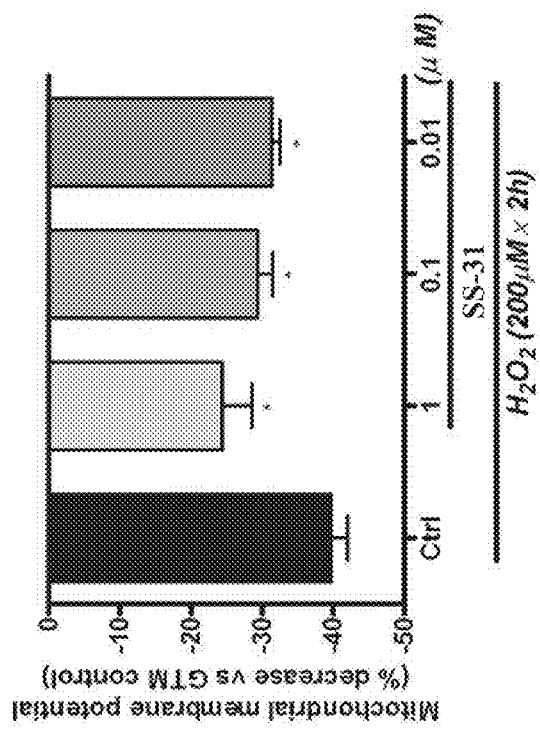
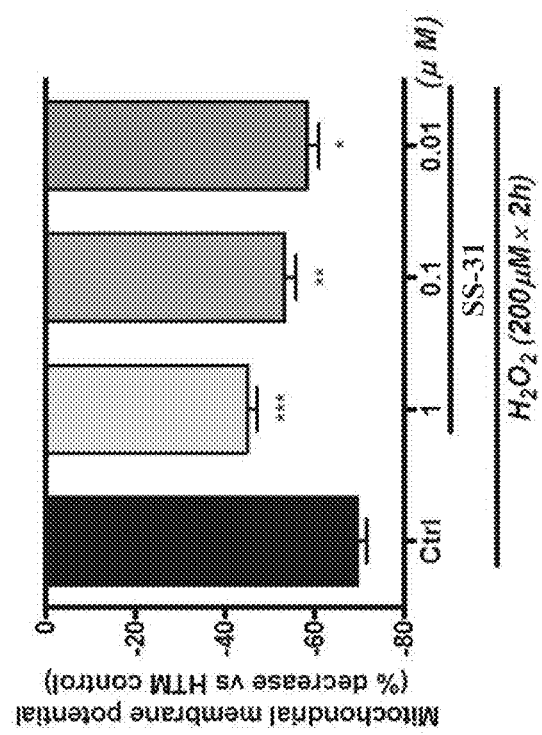

METHODS AND COMPOSITIONS FOR PREVENTING OR TREATING OPHTHALMIC CONDITIONS

CROSS-REFERENCE TO RELATED APPLICATIONS

This application claims priority to U.S. Provisional Application No. 61/236,440, filed Aug. 24, 2009; U.S. Provisional Application No. 61/237,745, filed Aug. 28, 2009; and U.S. Provisional Application No. 61/348,470, filed May 26, 2010. The entire contents of these applications is hereby incorporated by reference in their entirety.

TECHNICAL FIELD

The present technology relates generally to compositions and methods of preventing or treating ophthalmic diseases or conditions. In particular, the present technology relates to administering aromatic-cationic peptides in effective amounts to prevent or treat ophthalmic diseases or conditions, e.g., diabetic retinopathy, cataracts, retinitis pigmentosa, glaucoma, choroidal neovascularization, and oxygen-induced retinopathy, in mammalian subjects.

BACKGROUND

The following description is provided to assist the understanding of the reader. None of the information provided or references cited is admitted to be prior art to the present invention.

Diseases and degenerative conditions of the optic nerve and retina are the leading causes of blindness in the world. A significant degenerative condition of the retina is age-related macular degeneration (ARMD). ARMD is the most common cause of blindness in people over 50 in the USA and its prevalence increases with age. ARMD is classified as either wet (neovascular) or dry (non-neovascular); the dry form of the disease is more common. Macular degeneration occurs when the central retina has become distorted and thinned usually associated with age but also characterized by intraocular inflammation and angiogenesis (wet ARMD only) and/or intra-ocular infection. The subsequent generation of free radicals, resulting in oxidative tissue damage, local inflammation and production of growth factors (such as VEGF and FGF) and inflammatory mediators, leads to inappropriate neovascularisation in common with the wet form of ARMD.

Retinopathy is a leading cause of blindness in type I diabetes, and is also common in type II diabetes. The degree of retinopathy depends on the duration of diabetes, and generally begins to occur ten or more years after onset of diabetes. Diabetic retinopathy may be classified as non-proliferative, where the retinopathy is characterized by increased capillary permeability, edema and exudates, or proliferative, where the retinopathy is characterized by neovascularisation extending from the retina to the vitreous, scarring, deposit of fibrous tissue and the potential for retinal detachment. Diabetic retinopathy is believed to be caused by the development of glycosylated proteins due to high blood glucose. Several other less common retinopathies include choroidal neovascular membrane (CNVM), cystoid macular edema (CME), epiretinal membrane (ERM) and macular hole.

Glaucoma is made up of a collection of eye diseases that cause vision loss by damage to the optic nerve. Elevated intraocular pressure (IOP) due to inadequate ocular drainage is the primary cause of glaucoma. Glaucoma often develops as the eye ages, or it can occur as the result of an eye injury, inflammation, tumor or in advanced cases of cataract or diabetes. It can also be caused by the increase in IOP caused by treatment with steroids. Drug therapies that are proven to be effective in glaucoma reduce IOP either by decreasing vitreous humor production or by facilitating ocular draining. Such agents are often vasodilators and as such act on the sympathetic nervous system and include adrenergic antagonists.

SUMMARY

The present technology relates generally to the treatment or prevention of ophthalmic diseases or conditions in mammals through administration of therapeutically effective amounts of aromatic-cationic peptides to subjects in need thereof.

In one aspect, the present disclosure provides a method of treating or preventing an ophthalmic condition in a mammalian subject in need thereof, the method comprising administering to the subject a therapeutically effective amount of the peptide D-Arg-2'6'-Dmt-Lys-Phe-NH$_2$ or Phe-D-Arg-Phe-Lys-NH$_2$. In one embodiment, the ophthalmic condition is selected from the group consisting of: diabetic retinopathy, cataracts, retinitis pigmentosa, glaucoma, macular degeneration, choroidal neovascularization, retinal degeneration, and oxygen-induced retinopathy.

In one aspect, the disclosure provides a method of treating or preventing ophthalmic conditions in a mammalian subject, comprising administering to said mammalian subject a therapeutically effective amount of an aromatic-cationic peptide. In some embodiments, the aromatic-cationic peptide is a peptide having:

at least one net positive charge;

a minimum of four amino acids;

a maximum of about twenty amino acids;

a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein 2a is the largest number that is less than or equal to $p_t$+1, except that when a is 1, $p_t$ may also be 1. In particular embodiments, the mammalian subject is a human.

In one embodiment, $2p_m$ is the largest number that is less than or equal to r+1, and may be equal to $p_t$. The aromatic-cationic peptide may be a water-soluble peptide having a minimum of two or a minimum of three positive charges.

In one embodiment, the peptide comprises one or more non-naturally occurring amino acids, for example, one or more D-amino acids. In some embodiments, the C-terminal carboxyl group of the amino acid at the C-terminus is amidated. In certain embodiments, the peptide has a minimum of four amino acids. The peptide may have a maximum of about 6, a maximum of about 9, or a maximum of about 12 amino acids.

In one embodiment, the peptide may have the formula Phe-D-Arg-Phe-Lys-NH$_2$ (SS-20) or 2',6'-Dmp-D-Arg-Phe-Lys-NH$_2$. In a particular embodiment, the aromatic-cationic peptide has the formula D-Arg-2',6'-Dmt-Lys-Phe-NH$_2$ (referred to interchangeably as SS-31, MTP-131, or Bendavia™).

In one embodiment, the peptide is defined by formula I:

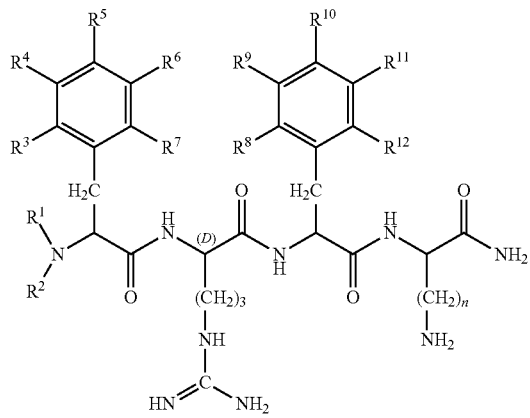

wherein $R^1$ and $R^2$ are each independently selected from
(i) hydrogen;
(ii) linear or branched $C_1$-$C_6$ alkyl;

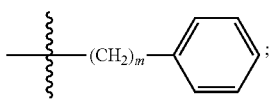 (iii)

where m = 1-3

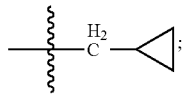 (iv)

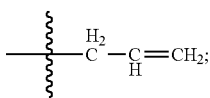 (v)

$R^3$, $R^4$, $R^5$, $R^6$, $R^7$, $R^8$, $R^9$, $R^{10}$, $R^{11}$ and $R^{12}$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo; and n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

In one embodiment, the peptide is defined by formula II:

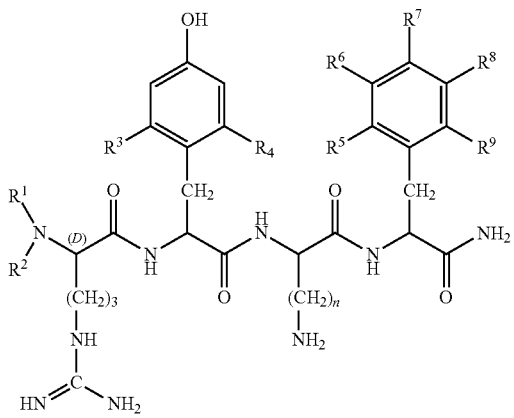

wherein $R^1$ and $R^2$ are each independently selected from
(i) hydrogen;
(ii) linear or branched $C_1$-$C_6$ alkyl;

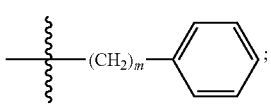 (iii)

where m = 1-3

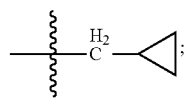 (iv)

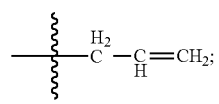 (v)

$R^3$ and $R^4$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo;
$R^5$, $R^6$, $R^7$, $R^8$, and $R^9$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo; and n is an integer from 1 to 5.

The aromatic-cationic peptides may be administered in a variety of ways. In some embodiments, the peptides may be administered intraocularly, orally, topically, intranasally, intravenously, subcutaneously, or transdermally (e.g., by iontophoresis).

In one aspect, the present disclosure provides a pharmaceutical composition comprising a therapeutically effective amount of the peptide D-Arg-2'6'-Dmt-Lys-Phe-NH$_2$ or Phe-D-Arg-Phe-Lys-NH$_2$ formulated for topical, iontophoretic, or intraocular administration.

In one aspect, the present disclosure provides an ophthalmic formulation comprising a therapeutically effective amount of the peptide D-Arg-2'6'-Dmt-Lys-Phe-NH$_2$ or Phe-D-Arg-Phe-Lys-NH$_2$. In one embodiment, the formulation is soluble in the cornea, aqueous humor, and lens of the eye. In one embodiment, the formulation further comprises a preservative. In one embodiment, the preservative is present in a concentration of less than 1%.

In one embodiment, the formulation further comprises an active agent selected from the group consisting of: an antioxidant, a metal complexer, an anti-inflammatory drug, an antibiotic, and an antihistamine. In one embodiment, the antioxidant is vitamin A, vitamin C, vitamin E, lycopene, selenium, α-lipoic acid, coenzyme Q, glutathione, or a carotenoid. In one embodiment, the formulation further comprises an active agent selected from the group consisting of: aceclidine, acetazolamide, anecortave, apraclonidine, atropine, azapentacene, azelastine, bacitracin, befunolol, betamethasone, betaxolol, bimatoprost, brimonidine, brinzolamide, carbachol, carteolol, celecoxib, chloramphenicol, chlortetracycline, ciprofloxacin, cromoglycate, cromolyn, cyclopentolate, cyclosporin, dapiprazole, demecarium, dexamethasone, diclofenac, dichlorphenamide, dipivefrin, dorzolamide, echothiophate, emedastine, epinastine, epinephrine, erythromycin, ethoxzolamide, eucatropine, fludrocortisone, fluorometholone, flurbiprofen, fomivirsen, framycetin, ganciclovir, gatifloxacin, gentamycin, homatropine, hydrocortisone, idoxuridine, indomethacin, isofluorophate, ketorolac, ketotifen, latanoprost, levobetaxolol, levobunolol, levocabastine, levofloxacin, lodoxamide, loteprednol, medrysone, methazolamide, metipranolol, moxifloxacin, naphazoline, natamycin, nedocromil, neomycin, norfloxacin, ofloxacin, olopatadine, oxymetazoline, pemirolast, pegaptanib, phenylephrine, physostigmine, pilocarpine, pindolol, pirenoxine, polymyxin B, prednisolone, proparacaine, ranibizumab, rimexolone, scopolamine, sezolamide, squalamine, sulfacetamide, suprofen, tetracaine, tetracyclin, tetrahydrozoline, tetryzoline, timolol, tobramycin, travoprost, triamcinulone, trifluoromethazolamide, trifluridine, trimethoprim, tropicamide, unoprostone, vidarbine, xylometazoline, pharmaceutically acceptable salts thereof, and combinations thereof.

BRIEF DESCRIPTION OF THE FIGURES

FIG. 1A shows analysis for apoptosis, as assessed by a Flow cytometry after Annexin V/PI staining, which showed that the survival ratios for HRECs (Q3) was 99.3%, 83.2%, 84.3%, 90.7%, 92.8%, and 94.3%, respectively 24 hours after treatment. FIG. 1B is a graphic representation of the survival ratio for HRECs. Data for SS-31 concentrations of 100 nM, 1 μM, and 10 μM were significantly higher than that seen with high glucose exposed cells in the absence of co-treatment with SS31. *p<0.05 vs. 30 mM high glucose treated group.

FIGS. 3A and 3B show that SS-31 prevents the mitochondrial potential loss of HRECs treated with high-glucose. FIG. 3A. The ΔΨm of HRECs was measured by flow cytometry after JC-1 fluorescent probe staining High glucose (30 mM) treatment resulted in a rapid loss of mitochondrial membrane potential of the cultured HRECs at 24 and 48 hours. In contrast, flow cytometric analysis showed that 30 mM glucose co-treated with SS-31 increased ΔΨm compared with the high glucose alone group. FIG. 3B. Quantitative analysis of ΔΨm in high glucose HRECs co-treated with SS-31 for 24 and 48 hours, High glucose alone adversely affected ΔΨm. In contrast, SS-31 restored ΔΨm to control levels. Values represent mean±SD of six separate experiments performed in triplicate. *P<0.05.

FIGS. 4A and 4D are confocal microscopic images showing that HRECs in the normal glucose group and the SS-31 co-treated group have more exact overlapping cytochrome c staining and HSP60 staining at 24 and 48 hours, indicating the co-localization of cytochrome c and mitochondria. Twenty four and 48 hours after treatment, cytochrome c was obviously increased in the cytoplasm of HRECs treated with 30 mM glucose. FIGS. 4B and 4E show the cytochrome c content in mitochondria and cytoplasm as determined by Western blot. FIGS. 4C and 4F show quantitative analysis of the percentage of cytochrome c content in mitochondria and cytoplasm of HRECs co-treated with high glucose and SS-31 for 24 and 48 h.

FIG. 5C shows the mRNA level of Trx2 in HRECs exposed to 30 mM glucose treated with SS-31 for 24 h and 48 h. FIG. 5D shows the level of Trx2 protein expression measured by Western blot. FIG. 5E shows quantitative analysis of the protein level of Trx2 in HRECs 24 and 48 h after high glucose with or without SS-31 co-treatment.

FIG. 27A is a chart showing the effect of different doses of tBHP on cell viability of a 661W cone cell line derived from a mouse retinal tumor. FIG. 27B is a chart showing the effect of 1 $\mu M$ SS-31 in reducing tBHP-induced 661W cell death.

FIG. 31A shows ROS production in control RPE cells; FIG. 31B shows ROS production in RPE cells treated with 500 $\mu M$ tBHP for 3 h; FIG. 31C shows ROS production in RPE cells treated with 500 $\mu M$ tBHP for 3 h and 1 $\mu M$ SS-31.

FIG. 33A: Control group; FIG. 33B: 500 $\mu M$ tBHP for 3 h group; FIG. 33C: 1 $\mu M$ SS-31 for 4 h+500 $\mu M$ tBHP for 3 h group.

FIG. 34A: control group; FIG. 34B: 250 $\mu M$ tBHP for 24 h group; FIG. 34C: 1 $\mu M$ SS-31 for 4 h+250 $\mu M$ tBHP for 24 h group.

FIG. 40 is a series of graphs showing that SS-31 protected against $H_2O_2$-induced mitochondrial depolarization of GTM3 and iHTM cells.

DETAILED DESCRIPTION

Figure 1A:
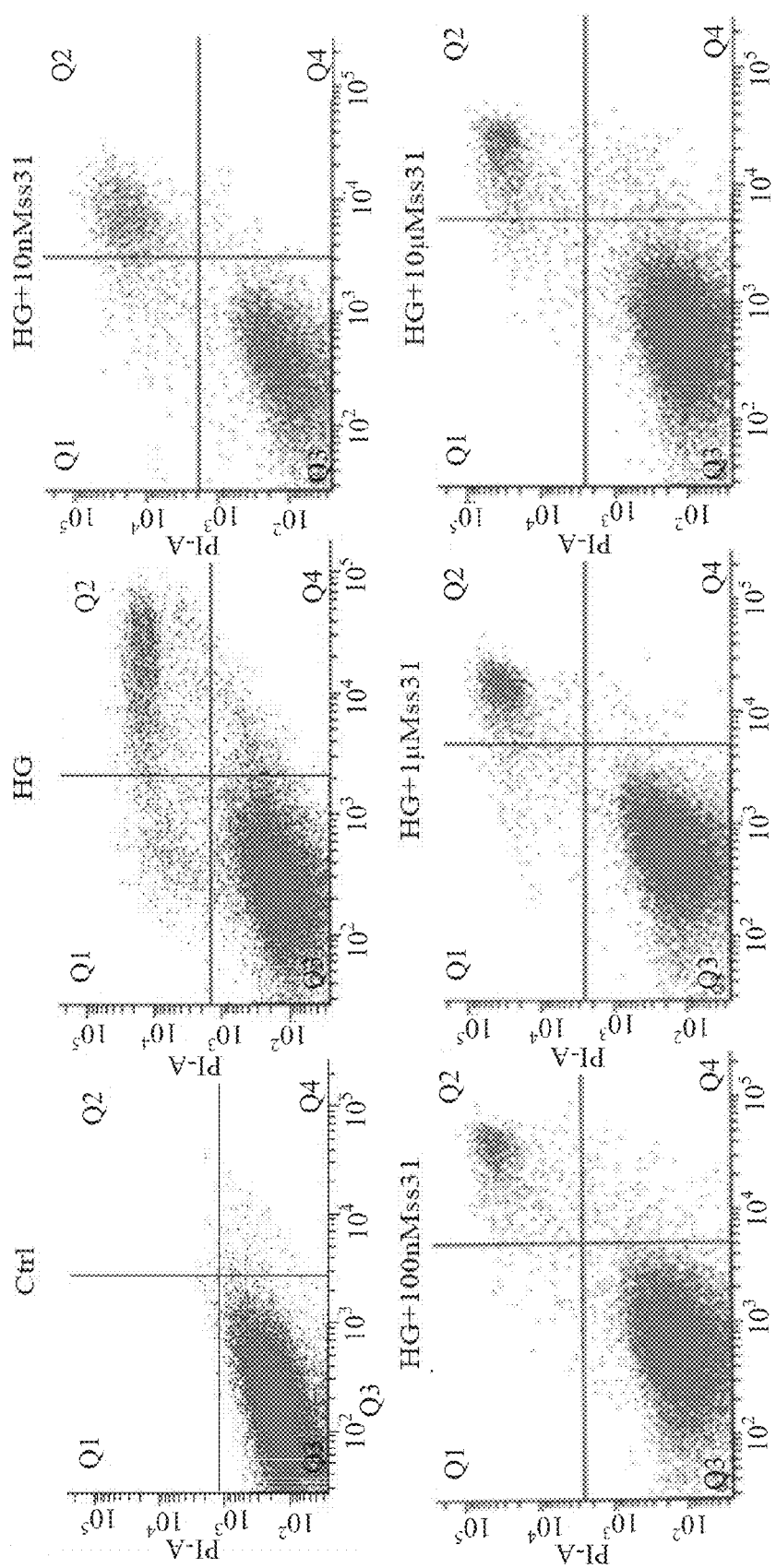
FIGS. 1A and 1B show the effects of different concentrations of SS-31 (10 nM, 100 nM, 1 μM and 10 μM) used as co-treatment with 30 mM glucose (HG).

It is to be appreciated that certain aspects, modes, embodiments, variations and features of the invention are described below in various levels of detail in order to provide a substantial understanding of the present invention.

In practicing the present invention, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively.

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

As used herein, the "administration" of an agent, drug, or peptide to a subject includes any route of introducing or delivering to a subject a compound to perform its intended function. Administration can be carried out by any suitable route, including orally, intraocularly, intranasally, parenterally (intravenously, intramuscularly, intraperitoneally, or subcutaneously), or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic and/or prophylactic effect, e.g., an amount which results in the prevention of, or a decrease in, the symptoms associated with an ophthalmic condition. The amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds. In the methods described herein, the aromatic-cationic peptides may be administered to a subject having one or more signs or symptoms of an ophthalmic condition. For example, a "therapeutically effective amount" of the aromatic-cationic peptides is meant levels in which the physiological effects of an ophthalmic condition are, at a minimum, ameliorated.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for an ophthalmic condition if, after receiving a therapeutic amount of the aromatic-cationic peptides according to the methods described herein, the subject shows observable and/or measurable reduction in or absence of one or more signs and symptoms of an ophthalmic condition. It is also to be appreciated that the various modes of treatment or prevention of medical conditions as described are intended to mean "substantial", which includes total but also less than total treatment or prevention, and wherein some biologically or medically relevant result is achieved.

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

Aromatic-Cationic Peptides

The present technology relates to the treatment or prevention of an ophthalmic condition by administration of certain aromatic-cationic peptides. Without wishing to be limited by theory, the aromatic-cationic peptides may treat or prevent ophthalmic diseases or conditions by reducing the severity or occurrence of oxidative damage in the eye. The aromatic-cationic peptides are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, more preferably about nine, and most preferably about six.

The amino acids of the aromatic-cationic peptides can be any amino acid. As used herein, the term "amino acid" is used to refer to any organic molecule that contains at least one amino group and at least one carboxyl group. Typically, at least one amino group is at the α position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid include hydroxyproline (Hyp).

The peptides optionally contain one or more non-naturally occurring amino acids. Suitably, the peptide has no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are preferably resistant, and more preferably insensitive, to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, preferably less than four, more preferably less than three, and most preferably, less than two contiguous L-amino acids recognized by common proteases, irrespective of whether the amino acids are naturally or non-naturally occurring. Suitably, the peptide has only D-amino acids, and no L-amino acids. If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

Amino acid number and net positive charges ($3p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, preferably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t+1$, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t+1$. In this embodiment, the relationship between the minimum number of aromatic amino acid residues (a) and the total number of net positive charges ($p_t$) is as follows:

TABLE 4

Aromatic groups and net positive charges ($2a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are preferably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following peptide examples:

Lys-D-Arg-Tyr-NH$_2$

Phe-D-Arg-His

D-Tyr-Trp-Lys-NH$_2$

Trp-D-Lys-Tyr-Arg-NH$_2$

Tyr-His-D-Gly-Met

Phe-Arg-D-His-Asp

Tyr-D-Arg-Phe-Lys-Glu-NH$_2$

Met-Tyr-D-Lys-Phe-Arg

D-His-Glu-Lys-Tyr-D-Phe-Arg

Lys-D-Gln-Tyr-Arg-D-Phe-Trp-NH$_2$

Phe-D-Arg-Lys-Trp-Tyr-D-Arg-His

Gly-D-Phe-Lys-Tyr-His-D-Arg-Tyr-NH$_2$

Val-D-Lys-His-Tyr-D-Phe-Ser-Tyr-Arg-NH$_2$

Trp-Lys-Phe-D-Asp-Arg-Tyr-D-His-Lys

Lys-Trp-D-Tyr-Arg-Asn-Phe-Tyr-D-His-NH$_2$

Thr-Gly-Tyr-Arg-D-His-Phe-Trp-D-His-Lys

Asp-D-Trp-Lys-Tyr-D-His-Phe-Arg-D-Gly-Lys-NH$_2$

D-His-Lys-Tyr-D-Phe-Glu-D-Asp-D-His-D-Lys-Arg-Trp-NH$_2$

Ala-D-Phe-D-Arg-Tyr-Lys-D-Trp-His-D-Tyr-Gly-Phe

Tyr-D-His-Phe-D-Arg-Asp-Lys-D-Arg-His-Trp-D-His-Phe

Phe-Phe-D-Tyr-Arg-Glu-Asp-D-Lys-Arg-D-Arg-His-Phe-NH$_2$

Phe-Try-Lys-D-Arg-Trp-His-D-Lys-D-Lys-Glu-Arg-D-Tyr-Thr

Tyr-Asp-D-Lys-Tyr-Phe-D-Lys-D-Arg-Phe-Pro-D-Tyr-His-Lys

Glu-Arg-D-Lys-Tyr-D-Val-Phe-D-His-Trp-Arg-D-Gly-Tyr-Arg-D-Met-NH$_2$

Arg-D-Leu-D-Tyr-Phe-Lys-Glu-D-Lys-Arg-D-Trp-Lys-D-Phe-Tyr-D-Arg-Gly

D-Glu-Asp-Lys-D-Arg-D-His-Phe-Phe-D-Val-Tyr-Arg-Tyr-D-Tyr-Arg-His-Phe-NH$_2$

Asp-Arg-D-Phe-Cys-Phe-D-Arg-D-Lys-Tyr-Arg-D-Tyr-Trp-D-His-Tyr-D-Phe-Lys-Phe

His-Tyr-D-Arg-Trp-Lys-Phe-D-Asp-Ala-Arg-Cys-D-Tyr-His-Phe-D-Lys-Tyr-His-Ser-NH$_2$

Gly-Ala-Lys-Phe-D-Lys-Glu-Arg-Tyr-His-D-Arg-D-Arg-Asp-Tyr-Trp-D-His-Trp-His-D-Lys-Asp

Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$

In one embodiment, a peptide that has mu-opioid receptor agonist activity has the formula Tyr-D-Arg-Phe-Lys-NH$_2$ (referred to herein as "SS-01"). SS-01 has a net positive charge of three, contributed by the amino acids tyrosine, arginine, and lysine and has two aromatic groups contributed by the amino acids phenylalanine and tyrosine. The tyrosine of SS-01 can be a modified derivative of tyrosine such as in 2',6'-dimethyltyrosine to produce the compound having the formula 2',6'-Dmt-D-Arg-Phe-Lys-NH$_2$ (referred to herein as "SS-02"). SS-02 has a molecular weight of 640 and carries a net three positive charge at physiological pH. SS-02 readily penetrates the plasma membrane of several mammalian cell types in an energy-independent manner (Zhao et al., *J. Pharmacol Exp Ther.* 304: 425-432, 2003).

Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methylphenylalanine (Hmp).

An example of an aromatic-cationic peptide that does not have mu-opioid receptor agonist activity has the formula Phe-D-Arg-Phe-Lys-NH$_2$ (referred to herein as "SS-20"). Alternatively, the N-terminal phenylalanine can be a derivative of phenylalanine such as 2',6'-dimethylphenylalanine (2'6'-Dmp). SS-01 containing 2',6'-dimethylphenylalanine at amino acid position 1 has the formula 2',6'-Dmp-D-Arg-Phe-Lys-NH$_2$. In one embodiment, the amino acid sequence of SS-02 is rearranged such that Dmt is not at the N-terminus. An example of such an aromatic-cationic peptide that does not have mu-opioid receptor agonist activity has the formula D-Arg-2'6'-Dmt-Lys-Phe-NH$_2$ (SS-31).

SS-01, SS-20, SS-31, and their derivatives can further include functional analogs. A peptide is considered a functional analog of SS-01, SS-20, or SS-31 if the analog has the same function as SS-01, SS-20, or SS-31. The analog may, for example, be a substitution variant of SS-01, SS-20, or SS-31, wherein one or more amino acids are substituted by another amino acid.

Suitable substitution variants of SS-01, SS-20, or SS-31 include conservative amino acid substitutions. Amino acids may be grouped according to their physicochemical characteristics as follows:

(a) Non-polar amino acids: Ala(A) Ser(S) Thr(T) Pro(P) Gly(G) Cys (C);

(b) Acidic amino acids: Asn(N) Asp(D) Glu(E) Gln(Q);

(c) Basic amino acids: His(H) Arg(R) Lys(K);

(d) Hydrophobic amino acids: Met(M) Leu(L) Ile(I) Val (V); and (e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide.

In some embodiments, the aromatic-cationic peptide has a formula as shown in Table 5.

TABLE 5

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | $NH_2$ |
| Tyr | D-Arg | Phe | Orn | $NH_2$ |
| Tyr | D-Arg | Phe | Dab | $NH_2$ |
| Tyr | D-Arg | Phe | Dap | $NH_2$ |
| 2'6'Dmt | D-Arg | Phe | Lys | $NH_2$ |
| 2'6'Dmt | D-Arg | Phe | Lys-NH(CH$_2$)$_2$—NH-dns | $NH_2$ |
| 2'6'Dmt | D-Arg | Phe | Lys-NH(CH$_2$)$_2$—NH-atn | $NH_2$ |
| 2'6'Dmt | D-Arg | Phe | dnsLys | $NH_2$ |
| 2'6'Dmt | D-Cit | Phe | Lys | $NH_2$ |
| 2'6'Dmt | D-Cit | Phe | Ahp | $NH_2$ |
| 2'6'Dmt | D-Arg | Phe | Orn | $NH_2$ |
| 2'6'Dmt | D-Arg | Phe | Dab | $NH_2$ |
| 2'6'Dmt | D-Arg | Phe | Dap | $NH_2$ |
| 2'6'Dmt | D-Arg | Phe | Ahp(2-aminoheptanoic acid) | $NH_2$ |
| Bio-2'6'Dmt | D-Arg | Phe | Lys | $NH_2$ |
| 3'5'Dmt | D-Arg | Phe | Lys | $NH_2$ |
| 3'5'Dmt | D-Arg | Phe | Orn | $NH_2$ |
| 3'5'Dmt | D-Arg | Phe | Dab | $NH_2$ |
| 3'5'Dmt | D-Arg | Phe | Dap | $NH_2$ |
| Tyr | D-Arg | Tyr | Lys | $NH_2$ |
| Tyr | D-Arg | Tyr | Orn | $NH_2$ |
| Tyr | D-Arg | Tyr | Dab | $NH_2$ |
| Tyr | D-Arg | Tyr | Dap | $NH_2$ |
| 2'6'Dmt | D-Arg | Tyr | Lys | $NH_2$ |
| 2'6'Dmt | D-Arg | Tyr | Orn | $NH_2$ |
| 2'6'Dmt | D-Arg | Tyr | Dab | $NH_2$ |
| 2'6'Dmt | D-Arg | Tyr | Dap | $NH_2$ |
| 2'6'Dmt | D-Arg | 2'6'Dmt | Lys | $NH_2$ |
| 2'6'Dmt | D-Arg | 2'6'Dmt | Orn | $NH_2$ |
| 2'6'Dmt | D-Arg | 2'6'Dmt | Dab | $NH_2$ |
| 2'6'Dmt | D-Arg | 2'6'Dmt | Dap | $NH_2$ |
| 3'5'Dmt | D-Arg | 3'5'Dmt | Arg | $NH_2$ |
| 3'5'Dmt | D-Arg | 3'5'Dmt | Lys | $NH_2$ |
| 3'5'Dmt | D-Arg | 3'5'Dmt | Orn | $NH_2$ |
| 3'5'Dmt | D-Arg | 3'5'Dmt | Dab | $NH_2$ |
| Tyr | D-Lys | Phe | Dap | $NH_2$ |
| Tyr | D-Lys | Phe | Arg | $NH_2$ |
| Tyr | D-Lys | Phe | Lys | $NH_2$ |
| Tyr | D-Lys | Phe | Orn | $NH_2$ |
| 2'6'Dmt | D-Lys | Phe | Dab | $NH_2$ |
| 2'6'Dmt | D-Lys | Phe | Dap | $NH_2$ |
| 2'6'Dmt | D-Lys | Phe | Arg | $NH_2$ |
| 2'6'Dmt | D-Lys | Phe | Lys | $NH_2$ |
| 3'5'Dmt | D-Lys | Phe | Orn | $NH_2$ |
| 3'5'Dmt | D-Lys | Phe | Dab | $NH_2$ |
| 3'5'Dmt | D-Lys | Phe | Dap | $NH_2$ |
| 3'5'Dmt | D-Lys | Phe | Arg | $NH_2$ |
| Tyr | D-Lys | Tyr | Lys | $NH_2$ |
| Tyr | D-Lys | Tyr | Orn | $NH_2$ |
| Tyr | D-Lys | Tyr | Dab | $NH_2$ |
| Tyr | D-Lys | Tyr | Dap | $NH_2$ |
| 2'6'Dmt | D-Lys | Tyr | Lys | $NH_2$ |
| 2'6'Dmt | D-Lys | Tyr | Orn | $NH_2$ |
| 2'6'Dmt | D-Lys | Tyr | Dab | $NH_2$ |
| 2'6'Dmt | D-Lys | Tyr | Dap | $NH_2$ |
| 2'6'Dmt | D-Lys | 2'6'Dmt | Lys | $NH_2$ |
| 2'6'Dmt | D-Lys | 2'6'Dmt | Orn | $NH_2$ |
| 2'6'Dmt | D-Lys | 2'6'Dmt | Dab | $NH_2$ |
| 2'6'Dmt | D-Lys | 2'6'Dmt | Dap | $NH_2$ |
| 2'6'Dmt | D-Arg | Phe | dnsDap | $NH_2$ |
| 2'6'Dmt | D-Arg | Phe | atnDap | $NH_2$ |
| 3'5'Dmt | D-Lys | 3'5'Dmt | Lys | $NH_2$ |
| 3'5'Dmt | D-Lys | 3'5'Dmt | Orn | $NH_2$ |
| 3'5'Dmt | D-Lys | 3'5'Dmt | Dab | $NH_2$ |
| 3'5'Dmt | D-Lys | 3'5'Dmt | Dap | $NH_2$ |
| Tyr | D-Lys | Phe | Arg | $NH_2$ |
| Tyr | D-Orn | Phe | Arg | $NH_2$ |
| Tyr | D-Dab | Phe | Arg | $NH_2$ |
| Tyr | D-Dap | Phe | Arg | $NH_2$ |
| 2'6'Dmt | D-Arg | Phe | Arg | $NH_2$ |
| 2'6'Dmt | D-Lys | Phe | Arg | $NH_2$ |
| 2'6'Dmt | D-Orn | Phe | Arg | $NH_2$ |
| 2'6'Dmt | D-Dab | Phe | Arg | $NH_2$ |
| 3'5'Dmt | D-Dap | Phe | Arg | $NH_2$ |
| 3'5'Dmt | D-Arg | Phe | Arg | $NH_2$ |
| 3'5'Dmt | D-Lys | Phe | Arg | $NH_2$ |
| 3'5'Dmt | D-Orn | Phe | Arg | $NH_2$ |
| Tyr | D-Lys | Tyr | Arg | $NH_2$ |
| Tyr | D-Orn | Tyr | Arg | $NH_2$ |
| Tyr | D-Dab | Tyr | Arg | $NH_2$ |
| Tyr | D-Dap | Tyr | Arg | $NH_2$ |
| 2'6'Dmt | D-Arg | 2'6'Dmt | Arg | $NH_2$ |
| 2'6'Dmt | D-Lys | 2'6'Dmt | Arg | $NH_2$ |
| 2'6'Dmt | D-Orn | 2'6'Dmt | Arg | $NH_2$ |
| 2'6'Dmt | D-Dab | 2'6'Dmt | Arg | $NH_2$ |
| 3'5'Dmt | D-Dap | 3'5'Dmt | Arg | $NH_2$ |
| 3'5'Dmt | D-Arg | 3'5'Dmt | Arg | $NH_2$ |
| 3'5'Dmt | D-Lys | 3'5'Dmt | Arg | $NH_2$ |
| 3'5'Dmt | D-Orn | 3'5'Dmt | Arg | $NH_2$ |
| Mmt | D-Arg | Phe | Lys | $NH_2$ |
| Mmt | D-Arg | Phe | Orn | $NH_2$ |
| Mmt | D-Arg | Phe | Dab | $NH_2$ |
| Mmt | D-Arg | Phe | Dap | $NH_2$ |
| Tmt | D-Arg | Phe | Lys | $NH_2$ |
| Tmt | D-Arg | Phe | Orn | $NH_2$ |
| Tmt | D-Arg | Phe | Dab | $NH_2$ |
| Tmt | D-Arg | Phe | Dap | $NH_2$ |
| Hmt | D-Arg | Phe | Lys | $NH_2$ |
| Hmt | D-Arg | Phe | Orn | $NH_2$ |
| Hmt | D-Arg | Phe | Dab | $NH_2$ |
| Hmt | D-Arg | Phe | Dap | $NH_2$ |
| Mmt | D-Lys | Phe | Lys | $NH_2$ |
| Mmt | D-Lys | Phe | Orn | $NH_2$ |
| Mmt | D-Lys | Phe | Dab | $NH_2$ |
| Mmt | D-Lys | Phe | Dap | $NH_2$ |
| Mmt | D-Lys | Phe | Arg | $NH_2$ |
| Tmt | D-Lys | Phe | Lys | $NH_2$ |
| Tmt | D-Lys | Phe | Orn | $NH_2$ |
| Tmt | D-Lys | Phe | Dab | $NH_2$ |
| Tmt | D-Lys | Phe | Dap | $NH_2$ |
| Tmt | D-Lys | Phe | Arg | $NH_2$ |
| Hmt | D-Lys | Phe | Lys | $NH_2$ |
| Hmt | D-Lys | Phe | Orn | $NH_2$ |
| Hmt | D-Lys | Phe | Dab | $NH_2$ |
| Hmt | D-Lys | Phe | Dap | $NH_2$ |
| Hmt | D-Lys | Phe | Arg | $NH_2$ |
| Mmt | D-Lys | Phe | Arg | $NH_2$ |
| Mmt | D-Orn | Phe | Arg | $NH_2$ |
| Mmt | D-Dab | Phe | Arg | $NH_2$ |
| Mmt | D-Dap | Phe | Arg | $NH_2$ |
| Mmt | D-Arg | Phe | Arg | $NH_2$ |
| Tmt | D-Lys | Phe | Arg | $NH_2$ |
| Tmt | D-Orn | Phe | Arg | $NH_2$ |
| Tmt | D-Dab | Phe | Arg | $NH_2$ |
| Tmt | D-Dap | Phe | Arg | $NH_2$ |
| Tmt | D-Arg | Phe | Arg | $NH_2$ |
| Hmt | D-Lys | Phe | Arg | $NH_2$ |
| Hmt | D-Orn | Phe | Arg | $NH_2$ |
| Hmt | D-Dab | Phe | Arg | $NH_2$ |
| Hmt | D-Dap | Phe | Arg | $NH_2$ |
| Hmt | D-Arg | Phe | Arg | $NH_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of other aromatic-cationic peptides that do not activate mu-opioid receptors include, but are not limited to, the aromatic-cationic peptides shown in Table 6.

TABLE 6

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| Phe | Lys | Dmt | D-Arg | $NH_2$ |
| Phe | Lys | D-Arg | Dmt | $NH_2$ |
| Phe | D-Arg | Phe | Lys | $NH_2$ |
| Phe | D-Arg | Dmt | Lys | $NH_2$ |
| Phe | D-Arg | Lys | Dmt | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |
| Cha | D-Arg | Phe | Lys | $NH_2$ |
| Ala | D-Arg | Phe | Lys | $NH_2$ |

Cha = cyclohexyl alanine

The amino acids of the peptides shown in Table 5 and 6 may be in either the L- or the D-configuration.

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.* 289, Academic Press, Inc, New York (1997).

Prophylactic and Therapeutic Uses of Aromatic-Cationic Peptides.

The aromatic-cationic peptides described herein are useful to prevent or treat disease. Specifically, the disclosure provides for both prophylactic and therapeutic methods of treating a subject at risk of (or susceptible to) an ophthalmic disease or condition. Accordingly, the present methods provide for the prevention and/or treatment of an ophthalmic condition in a subject by administering an effective amount of an aromatic-cationic peptide to a subject in need thereof. For example, a subject can be administered an aromatic-cationic peptide compositions in an effort to improve one or more of the factors contributing to an ophthalmic disease or condition.

One aspect of the technology includes methods of reducing an ophthalmic condition in a subject for therapeutic purposes. In therapeutic applications, compositions or medicaments are administered to a subject suspected of, or already suffering from such a disease in an amount sufficient to cure, or at least partially arrest, the symptoms of the disease, including its complications and intermediate pathological phenotypes in development of the disease. As such, the disclosure provides methods of treating an individual afflicted with an ophthalmic condition. In some embodiments, the technology provides a method of treating or preventing specific ophthalmic disorders, such as diabetic retinopathy, cataracts, retinitis pigmentosa, glaucoma, choroidal neovascularization, retinal degeneration, and oxygen-induced retinopathy, in a mammal by administering an aromatic cationic peptide.

In one embodiment, an aromatic-cationic peptide is administered to a subject to treat or prevent diabetic retinopathy. Diabetic retinopathy is characterized by capillary microaneurysms and dot hemorrhaging. Thereafter, microvascular obstructions cause cotton wool patches to form on the retina. Moreover, retinal edema and/or hard exudates may form in individuals with diabetic retinopathy due to increased vascular hyperpermeability. Subsequently, neovascularization appears and retinal detachment is caused by traction of the connective tissue grown in the vitreous body. Iris rubeosis and neovascular glaucoma may also occur which, in turn, can lead to blindness. The symptoms of diabetic retinopathy include, but are not limited to, difficulty reading, blurred vision, sudden loss of vision in one eye, seeing rings around lights, seeing dark spots, and/or seeing flashing lights.

In one embodiment, an aromatic-cationic peptide is administered to a subject to treat or prevent cataracts. Cataracts is a congenital or acquired disease characterized by a reduction in natural lens clarity. Individuals with cataracts may exhibit one or more symptoms, including, but not limited to, cloudiness on the surface of the lens, cloudiness on the inside of the lens, and/or swelling of the lens. Typical examples of congenital cataract-associated diseases are pseudo-cataracts, membrane cataracts, coronary cataracts, lamellar cataracts, punctuate cataracts, and filamentary cataracts. Typical examples of acquired cataract-associated diseases are geriatric cataracts, secondary cataracts, browning cataracts, complicated cataracts, diabetic cataracts, and traumatic cataracts. Acquired cataracts is also inducible by electric shock, radiation, ultrasound, drugs, systemic diseases, and nutritional disorders. Acquired cataracts further includes postoperative cataracts.

In one embodiment, an aromatic-cationic peptide is administered to a subject to treat or prevent retinitis pigmentosa. Retinitis pigmentosa is a disorder that is characterized by rod and/or cone cell damage. The presence of dark lines in the retina is typical in individuals suffering from retinitis pigmentosa. Individuals with retinitis pigmentosa also present with a variety of symptoms including, but not limited to, headaches, numbness or tingling in the extremities, light flashes, and/or visual changes. See, e.g., Heckenlively et al., *Clinical findings and common symptoms in retinitis pigmentosa. Am J. Ophthalmol.* 105(5): 504-511 (1988).

In one embodiment, an aromatic-cationic peptide is administered to a subject to treat or prevent glaucoma. Glaucoma is a genetic disease characterized by an increase in intraocular pressure, which leads to a decrease in vision. Glaucoma may emanate from various ophthalmologic conditions that are already present in an individual, such as, wounds, surgery, and other structural malformations. Although glaucoma can occur at any age, it frequently develops in elderly individuals and leads to blindness. Glaucoma patients typically have an intraocular pressure in excess of 21 mmHg. However, normal tension glaucoma, where glaucomatous alterations are found in the visual field and optic papilla, can occur in the absence of such increased intraocular pressures, i.e., greater than 21 mmHg. Symptoms of glaucoma include, but are not limited to, blurred vision, severe eye pain, headache, seeing haloes around lights, nausea, and/or vomiting.

In one embodiment, an aromatic-cationic peptide is administered to a subject to treat or prevent macular degeneration. Macular degeneration is typically an age-related disease. The general categories of macular degeneration include wet, dry, and non-aged related macular degeneration. Dry macular degeneration, which accounts for about 80-90 percent of all cases, is also known as atrophic, nonexudative, or drusenoid macular degeneration. With dry macular degeneration, drusen typically accumulate beneath the retinal pigment epithelium tissue. Vision loss subsequently occurs when drusen interfere with the function of photoreceptors in the macula. Symptoms of dry macular generation include, but are not limited to, distorted vision, center-vision distortion, light or dark distortion, and/or changes in color perception. Dry macular degeneration can result in the gradual loss of vision.

Wet macular degeneration is also known as neovascularization, subretinal neovascularization, exudative, or disciform degeneration. With wet macular degeneration, abnormal blood vessels grow beneath the macula. The blood vessels leak fluid into the macula and damage photoreceptor cells. Wet macular degeneration can progress rapidly and cause severe damage to central vision. Wet and dry macular degeneration have identical symptoms. Non-age related macular degeneration, however, is rare and may be linked to heredity, diabetes, nutritional deficits, injury, infection, or other factors. The symptoms of non-age related macular degeneration also include, but are not limited to, distorted vision, center-vision distortion, light or dark distortion, and/or changes in color perception.

In one embodiment, an aromatic-cationic peptide is administered to a subject to treat or prevent choroidal neovascularization. Choroidal neovascularization (CNV) is a disease characterized by the development of new blood vessels in the choroid layer of the eye. The newly formed blood vessels grow in the choroid, through the Bruch membrane, and invade the subretinal space. CNV can lead to the impairment of sight or complete loss of vision. Symptoms of CNV include, but are not limited to, seeing flickering, blinking lights, or gray spots in the affected eye or eyes, blurred vision, distorted vision, and/or loss of vision.

In one embodiment, an aromatic-cationic peptide is administered to a subject to treat or prevent retinal degeneration. Retinal degeneration is a genetic disease that relates to the break-down of the retina. Retinal tissue may degenerate for various reasons, such as, artery or vein occlusion, diabetic retinopathy, retinopathy of prematurity, and/or retrolental fibroplasia. Retinal degradation generally includes retinoschisis, lattic degeneration, and is related to progressive macular degeneration. The symptoms of retina degradation include, but are not limited to, impaired vision, loss of vision, night blindness, tunnel vision, loss of peripheral vision, retinal detachment, and/or light sensitivity.

In one embodiment, an aromatic-cationic peptide is administered to a subject to treat or prevent oxygen-induced retinopathy. Oxygen-induced retinopathy (OIR) is a disease characterized by microvascular degeneration. OIR is an established model for studying retinopathy of prematurity. OIR is associated with vascular cell damage that culminates in abnormal neovascularization. Microvascular degeneration leads to ischemia which contributes to the physical changes associated with OIR. Oxidative stress also plays an important role in the vasoobliteration of OIR where endothelial cells are prone to peroxidative damage. Pericytes, smooth muscle cells, and perivascular astrocytes, however, are generally resistant to peroxidative injury. See, e.g., Beauchamp et al., *Role of thromboxane in retinal microvascular degeneration in oxygen-induced retinopathy*, J Appl Physiol. 90: 2279-2288 (2001). OIR, including retinopathy of prematurity, is generally asymptomatic. However, abnormal eye movements, crossed eyes, severe nearsightedness, and/or leukocoria, can be a sign of OIR or retinopathy of prematurity.

In one aspect, the invention provides a method for preventing, in a subject, an ophthalmic condition by administering to the subject an aromatic-cationic peptide that modulates one or more signs or markers of an ophthalmic condition. Subjects at risk for an ophthalmic condition can be identified by, e.g., any or a combination of diagnostic or prognostic assays as described herein. In prophylactic applications, pharmaceutical compositions or medicaments of aromatic-cationic peptides are administered to a subject susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Administration of a prophylactic aromatic-cationic can occur prior to the manifestation of symptoms characteristic of the aberrancy, such that a disease or disorder is prevented or, alternatively, delayed in its progression. Depending upon the type of aberrancy, e.g., an aromatic-cationic peptide which acts to enhance or improve mitochondrial function or reduce oxidative damage can be used for treating the subject. The appropriate compound can be determined based on screening assays described herein.

Determination of the Biological Effect of the Aromatic-Cationic Peptide-Based Therapeutic.

In various embodiments, suitable in vitro or in vivo assays are performed to determine the effect of a specific aromatic-cationic peptide-based therapeutic and whether its administration is indicated for treatment. In various embodiments, in vitro assays can be performed with representative cells of the type(s) involved in the subject's disorder, to determine if a given aromatic-cationic peptide-based therapeutic exerts the desired effect upon the cell type(s). Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects. In one embodiment, administration of an aromatic-cationic peptide to a subject exhibiting symptoms associated with an ophthalmic condition will cause an improvement in one or more of those symptoms.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an aromatic-cationic peptide, such as those described above, to a mammal, preferably a human. When used in vivo for therapy, the aromatic-cationic peptides are administered to the subject in effective amounts (i.e., amounts that have desired therapeutic effect). The dose and dosage regimen will depend upon the degree of the ophthalmic condition in the subject, the characteristics of the particular aromatic-cationic peptide used, e.g., its therapeutic index, the subject, and the subject's history.

The effective amount may be determined during pre-clinical trials and clinical trials by methods familiar to physicians and clinicians. An effective amount of a peptide useful in the methods of the present invention, preferably in a pharmaceutical composition, may be administered to a mammal in need thereof by any of a number of well-known methods for administering pharmaceutical compounds. In some embodiments, the peptide may be administered systemically, topically, or intraocularly.

The aromatic-cationic peptides described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it may be desirable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

For ophthalmic applications, the therapeutic compound is formulated into solutions, suspensions, and ointments appropriate for use in the eye. For ophthalmic formulations generally, see Mitra (ed.), *Ophthalmic Drug Delivery Systems*, Marcel Dekker, Inc., New York, N.Y. (1993) and also Havener, W. H., *Ocular Pharmacology*, C.V. Mosby Co., St. Louis (1983). Ophthalmic pharmaceutical compositions may be adapted for topical administration to the eye in the form of solutions, suspensions, ointments, creams or as a solid insert. For a single dose, from between 0.1 ng to 5000 µg, 1 ng to 500 µg, or 10 ng to 100 µg of the aromatic-cationic peptides can be applied to the human eye.

The ophthalmic preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The ophthalmic solution or suspension may be administered as often as necessary to maintain an acceptable level of the aromatic-cationic peptide in the eye. Administration to the mammalian eye may be about once or twice daily.

Oral compositions generally include an inert diluent or an edible carrier. For the purpose of oral therapeutic administration, the active compound can be incorporated with excipients and used in the form of tablets, troches, or capsules, e.g., gelatin capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic protein or peptide can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. As one skilled in the art would appreciate, there are a variety of methods to prepare liposomes. (See Lichtenberg et al., *Methods Biochem. Anal.*, 33:337-462 (1988); Anselem et al., *Liposome Technology*, CRC Press (1993)). Liposomal formulations can delay clearance and increase cellular uptake (See Reddy, *Ann. Pharmacother.*, 34 (7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34 (7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods* 4 (3) 201-9 (1994); and Gregoriadis, "Engineering Liposomes for Drug Delivery: Progress and Problems," *Trends Biotechnol.* 13 (12):527-37 (1995). Mizguchi et al., *Cancer Lett.* 100:63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the aromatic-cationic peptides, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.1-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. Intervals can also be irregular as indicated by measuring blood levels of glucose or insulin in the subject and adjusting dosage or administration accordingly. In therapeutic applications, a relatively high dosage at relatively short intervals is sometimes required until progression of the disease is reduced or terminated, and preferably until the subject shows partial or complete amelioration of symptoms of disease. Thereafter, the patient can be administered a prophylactic regime.

In some embodiments, a therapeutically effective amount of an aromatic-cationic peptide may be defined as a concentration of peptide at the target tissue of $10^{-11}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, most preferably by single daily or weekly administration, but also including continuous administration (e.g., parenteral infusion or transdermal application).

In some embodiments, the dosage of the aromatic-cationic peptide is provided at a "low," "mid," or "high" dose level. In one embodiment, the low dose is provided from about 0.0001 to about 0.5 mg/kg/h, suitably from about 0.01 to about 0.1 mg/kg/h. In one embodiment, the mid-dose is provided from about 0.1 to about 1.0 mg/kg/h, suitably from about 0.1 to about 0.5 mg/kg/h. In one embodiment, the high dose is provided from about 0.5 to about 10 mg/kg/h, suitably from about 0.5 to about 2 mg/kg/h.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In a preferred embodiment, the mammal is a human.

Combination Therapy with an Aromatic-Cationic Peptide and Other Therapeutic Agents In certain instances, it may be appropriate to administer at least one of the aromatic-cationic peptides described herein (or a pharmaceutically acceptable salt, ester, amide, prodrug, or solvate) in combination with another therapeutic agent. By way of example only, if one of the side effects experienced by a patient upon receiving one of the aromatic-cationic peptides herein is inflammation, then it may be appropriate to administer an anti-inflammatory agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit in the prevention or treatment of ophthalmic conditions. By way of example only, in a treatment for macular degeneration involving administration of one of the aromatic-cationic peptides described herein, increased therapeutic benefit may result by also providing the patient with other therapeutic agents or therapies for macular degeneration. In any case, regardless of the ophthalmic disease, disorder or condition being treated, the overall benefit experienced by the patient may simply be additive of the two therapeutic agents or the patient may experience a synergistic benefit.

Specific, non-limiting examples of possible combination therapies include use of at least one aromatic-cationic peptide with nitric oxide (NO) inducers, statins, negatively charged phospholipids, antioxidants, minerals, anti-inflammatory agents, anti-angiogenic agents, matrix metalloproteinase inhibitors, and carotenoids. In several instances, suitable combination agents may fall within multiple categories (by way of example only, lutein is an antioxidant and a carotenoid). Further, the aromatic-cationic peptides may also be administered with additional agents that may provide benefit to the patient, including by way of example only cyclosporin A.

In addition, the aromatic-cationic peptides may also be used in combination with procedures that may provide additional or synergistic benefit to the patient, including, by way of example only, the use of extracorporeal rheopheresis (also known as membrane differential filtration), the use of implantable miniature telescopes, laser photocoagulation of drusen, and microstimulation therapy.

The use of antioxidants has been shown to benefit patients with macular degenerations and dystrophies. See, e.g., *Arch. Ophthalmol.*, 119: 1417-36 (2001); Sparrow, et al., *J. Biol. Chem.*, 278:18207-13 (2003). Examples of suitable antioxidants that could be used in combination with at least one aromatic-cationic peptide include vitamin C, vitamin E, beta-carotene and other carotenoids, coenzyme Q, 4-hydroxy-2,2, 6,6-tetramethylpiperidine-N-oxyl (also known as Tempol), lutein, butylated hydroxytoluene, resveratrol, a trolox analogue (PNU-83836-E), and bilberry extract.

The use of certain minerals has also been shown to benefit patients with macular degenerations and dystrophies. See, e.g., *Arch. Ophthalmol.*, 119: 1417-36 (2001). Examples of suitable minerals that could be used in combination with at least one aromatic-cationic peptide include copper-containing minerals, such as cupric oxide; zinc-containing minerals, such as zinc oxide; and selenium-containing compounds.

The use of certain negatively-charged phospholipids has also been shown to benefit patients with macular degenerations and dystrophies. See, e.g., Shaban & Richter, *Biol. Chem.*, 383:537-45 (2002); Shaban, et al., *Exp. Eye Res.*, 75:99-108 (2002). Examples of suitable negatively charged phospholipids that could be used in combination with at least one aromatic-cationic peptide include cardiolipin and phosphatidylglycerol. Positively-charged and/or neutral phospholipids may also provide benefit for patients with macular degenerations and dystrophies when used in combination with aromatic-cationic peptides.

The use of certain carotenoids has been correlated with the maintenance of photoprotection necessary in photoreceptor cells. Carotenoids are naturally-occurring yellow to red pigments of the terpenoid group that can be found in plants, algae, bacteria, and certain animals, such as birds and shellfish. Carotenoids are a large class of molecules in which more than 600 naturally occurring carotenoids have been identified. Carotenoids include hydrocarbons (carotenes) and their oxygenated, alcoholic derivatives (xanthophylls). They include actinioerythrol, astaxanthin, canthaxanthin, capsanthin, capsorubin, β-8'-apo-carotenal (apo-carotenal), β-12'-apo-carotenal, α-carotene, β-carotene, "carotene" (a mixture of α- and β-carotenes), δ-carotenes, β-cyrptoxanthin, lutein, lycopene, violerythrin, zeaxanthin, and esters of hydroxyl- or carboxyl-containing members thereof. Many of the carotenoids occur in nature as cis- and trans-isomeric forms, while synthetic compounds are frequently racemic mixtures.

In humans, the retina selectively accumulates mainly two carotenoids: zeaxanthin and lutein. These two carotenoids are thought to aid in protecting the retina because they are powerful antioxidants and absorb blue light. Studies with quails establish that groups raised on carotenoid-deficient diets had retinas with low concentrations of zeaxanthin and suffered severe light damage, as evidenced by a very high number of apoptotic photoreceptor cells, while the group with high zeaxanthin concentrations had minimal damage. Examples of suitable carotenoids for in combination with at least one aromatic-cationic peptide include lutein and zeaxanthin, as well as any of the aforementioned carotenoids.

Suitable nitric oxide inducers include compounds that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosine, bradykinin, calreticulin, bisacodyl, and phenolphthalein. EDRF is a vascular relaxing factor secreted by the endothelium, and has been identified as nitric oxide or a closely related derivative thereof (Palmer et al, *Nature,* 327: 524-526 (1987); Ignarro et al, *Proc. Natl. Acad. Sci. USA,* 84:9265-9269 (1987)).

Statins serve as lipid-lowering agents and/or suitable nitric oxide inducers. In addition, a relationship has been demonstrated between statin use and delayed onset or development of macular degeneration. G. McGwin, et al., *British Journal of Ophthalmology,* 87:1121-25 (2003). Statins can thus provide benefit to a patient suffering from an ophthalmic condition (such as the macular degenerations and dystrophies, and the retinal dystrophies) when administered in combination with aromatic-cationic peptides. Suitable statins include, by way of example only, rosuvastatin, pitivastatin, simvastatin, pravastatin, cerivastatin, mevastatin, velostatin, fluvastatin, compactin, lovastatin, dalvastatin, fluindostatin, atorvastatin, atorvastatin calcium (which is the hemicalcium salt of atorvastatin), and dihydrocompactin.

Suitable anti-inflammatory agents with which the aromatic-cationic peptides may be used include, by way of example only, aspirin and other salicylates, cromolyn, nedocromil, theophylline, zileuton, zafirlukast, montelukast, pranlukast, indomethacin, and lipoxygenase inhibitors; non-steroidal antiinflammatory drugs (NSAIDs) (such as ibuprofen and naproxin); prednisone, dexamethasone, cyclooxygenase inhibitors (i.e., COX-1 and/or COX-2 inhibitors such as Naproxen™, or Celebrex™); statins (by way of example only, rosuvastatin, pitivastatin, simvastatin, pravastatin, cerivastatin, mevastatin, velostatin, fluvastatin, compactin, lovastatin, dalvastatin, fluindostatin, atorvastatin, atorvastatin calcium (which is the hemicalcium salt of atorvastatin), and dihydrocompactin); and disassociated steroids.

Suitable matrix metalloproteinases (MMPs) inhibitors may also be administered in combination with aromatic-cationic peptides in order to treat ophthalmic conditions or symptoms associated with macular or retinal degenerations. MMPs are known to hydrolyze most components of the extracellular matrix. These proteinases play a central role in many biological processes such as normal tissue remodeling, embryogenesis, wound healing and angiogenesis. However, excessive expression of MMP has been observed in many disease states, including macular degeneration. Many MMPs have been identified, most of which are multidomain zinc endopeptidases. A number of metalloproteinase inhibitors are known (see for example the review of MMP inhibitors by Whittaker M. et al, *Chemical Reviews* 99(9):2735-2776 (1999)). Representative examples of MMP Inhibitors include Tissue Inhibitors of Metalloproteinases (TIMPs) (e.g., TIMP-1, TIMP-2, TIMP-3, or TIMP-4), α-2-macroglobulin, tetracyclines (e.g., tetracycline, minocycline, and doxycycline), hydroxamates (e.g., BATIMASTAT, MARIMISTAT and TROCADE), chelators (e.g., EDTA, cysteine, acetylcysteine, D-penicillamine, and gold salts), synthetic MMP fragments, succinyl mercaptopurines, phosphonamidates, and hydroxaminic acids. Examples of MMP inhibitors that may be used in combination with aromatic cationic peptides include, by way of example only, any of the aforementioned inhibitors.

The use of antiangiogenic or anti-VEGF drugs has also been shown to provide benefit for patients with macular degenerations and dystrophies. Examples of suitable antiangiogenic or anti-VEGF drugs that could be used in combination with at least one aromatic-cationic peptide include Rhufab V2 (Lucentis™), Tryptophanyl-tRNA synthetase (TrpRS), Eye001 (Anti-VEGF Pegylated Aptamer), squalamine, Retaane™ 15 mg (anecortave acetate for depot suspension; Alcon, Inc.), Combretastatin A4 Prodrug (CA4P), Macugen™, Mifeprex™ (mifepristone—ru486), subtenon triamcinolone acetonide, intravitreal crystalline triamcinolone acetonide, Prinomastat (AG3340—synthetic matrix metalloproteinase inhibitor, Pfizer), fluocinolone acetonide (including fluocinolone intraocular implant, Bausch & Lomb/Control Delivery Systems), VEGFR inhibitors (Sugen), and VEGF-Trap (Regeneron/Aventis).

Other pharmaceutical therapies that have been used to relieve visual impairment can be used in combination with at least one aromatic-cationic peptide. Such treatments include but are not limited to agents such as Visudyne™ with use of a non-thermal laser, PKC 412, Endovion (NeuroSearch A/S), neurotrophic factors, including by way of example Glial Derived Neurotrophic Factor and Ciliary Neurotrophic Factor, diatazem, dorzolamide, Phototrop, 9-cis-retinal, eye medication (including Echo Therapy) including phospholine iodide or echothiophate or carbonic anhydrase inhibitors, AE-941 (AEterna Laboratories, Inc.), Sirna-027 (Sirna Therapeutics, Inc.), pegaptanib (NeXstar Pharmaceuticals/Gilead Sciences), neurotrophins (including, by way of example only, NT-4/5, Genentech), Candy (Acuity Pharmaceuticals), ranibizumab (Genentech), INS-37217 (Inspire Pharmaceuticals), integrin antagonists (including those from Jerini AG and Abbott Laboratories), EG-3306 (Ark Therapeutics Ltd.), BDM-E (BioDiem Ltd.), thalidomide (as used, for example, by EntreMed, Inc.), cardiotrophin-1 (Genentech), 2-methoxyestradiol (Allergan/Oculex), DL-8234 (Toray Industries), NTC-200 (Neurotech), tetrathiomolybdate (University of Michigan), LYN-002 (Lynkeus Biotech), microalgal compound (Aquasearch/Albany, Mera Pharmaceuticals), D-9120 (Celltech Group plc), ATX-S10 (Hamamatsu Photonics), TGF-beta 2 (Genzyme/Celtrix), tyrosine kinase inhibitors (Allergan, SUGEN, Pfizer), NX-278-L (NeXstar Pharmaceuticals/Gilead Sciences), Opt-24 (OPTIS France SA), retinal cell ganglion neuroprotectants (Cogent Neurosciences), N-nitropyrazole derivatives (Texas A&M University System), KP-102 (Krenitsky Pharmaceuticals), and cyclosporin A.

In any case, the multiple therapeutic agents may be administered in any order or even simultaneously. If simultaneously, the multiple therapeutic agents may be provided in a single, unified form, or in multiple forms (by way of example only, either as a single solution or as two separate solutions). One of the therapeutic agents may be given in multiple doses, or both may be given as multiple doses. If not simultaneous, the timing between the multiple doses may vary from more than zero weeks to less than about four weeks, less than about six weeks, less than about 2 months, less than about 4 months, less than about 6 months, or less than about one year. In addition, the combination methods, compositions and formulations are not to be limited to the use of only two agents. By way of example only, an aromatic-cationic peptide may be provided with at least one antioxidant and at least one negatively charged phospholipid; or an aromatic-cationic peptide may be provided with at least one antioxidant and at least one inducer of nitric oxide production; or an aromatic-cationic peptide may be provided with at least one inducer of nitric oxide productions and at least one negatively charged phospholipid; and so forth.

In addition, an aromatic-cationic peptide may also be used in combination with procedures that may provide additional or synergistic benefits to the patient. Procedures known, proposed or considered to relieve visual impairment include but are not limited to "limited retinal translocation", photodynamic therapy (including, by way of example only, receptor-targeted PDT, Bristol-Myers Squibb, Co.; porfimer sodium for injection with PDT; verteporfin, QLT Inc.; rostaporfin with PDT, Miravent Medical Technologies; talaporfin sodium with PDT, Nippon Petroleum; motexafin lutetium, Pharmacyclics, Inc.), antisense oligonucleotides (including, by way of example, products tested by Novagali Pharma SA and ISIS-13650, Isis Pharmaceuticals), laser photocoagulation, drusen lasering, macular hole surgery, macular translocation surgery, implantable miniature telescopes, Phi-Motion Angiography (also known as Micro-Laser Therapy and Feeder Vessel Treatment), Proton Beam Therapy, microstimulation therapy, Retinal Detachment and Vitreous Surgery, Scleral Buckle, Submacular Surgery, Transpupillary Thermotherapy, Photosystem I therapy, use of RNA interference (RNAi), extracorporeal rheopheresis (also known as membrane differential filtration and Rheotherapy), microchip implantation, stem cell therapy, gene replacement therapy, ribozyme gene therapy (including gene therapy for hypoxia response element, Oxford Biomedica; Lentipak, Genetix; PDEF gene therapy, GenVec), photoreceptor/retinal cells transplantation (including transplantable retinal epithelial cells, Diacrin, Inc.; retinal cell transplant, Cell Genesys, Inc.), and acupuncture.

Further combinations that may be used to benefit an individual include using genetic testing to determine whether that individual is a carrier of a mutant gene that is known to be correlated with certain ophthalmic conditions. By way of example only, defects in the human ABCA4 gene are thought to be associated with five distinct retinal phenotypes including Stargardt disease, cone-rod dystrophy, age-related macular degeneration and retinitis pigmentosa. See e.g., Allikmets et al., *Science,* 277:1805-07 (1997); Lewis et al., *Am. J. Hum. Genet.,* 64:422-34 (1999); Stone et al., *Nature Genetics,* 20:328-29 (1998); Allikmets, *Am. J Hum. Gen.,* 67:793-799 (2000); Klevering, et al., *Ophthalmology,* 11 1:546-553 (2004). In addition, an autosomal dominant form of Stargardt Disease is caused by mutations in the ELOV4 gene. See Karan, et al., *Proc. Natl. Acad. Sci.* (2005). Patients possessing any of these mutations are expected to find therapeutic and/or prophylactic benefit in the methods described herein.

EXAMPLES

The present invention is further illustrated by the following examples, which should not be construed as limiting in any way.

Example 1

Prevention of High Glucose Induced Injury of Human Retinal Epithelial Cells

The effects of the aromatic-cationic peptides of the invention in preventing high glucose induced injury in human retinal epithelial cells (HREC) were investigated in cultured HRECs.

Methods of HREC culture useful in the studies of the present invention are known. See generally, Li B, Tang S B, Zhang G, Chen J H, Li B J. Culture and characterization of human retinal capillary endothelial cell. *Chin Ophthal Res* 2005; 23: 20-2; Premanand C, Rema M, Sameer M Z, Sujatha M, Balasubramanyam M. Effect of curcumin on proliferation of human retinal endothelial cells under in vitro conditions. *Invest Ophthalmol Vis Sci* 2006; 47: 2179-84.

Briefly, HREC cells were divided into three groups: a normal control group; a group administered 30 mM glucose; and a group administered 30 mM glucose+SS-31. Survival of HRECs in high glucose co-treated with different concentrations of SS-31 (10 nM, 100 nM, 1 µM, 10 µM) was measured using an Annexin V+PI assay and flow cytometry. See generally, Koopman, G., Reutelingsperger, C. P., Kuijten, G. A. M., Keehnen, R. M. J., Pals, S. T., and van Oers, M. H. J. 1994 Annexin V for flow cytometric detection of phosphatidylserine expression on B cells undergoing apoptosis. *Blood* 84: 1415; Homburg, C. H., de Haas, M., von dem Borne, A. E., Verhoeven, A. J., Reutelingsperger, C. P., and Roos, D. 1995. Human neutrophils lose their surface Fc gamma RIII and acquire Annexin V binding sites during apoptosis in vitro. *Blood* 85: 532; Vermes, I., Haanen, C., Steffens-Nakken, H., and Reutelingsperger, C. 1995. A novel assay for apoptosis—flow cytometric detection of phosphatidylserine expression on early apoptotic cells using fluorescein labelled Annexin V. *J. Immunol. Meth.* 184: 39; Fadok, V. A., Voelker, D. R., Campbell, P. A., Cohen, J. J., Bratton, D. L., and Henson, P. M. 1992. Exposure of phosphatidylserine on the surface of apoptotic lymphocytes triggers specific recognition and removal by macrophages. *J. Immunol.* 148: 2207.

Figure 1B:
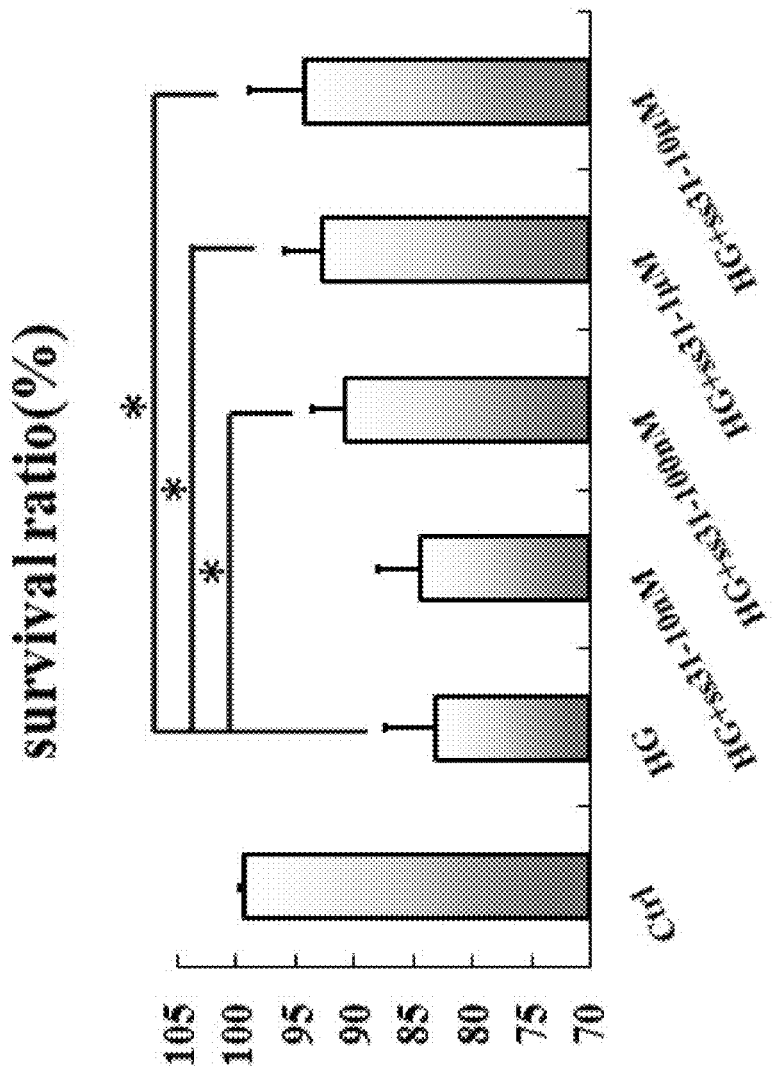
Figure 2:
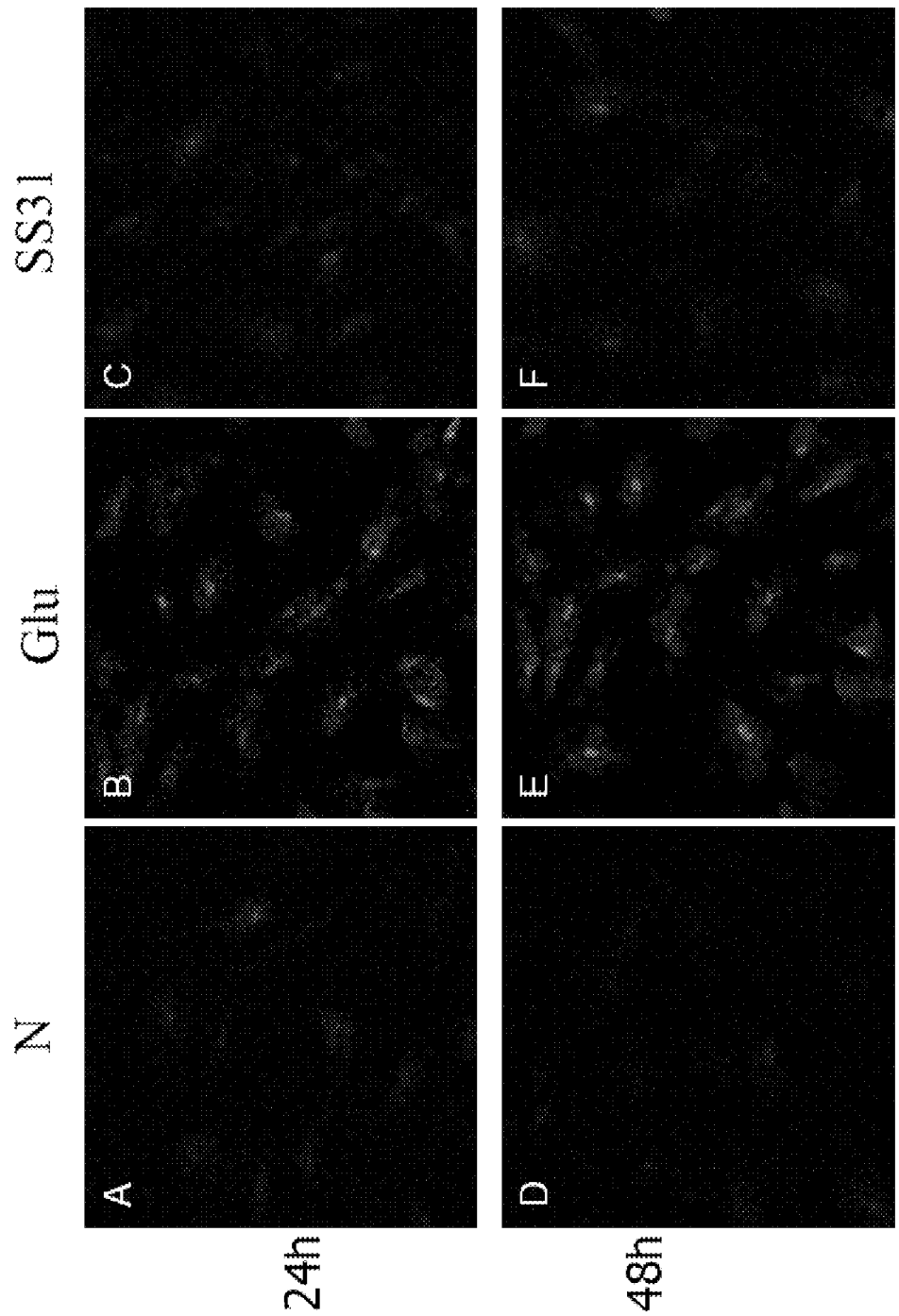
FIGS. 2A-2F is a series of micrographs showing co-treatment with SS-31 reduced intracellular reactive oxygen species (ROS) in HRECs exposed to 30 mM glucose for 24 h and 48 h. Intracellular ROS was measured using dihydroethidium. 2A, 2D normal culture media; 2B, 2E 30 mM glucose; and 2C, 2F 30 mM glucose+SS-31 (100 nM) at 24 and 48 h, respectively.

The survival of HRECs in high glucose co-treated with SS-31 was tested at 24 h and 48 h. The results are shown in FIG. 1 and indicate that survival of HRECs was significantly improved with the administration of SS-31, with a reduction in apoptotic and necrotic cells. The treatment of SS-31 also reduced the production of ROS (FIG. 2).

Assessment of SS-31 as a protectant against mitochondrial potential loss of HRECs treated with high-glucose was examined. To determine if a mitochondrial-mediated pathway was important in SS31's protective effect against high glucose-induced cell death, $\Delta\Psi m$ was measured by flow cytometry. After treating the HRECs with high-glucose without SS31 for 24 or 48 hours, a rapid loss of mitochondrial membrane potential was detected by JC-1 fluorescent probe as indicated by a significant decrease in the ratio of red to green fluorescence observed in the high glucose group. In contrast, $\Delta\Psi m$ in the 100 nM SS31 co-treated group remained virtually unchanged and was comparable to the normal glucose control group (FIG. 3). These data suggest that SS31 prevented the mitochondrial membrane potential loss caused by exposure to a high glucose environment.

Glucose (30 mmol/L) induced cytochrome c release from the mitochondria of HRECs. Fixed HRECs were immunolabeled with a cytochrome c antibody and a mitochondrial specific protein antibody (HSP60). Confocal microscopic analysis showed that HRECs in normal culture and in SS-31 co-treated with glucose have overlapping cytochrome c staining and mitochondria staining, indicating colocalization of cytochrome c and mitochondria (FIG. 4). After treatment with 30 mmol/L glucose for 24 h or 48 h, some cytochrome c was observed in the cytoplasm of HRECs, indicating that glucose induces the release of cytochrome c from the mitochondria to cytoplasm in HREC cells, but SS-31 can decrease such translocation between mitochondria and cytoplasm.

Figure 5:
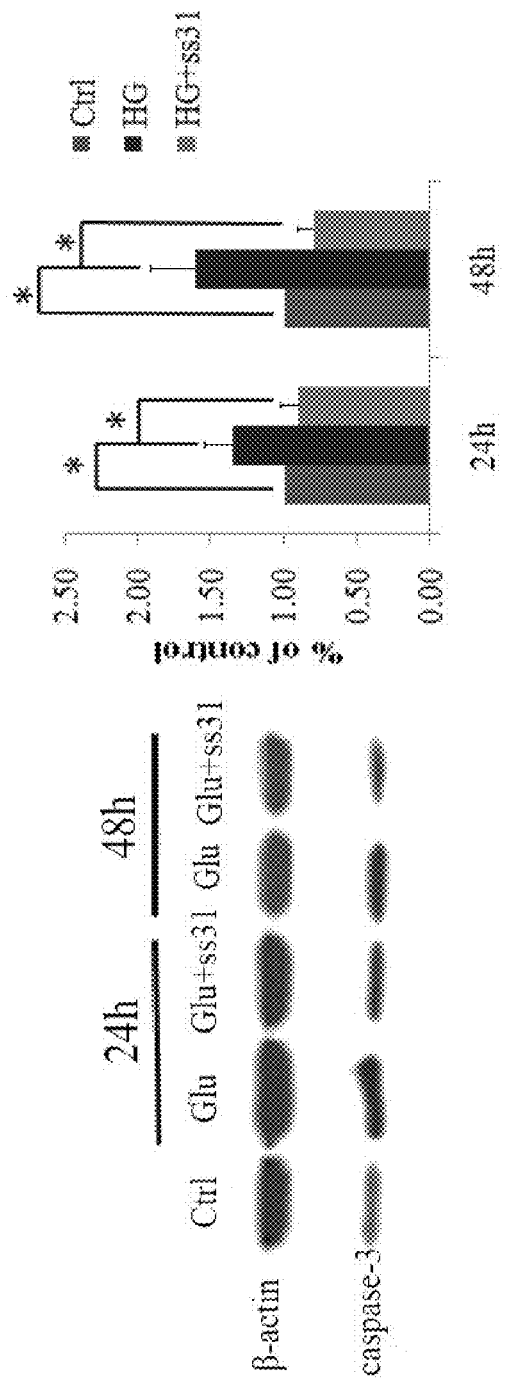
FIG. 5A and FIG. 5B show increased expression of caspase-3 in HRECs treated with high glucose (HG) was reduced by SS-31 co-treatment as detected by western blot. Caspase-3 expression was normalized to the expression of β-actin.
FIGS. 5C-E show SS-31 increases the expression of Trx2 in the high glucose-treated HRECs.
Figure 5:
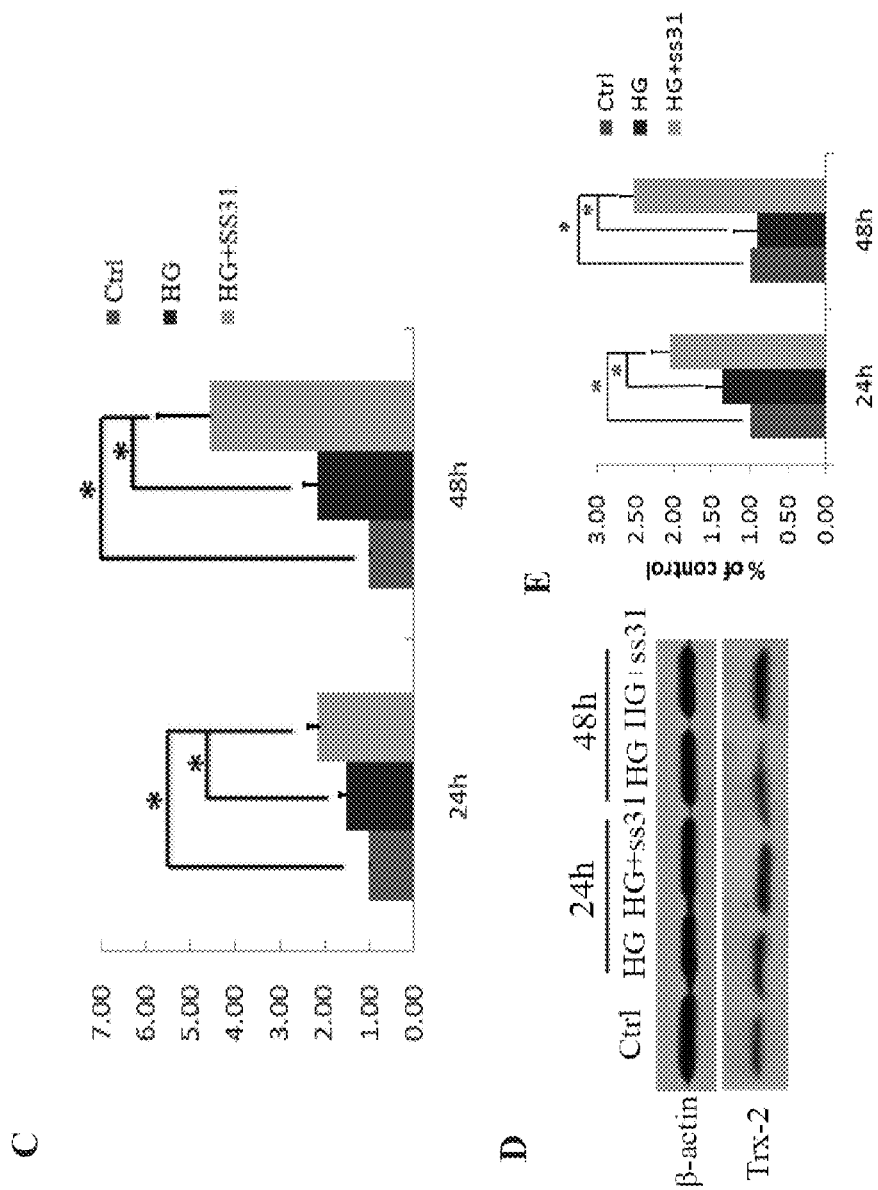

The prevention of cytochrome c release from mitochondria resulted in reduced caspase-3 activity. As shown in FIG. 5, SS-31 decreased the protein expression of caspase-3 in high glucose-treated HRECs. The level of cleaved caspase-3 protein expression was measured by Western blot (FIG. 5A). When HRECs were exposed to 30 mM glucose for 24 h and 48 h, the level of caspase-3 expression increased dramatically. At the same time, in the SS-31 co-treated group, it displayed a marked decrease in the caspase-3 protein level ($*p<0.05$). FIG. 5B shows a quantitative analysis the level of caspase-3 expression of HRECs in high glucose co-treated with SS-31 for 24 and 48 h.

SS-31 increased the expression of Trx2 in the high glucose-treated HRECs. FIG. 5C shows the mRNA level of Trx2 in HRECs exposed to 30 mM glucose co-treated with SS-31 for 24 h and 48 h. The mRNA expression level of Trx2 was measured by quantitative real-time PCR. Relative mRNA levels of Trx2 were normalized by 18S mRNA levels ($*p<0.05$ vs. the normal glucose medium group and the 30 mM high glucose treated group). Three independent samples were used for each time point. FIG. 5D shows the level of Trx2 protein expression as measured by Western blot. The protein expression of Trx2 in the high glucose co-treated with SS-31 group significantly increased comparing to the normal glucose group ($*p<0.05$). FIG. 5E shows quantitative analysis of the protein level of Trx2 in HRECs 24 and 48 h after high glucose without or with SS-31 co-treatment.

These results indicate that SS-31 can promote the survival of HREC cells in a high glucose environment. As such, SS-31 and other aromatic-cationic peptides may be useful in methods for the prevention of diabetic retinopathy.

Example 2

Prevention of Diabetic Retinopathy in Rats Fed a High Fat Diet

The effects of the aromatic-cationic peptides of the invention in preventing the development of diabetic retinopathy were investigated in a Sprague-Dawley rat model. The example describes the results of such experiments.

A rat model of diabetes was established by combination of 6-week HFD and low dose of STZ (30 mg/kg) injection or a single high dose of STZ (65 mg/kg) in SD rats. See generally, K. Srinivasan, B. Viswanad, Lydia Asrat, C. L. Kaul and P. Ramarao, Combination of high-fat diet-fed and low-dose streptozotocin-treated rat: A model for type 2 diabetes and pharmacological screening, *Pharmacological Research*, 52(4): 313-320, 2005. Rats of the same batch fed with normal chow (NRC) were used as a control. Tables 7-10 show the therapeutic schedule and experimental protocol.

TABLE 7

Treatment Groups - HFD/STZ Model

| Group | Number of Rats | Model | Treatment | Dosage and Route |
|---|---|---|---|---|
| A | 12 | HFD/STZ | SS-31 | 10 mg/kg s.c |
| B | 12 | HFD/STZ | SS-31 | 3 mg/kg s.c. |
| C | 12 | HFD/STZ | SS-31 | 1 mg/kg s.c. |
| D | 10 | HFD/STZ | SS-20 | 10 mg/kg s.c. |
| E | 10 | HFD/STZ | SS-20 | 3 mg/kg s.c. |
| F | 10 | HFD/STZ | Saline | Equal vol. s.c. |
| G | 10 | NRC | Saline | Equal vol. s.c. |

TABLE 8

Therapeutic Schedule - HFD/STZ Model

| Duration | Objective | Diabetic Groups (A, B, C, D, E, F) | Control Group (G) |
|---|---|---|---|
| $1^{st}$ Week | Acclimation | Normal rat chow | |
| $2^{nd}$-$7^{th}$ Week | Diet Manipulation | High Fat Diet | Normal Rat Chow |
| End of $7^{th}$ Week | STZ Injection | STZ 30 mg/kg, i.p., once | Citrate buffer |
| $8^{th}$-$27^{th}$ Week | Induction of Diabetes | High fat diet until $21^{st}$ week, then switched to normal rat chow | Normal rat chow |
| $28^{th}$-$37^{th}$ Week | Peptide Treatment | Peptide treatment (see Table 7) | Group G: 2 mL/kg, s.c. |
| $38^{th}$ Week | Collected 24 h urine and blood samples, and harvested vital organs | | |

TABLE 9

Treatment Groups -STZ Model

| Group | Number of Rats | Model | Treatment | Dosage and Route |
|---|---|---|---|---|
| A | 11 | Diabetes | SS-31 | 10 mg/kg s.c |
| B | 11 | Diabetes | SS-20 | 10 mg/kg s.c. |
| C | 10 | Diabetes | Saline | Equal vol. s.c. |
| D | 10 | Normal | Saline | Equal vol. s.c. |

TABLE 10

Therapeutic Schedule -STZ Model

| Duration | Objective | Diabetic Groups (A, B, C) | Control Group (D) |
|---|---|---|---|
| $1^{st}$-$3^{rd}$ Week | Acclimation | Normal rat chow | |
| End of $3^{rd}$ Week | STZ Injection | STZ 30 mg/kg, i.p., once | Citrate buffer |
| $4^{th}$-$18^{th}$ Week | Induction of Diabetic Complications | Normal Rat Chow | |
| $19^{h}$-$28^{th}$ Week | Peptide Treatment | Peptide treatment (see Table 9) | Group D: 2 mL/kg, s.c. |
| $29^{th}$ Week | Collected 24 h urine and blood samples, and harvested vital organs | | |

Figure 6:
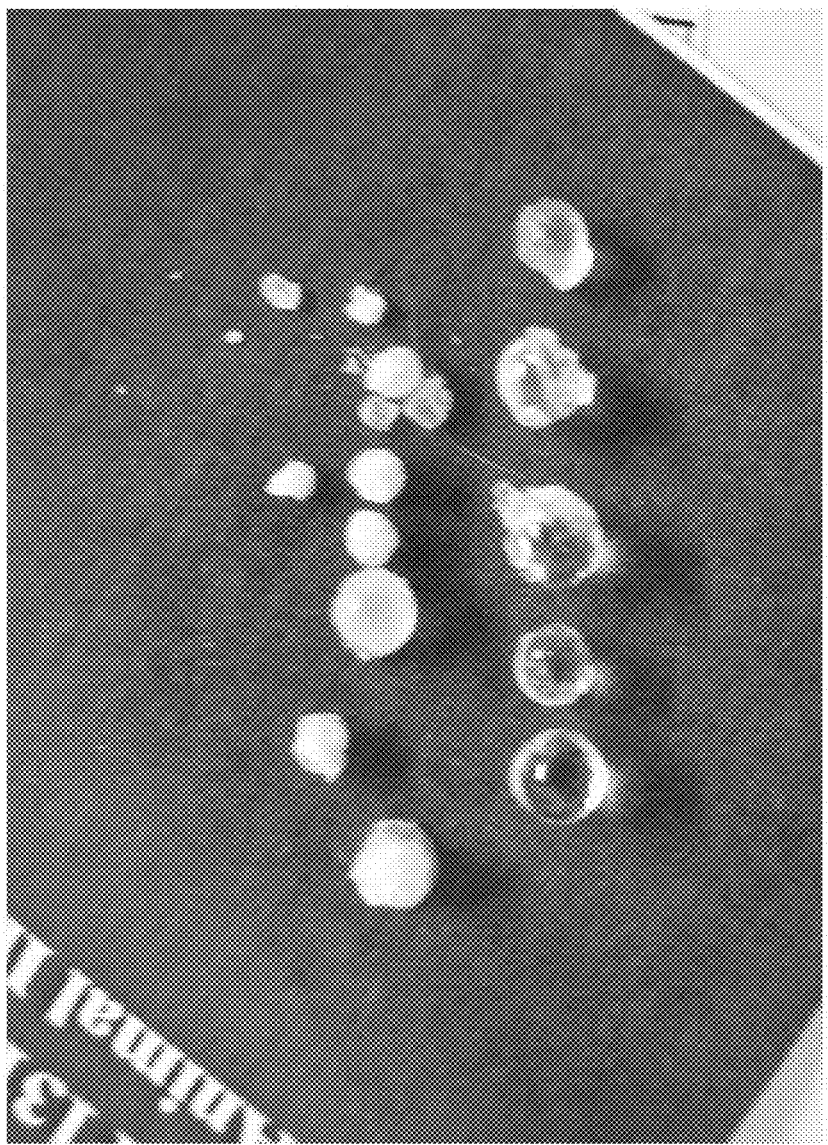
FIG. 6 is a photograph of the effects of SS-31 on the lenses of diabetic rats. Top row: lenses obtained from diabetic rats; bottom row: lenses obtained from diabetic rats treated with SS-31 or SS-20.
Figure 7:
FIG. 7 is a series of photographs showing the effects of SS-31 and SS-20 on the lenses of diabetic rats. Diabetes was induced by high fat diet and streptozotocin (HFD/STZ) (top row) or streptozotocin (STZ) alone (bottom row).

In accordance with the experimental protocol just described, the effects of the aromatic-cationic peptides in treating conditions associated with diabetes in a SD rat model were demonstrated. Administration of SS-20 and SS-31 resulted in a prevention or reversal of cataract formation in the lenses of diabetic rats (FIGS. 6 and 7, Tables 11 and 12).

TABLE 11

HFD/STZ Rat Model

| Group | Turbidity degree | | | | | Percentage of opacity (%) | Percentage of severe opacity (%) |
|---|---|---|---|---|---|---|---|
| | − | + | ++ | +++ | ++++ | | |
| NRC | 4 | 0 | 0 | 0 | 0 | 0 | 0 |
| HFD/STZ | 1 | 0 | 2 | 3 | 0 | 83.3 | 0 |
| SS20 3 mg | 1 | 1 | 1 | 0 | 1 | 75.0 | 25.0 |
| SS20 10 mg | 1 | 2 | 1 | 0 | 0 | 75.0 | 0 |
| SS31 1 mg | 1 | 1 | 1 | 0 | 0 | 67.7 | 0 |
| SS31 3 mg | 3 | 1 | 0 | 0 | 1 | 20.0 | 20.0 |
| SS31 10 mg | 6 | 1 | 0 | 0 | 0 | 14.3 | 0 |

−: transparent;
+: mildly opaque;
++: opaque;
+++: moderately opaque;
++++: severely opaque

TABLE 12

STZ Rat Model

| Group | Opacity degree | | | | | Percentage of opacity (%) | Percentage of severe opacity (%) |
|---|---|---|---|---|---|---|---|
| | − | + | ++ | +++ | ++++ | | |
| NRC | 6 | 0 | 0 | 0 | 0 | 0 | 0 |
| STZ | 1 | 0 | 0 | 1 | 3 | 80.0 | 60.0 |
| SS20 10 mg | 2 | 0 | 2 | 0 | 1 | 60.0 | 20.0 |
| SS31 10 mg | 2 | 2 | 0 | 0 | 1 | 60.0 | 20.0 |

Figure 8:
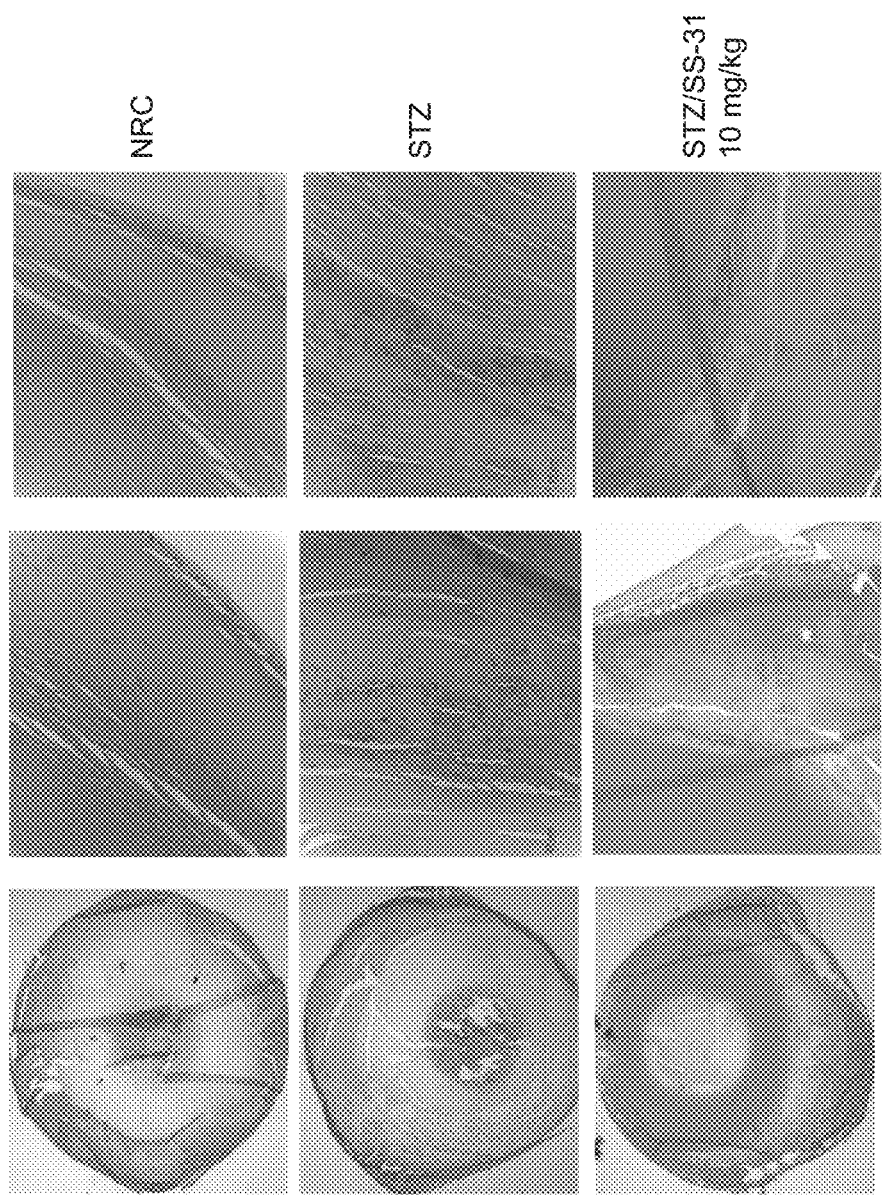
FIG. 8 is a series of micrographs showing the lens epithelium from normal rats, diabetic rats, and diabetic rats treated with SS-31. Diabetes was induced by STZ.
Figure 9:
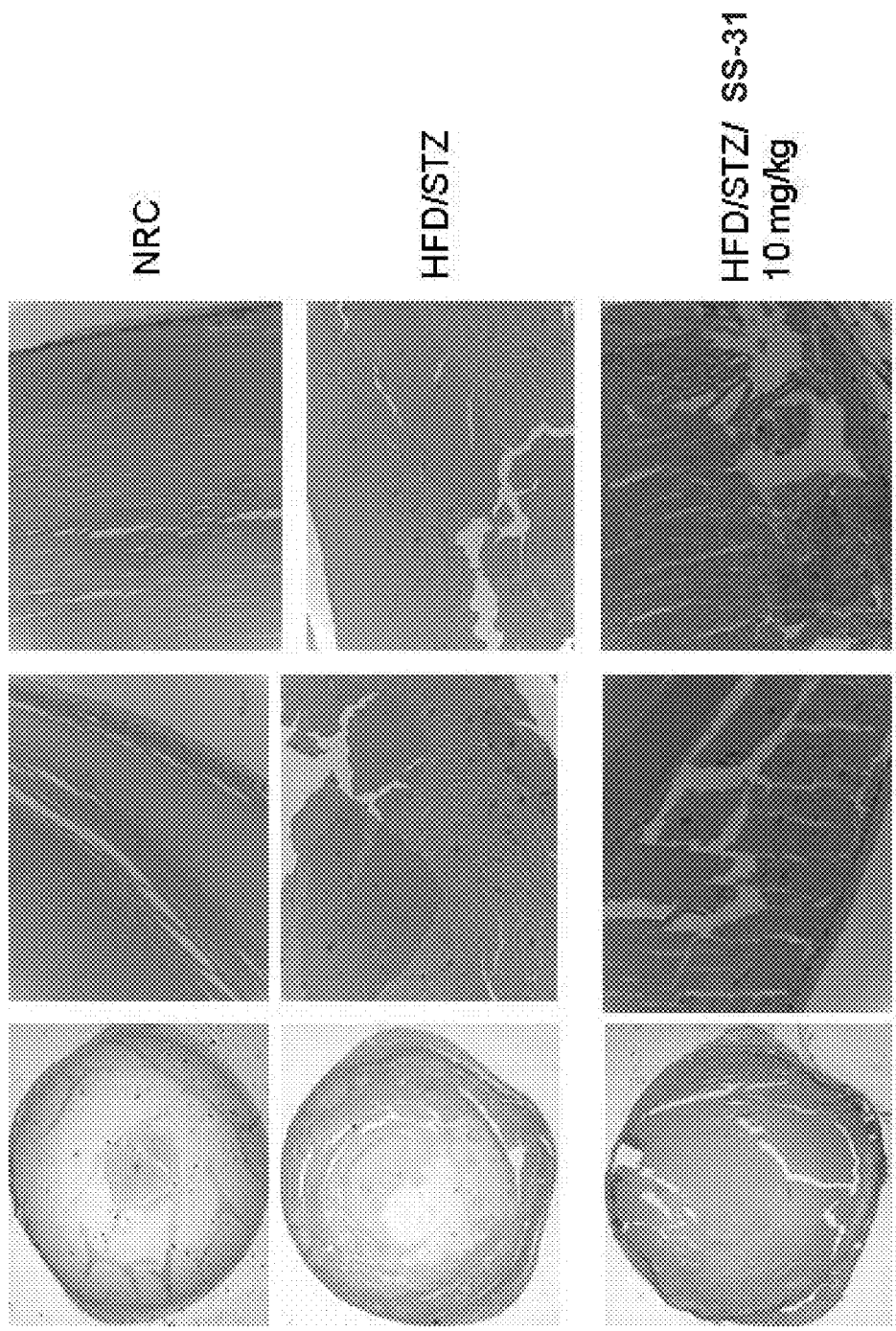
FIG. 9 is a series of micrographs showing the lens epithelium from normal rats, diabetic rats, and diabetic rats treated with SS-31. Diabetes was induced by HFD/STZ.

The effect of the aromatic cationic peptides on lens epithelium in the SD rat model was investigated. Administration of SS-31 reduced epithelial cellular changes in both STZ rat model (FIG. 8) and HFD/STZ rat model (FIG. 9).

Figure 10:
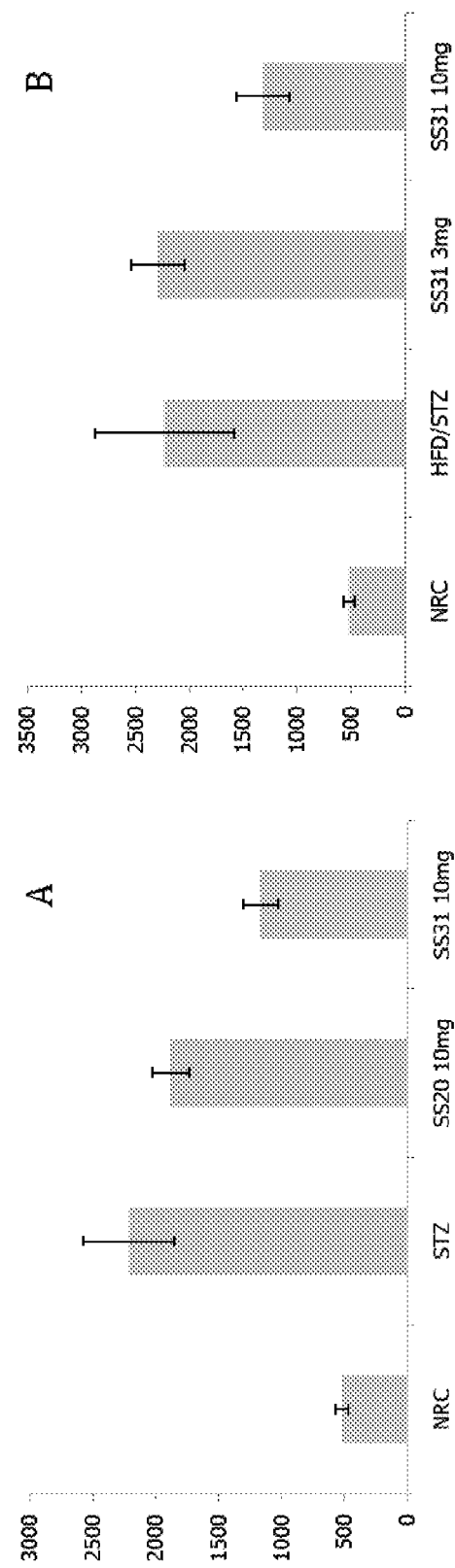
FIG. 10 is a series of charts showing the integrity of the blood-retinal barrier of normal rats (NRC), diabetic rats, and diabetic rats treated with SS-20 or SS-31, as analyzed by Evans blue extravasation. (A) diabetes induced by STZ; (B) diabetes induced by HFD/STZ.

The effect of the aromatic-cationic peptides on the inner blood-retinal barrier function in the SD rat model was investigated. Administration of SS-20 and SS-31 resulted in improved inner blood-retinal barrier function compared to rats on a HFD not administered SS-20 or SS-31 (FIG. 10).

Figure 11:
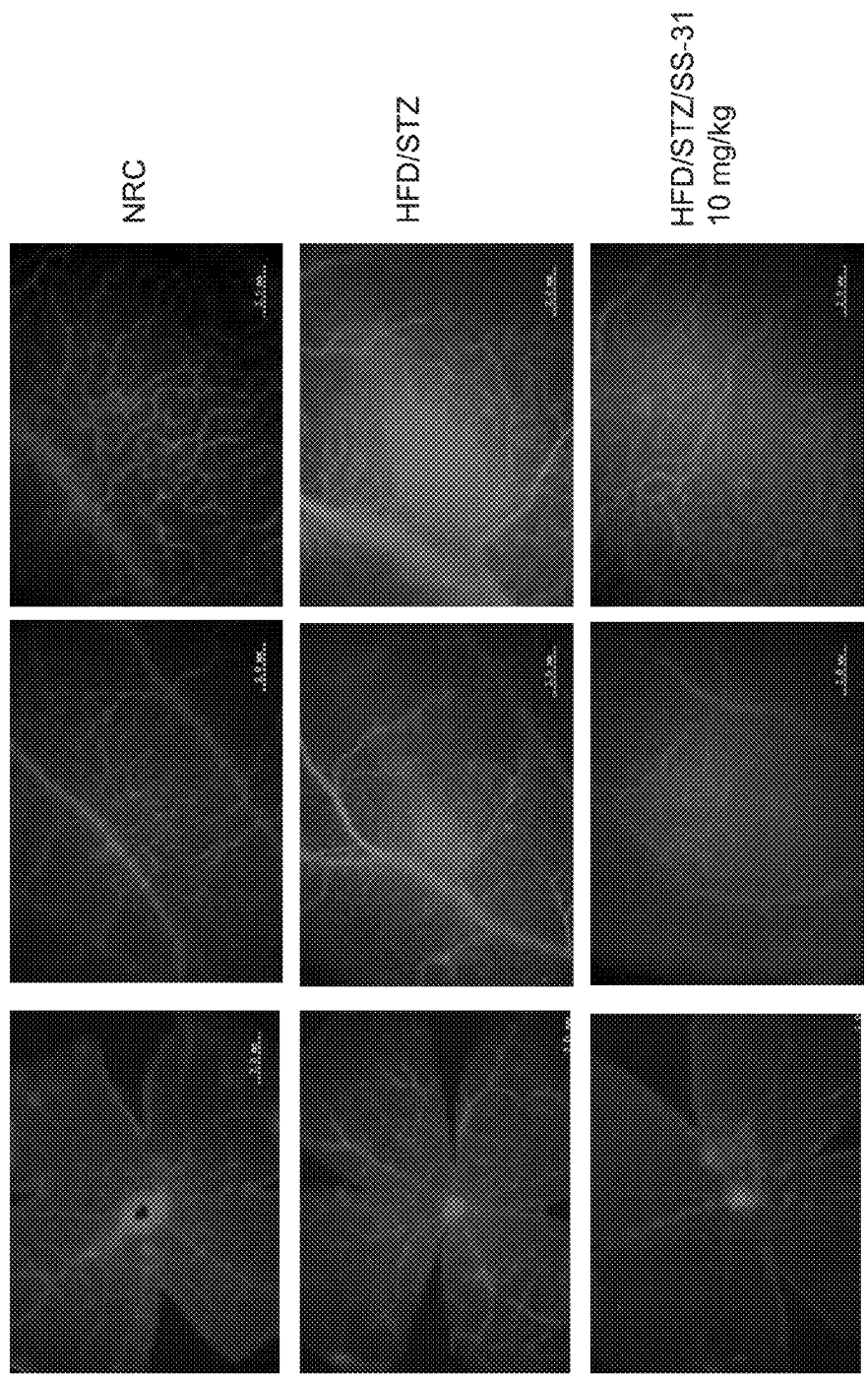
FIG. 11 is a series of micrographs showing retinal microvessels of normal rats (NRC), diabetic rats (HFD/STZ), and diabetic rats treated with SS-31.
Figure 12:
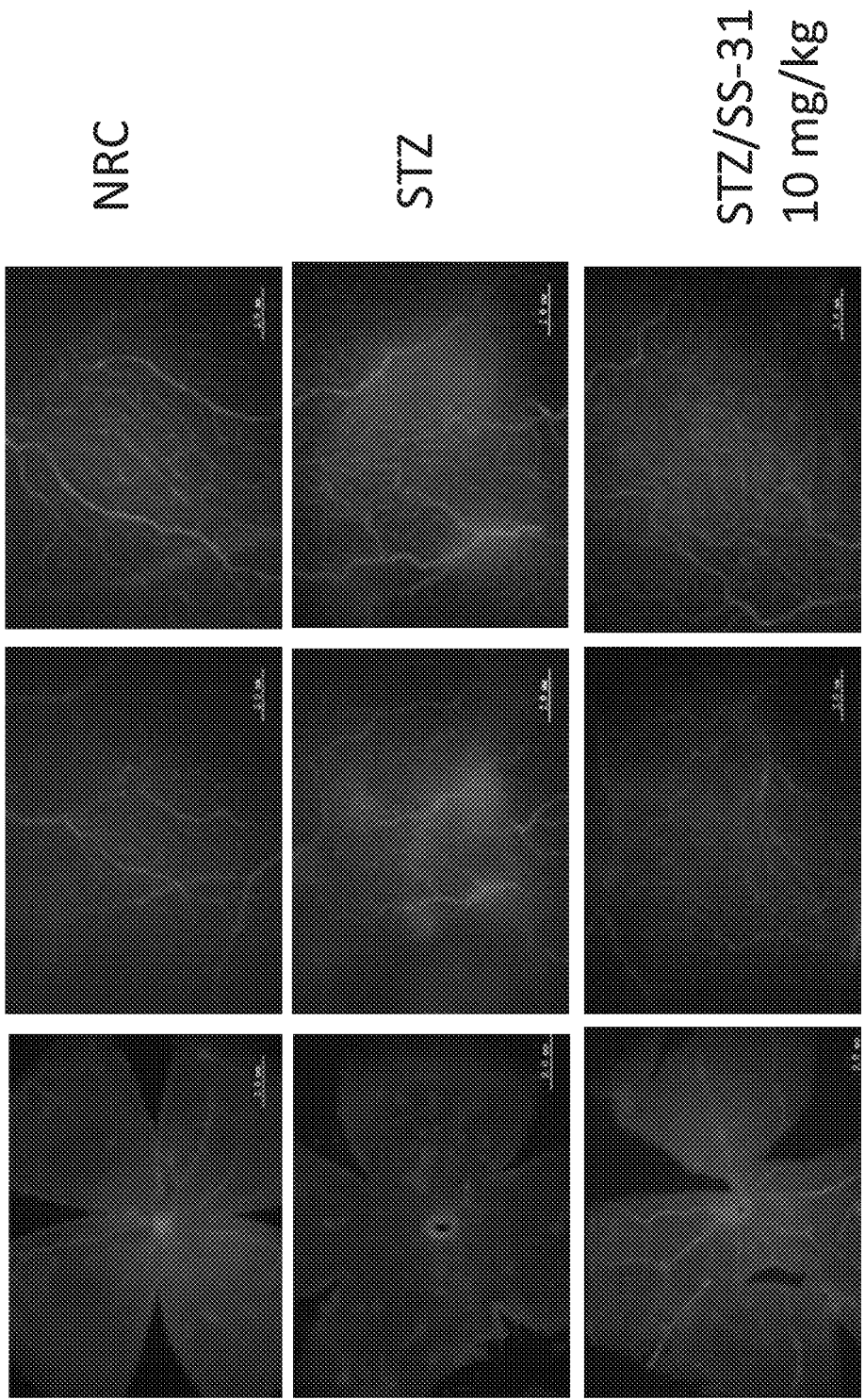
FIG. 12 is a series of micrographs showing retinal microvessels of normal rats, diabetic rats (STZ), and diabetic rats treated with SS-31.

The effect of the aromatic-cationic peptides on retinal microvessels in the SD rat model was investigated (FIGS. 11-12). Administration of SS-31 reduced retinal microvasular changes observed in STZ or HFD/STZ rats.

Figure 13:
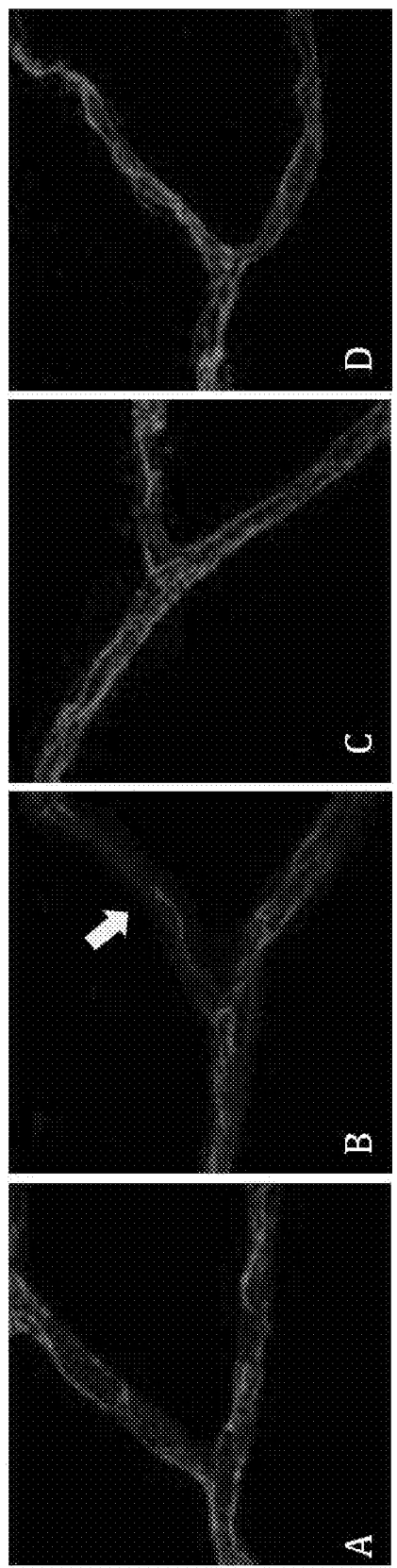
FIGS. 13A-13D is a series of micrographs showing the distribution of the tight junction protein claudin-5 in retinal microvessels in normal rats (A), STZ rats (B), STZ/SS-20-treated rats (C), or STZ/SS-31-treated rats (D).

The effect of the aromatic-cationic peptides on the distribution of tight junction protein claudin-5 in retinal microvessels in the SD rat model was investigated. Distribution of tight junction protein claudin-5 was detected under a confocal microscope (FIG. 13). Claudin-5 was distributed along the retinal vessels smoothly, linearly, and uniformly in normal rats (A), but the linear shape was broken in the STZ rat (B, arrow). Distribution of claudin-5 on retinal vessels in STZ rats treated with SS-20 (10 mg/kg) or SS-31 (10 mg/kg) was similar to that of normal rat (Panels C and D, respectively).

In summary, these findings collectively establish that aromatic-cationic peptides, either prevent or compensate for the negative effects of diabetes in the eye, e.g., cataracts and microvasculature. As such, administration of the aromatic-cationic peptides of the present invention is useful in methods of preventing or treating ophthalmic conditions associated with diabetes in human subjects.

Example 3

SS-31 Prevents Oxidative Stress in Glaucomatous Trabecular Meshwork Cells

The effects of the aromatic-cationic peptides of the invention in preventing or treating glaucoma were investigated by studying the effects of the peptides in glaucomatous trabecular meshwork cells. Glaucoma is the second leading cause of irreversible blindness worldwide. Primary open-angle glaucoma (POAG) is the major subtype of glaucoma. In POAG, there is no visible abnormality of the trabecular meshwork. However, it is believed that the ability of the cells in the trabecular meshwork to carry out their normal function is impaired.

Figure 18:
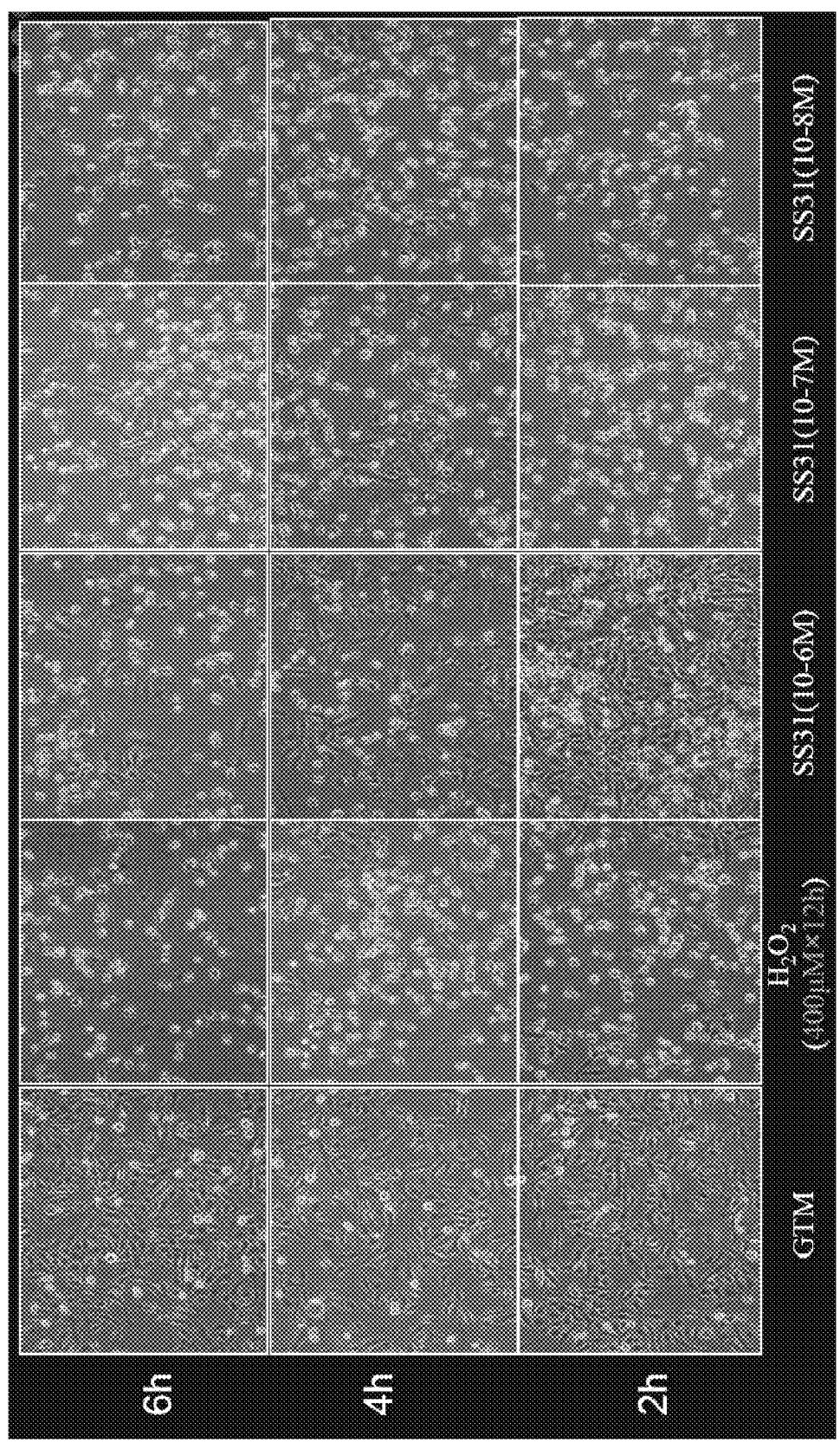
FIG. 18 is a series of micrographs showing the morphology changes in GTM cells in response to SS-31 treatment as viewed using inverted phase contrast microscopy.

In this Example, the effects of the aromatic-cationic peptides of the invention were compared between trabecular meshwork cells from POAG patients (GTM) and trabecular meshwork cells from non-diseased individuals (HTM). Methods useful in the studies of the present invention have been described. See generally, He Y, Ge J, Tombran-Tink J., Mitochondrial defects and dysfunction in calcium regulation in glaucomatous trabecular meshwork cells. *Invest Ophthalmol Vis Sci.* 2008, 49(11):4912-22; He Y, Leung K W, Zhang Y H, Duan S, Zhong X F, Jiang R Z, Peng Z, Tombran-Tink J, Ge J. Mitochondrial complex I defect induces ROS release and degeneration in trabecular meshwork cells of POAG patients: protection by antioxidants. *Invest Ophthalmol Vis Sci.* 2008, 49(4):1447-58. GTM cells show a significant impairment of mitochondrial membrane potential compared to HTM cells (FIG. 18).

The cells were divided into three groups: "Group A" cells were exposed to hydrogen peroxide prior to administration of SS-31. "Group B" cells were exposed to SS-31 prior to administration of hydrogen peroxide. "Group C" cells were administered SS-31 and hydrogen peroxide simultaneously.

Figure 14:
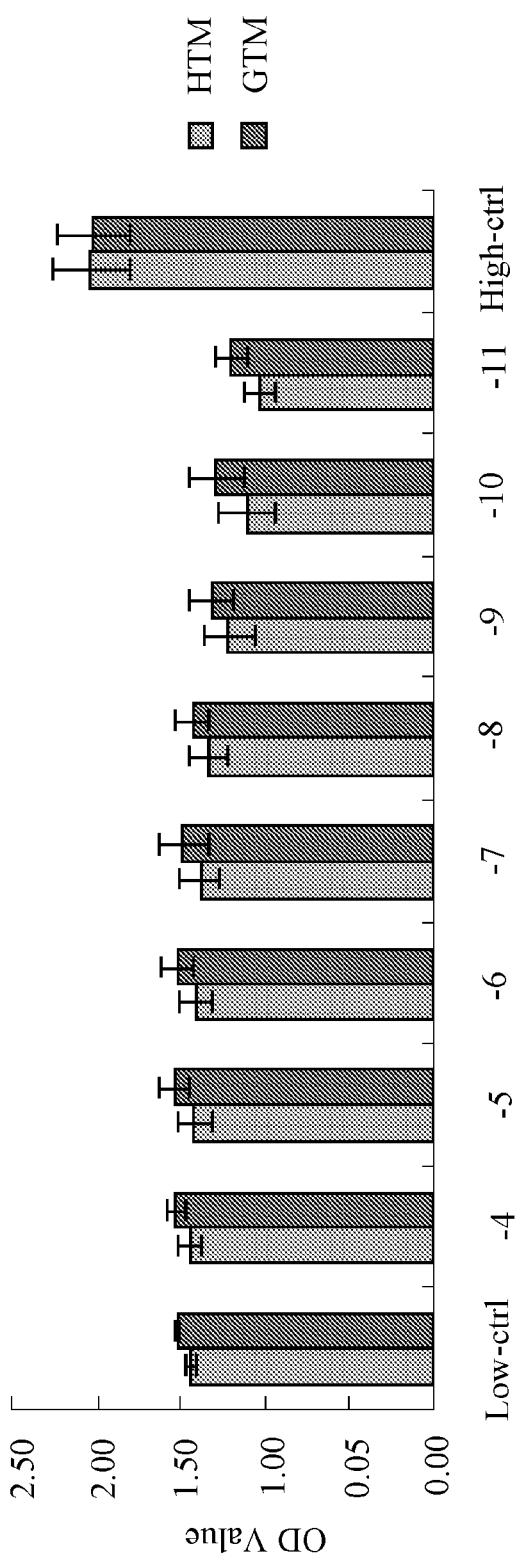
FIG. 14 is a chart showing the lack of cytotoxicity of SS-31 on trabecular meshwork cells from non-diseased individuals (HTM) and trabecular meshwork cells from glaucoma patients (GTM) administered SS-31.

To assess whether SS-31 had cytotoxic effects of HTM or GTM cells, various concentrations of SS-31 were administered to cells and the cytotoxicity was measured using an LDH assay. A LDH cytotoxicity assay is a colorimetric method of assaying cellular cytotoxicity. The assay quantitatively measures the stable, cytosolic, lactate dehydrogenase (LDH) enzyme, which is released from damaged cells. The released LDH is measured with a coupled enzymatic reaction that results in the conversion of a tetrazolium salt (iodonitrotetrazolium (INT)) into a red color formazan by diaphorase. Methods to detect LDH from cells useful in the studies of the present invention are known. See generally, Haslam, G. et al. (2005) *Anal. Biochem.* 336: 187; Tarnawski, A. (2005) *Biochem. Biophys. Res. Comm.* 333: 207; Round, J. L et al. (2005) *J. Exp. Med.* 201: 419; Bose, C. et al. (2005) *Am. J. Physiol. Gastr. L.* 289: G926; Chen, A. and Xu, J. (2005) *Am. J. Physiol. Gastr. L.* 288: G447. The LDH activity is determined as NADH oxidation or INT reduction over a defined time period. The results are shown in FIG. 14 and indicate that SS-31 does not affect the viability of HTM and GTM cells.

Figure 16:
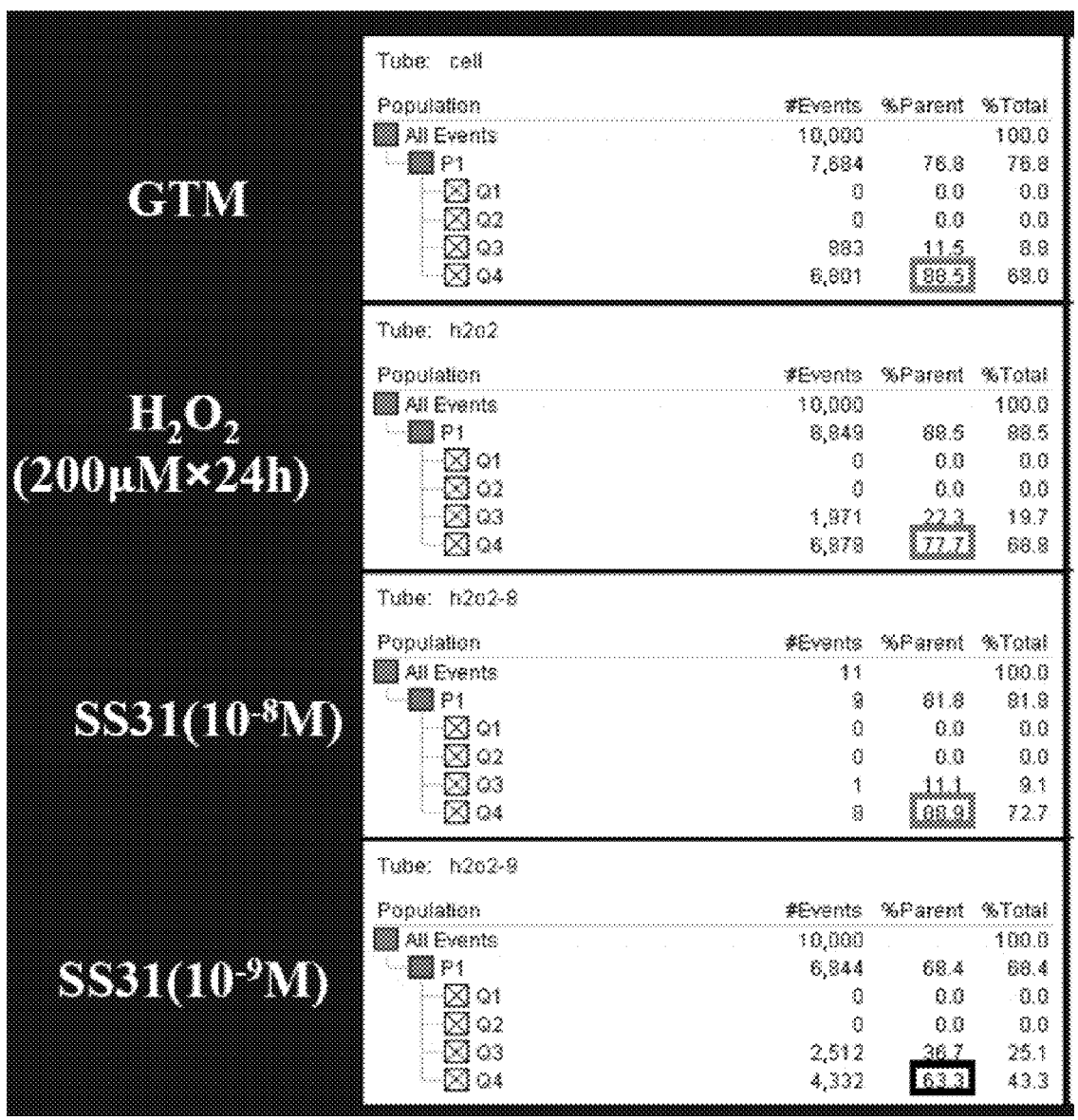
FIG. 16 is a series of charts showing co-treatment with SS-31 inhibited the decrease in mitochondrial membrane potential ($\Delta\psi m$), as measured by TMRM and flow cytometry, in trabecular meshwork cells from glaucoma patients (GTM) induced by 200 $\mu M$ $H_2O_2$.
Figure 16:
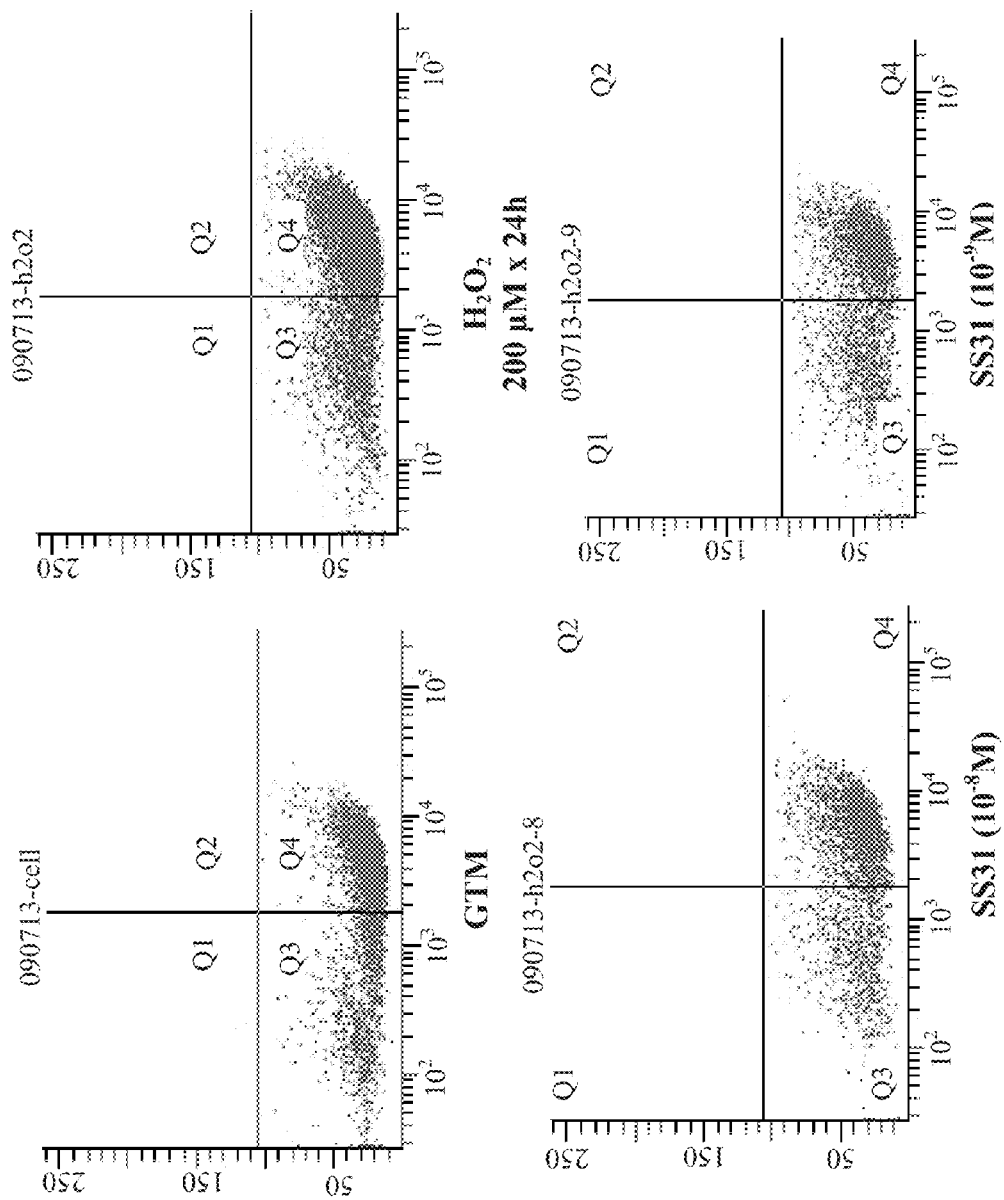

Methods to measure mitochondrial membrane potential using TMRM useful in the studies of the present invention have been described by Andrea Rasola and Massimo Geuna, A flow cytometry assay simultaneously detects independent apoptotic parameters, *Cytometry* 45:151-157, 2001; Mitoprobe™ JC-1 Kit for Flow Cytometry, Molecular Probes, Invitrogen, USA. FIG. 16 shows the results in GTM cells. Collectively, these results establish that treatment with SS-31 improves the mitochondrial membrane potential of cells that were exposed to hydrogen peroxide prior to administration of SS-31.

Group A.

Figure 15:
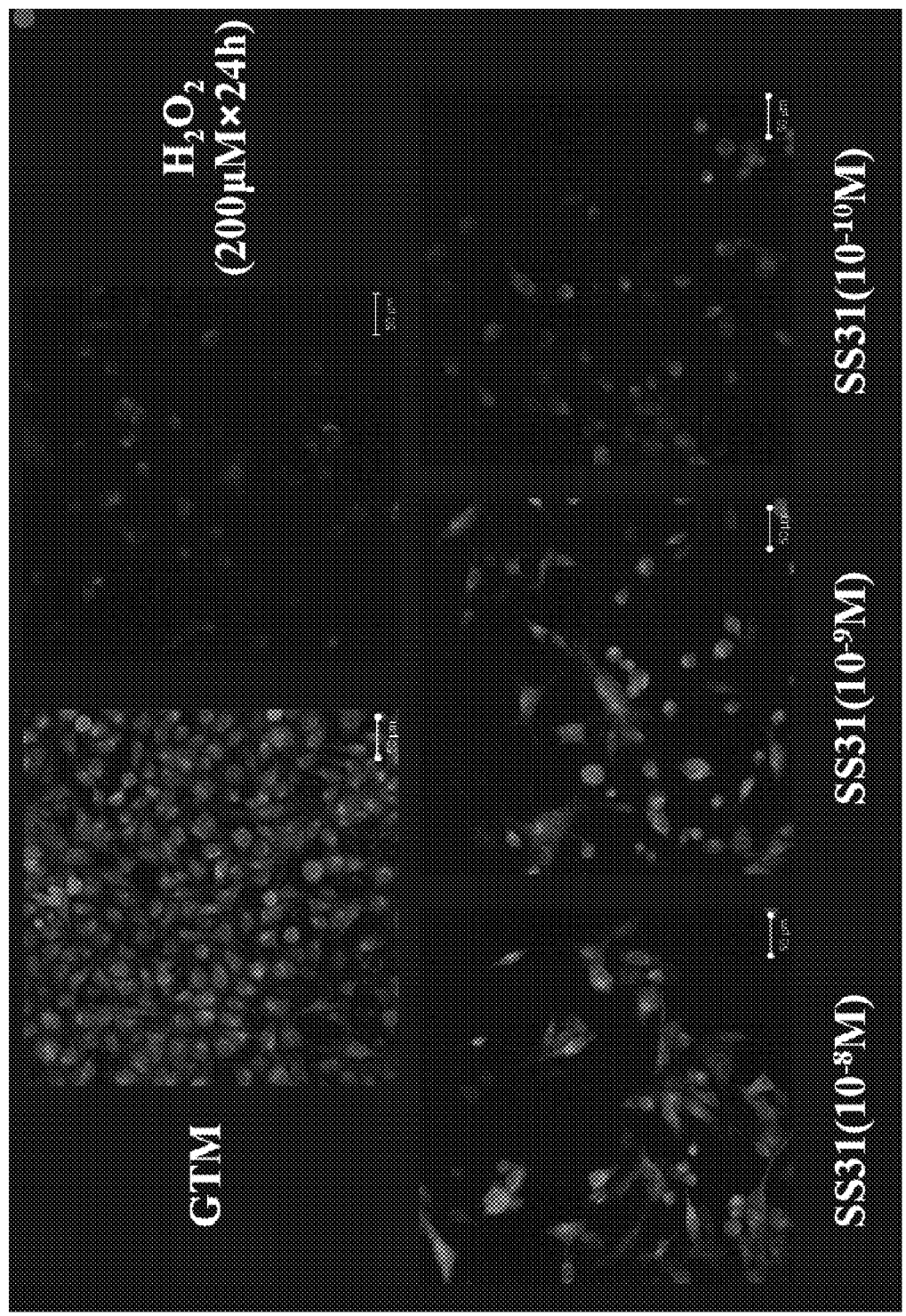
FIG. 15 is a series of confocal micrographs showing co-treatment with SS-31 dose-dependently inhibited the decrease in mitochondrial potential ($\Delta\psi m$) elicited by 200 $\mu M$ $H_2O_2$ in trabecular meshwork cells from glaucoma patients (GTM).
Figure 17:
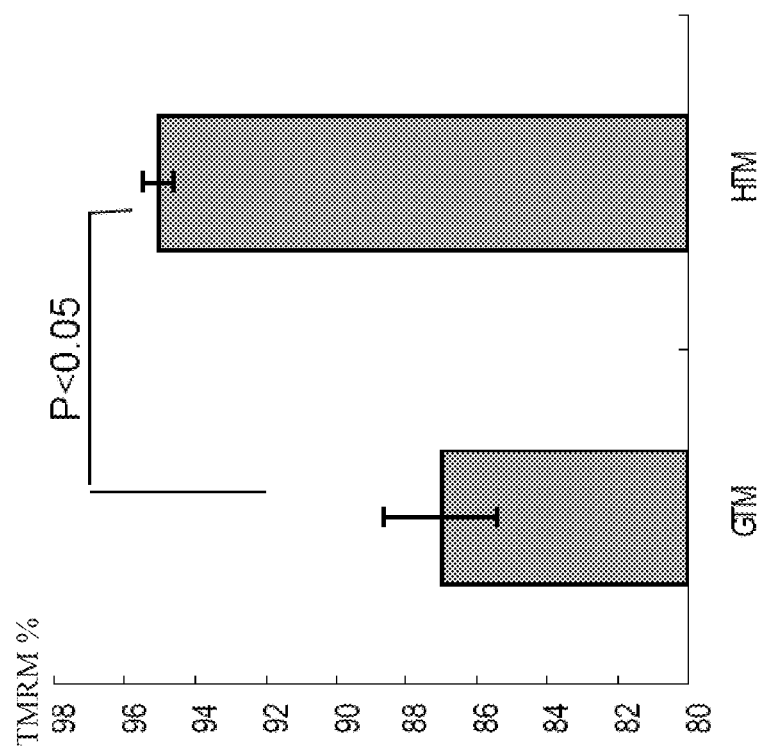
FIG. 17 is a chart comparing mitochondrial membrane potential ($\Delta\psi m$) in GTM and HTM cells.

The mitochondrial membrane potential (Δψm) of HTM and GTM cells was investigated when those cells were exposed to hydrogen peroxide prior to administration of SS-31. First, the mitochondrial membrane potential was measured using confocal microscopy of cells labeled with tetramethylrhodamine methyl ester (TMRM, 500 nM×30 min) (FIG. 15). The mitochondrial membrane potential was also measured using flow cytometry (FIGS. 16-17) by labeling cells with the mitochondrion-selective probe tetramethylrhodamine methyl ester (TMRM, 500 nM×30 min).

Group B.

Figure 19:
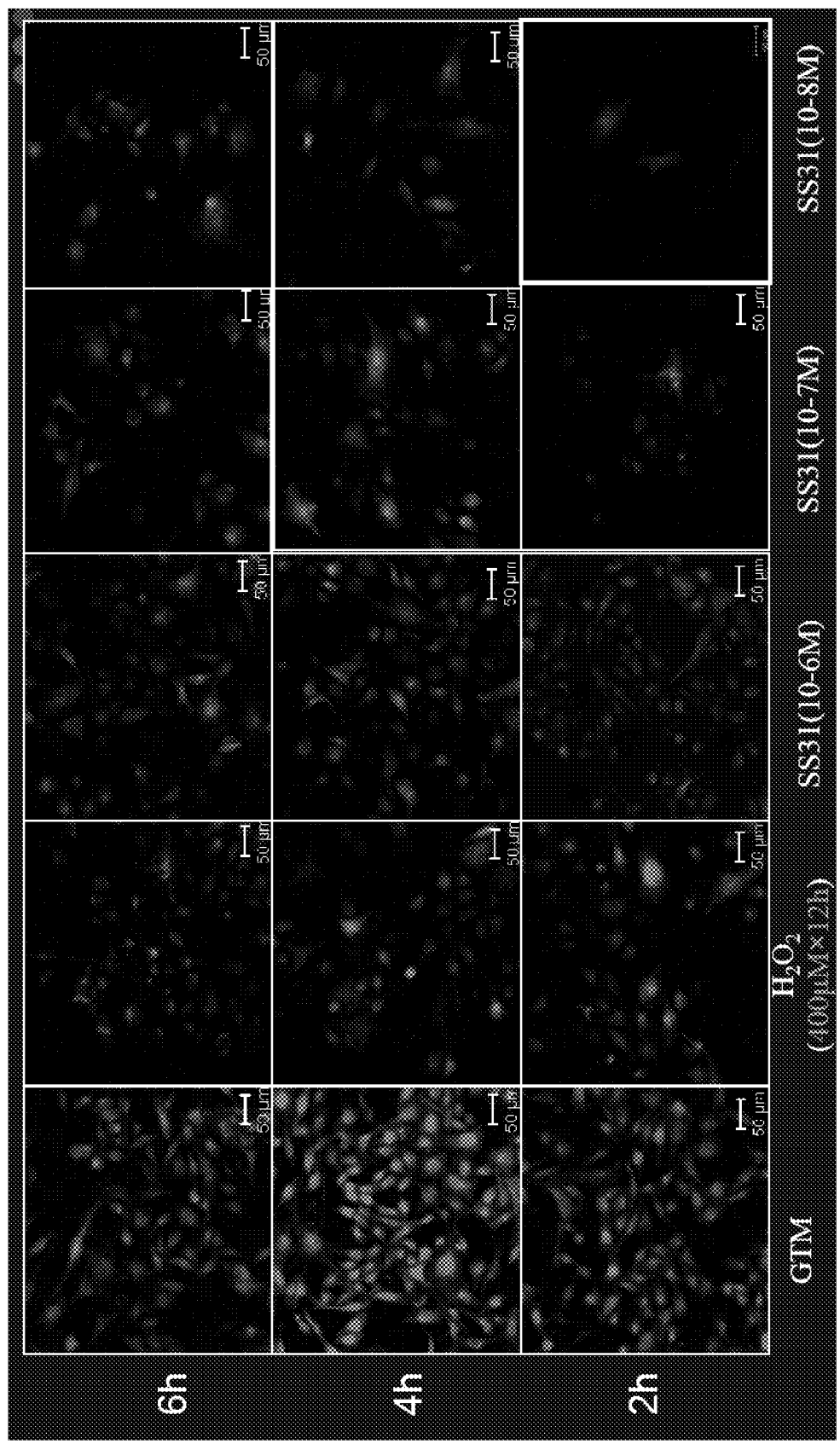
FIG. 19 is a series of micrographs showing co-treatment with SS-31 reduced the loss of mitochondrial membrane potential in GTM cells caused by 400 $\mu M$ $H_2O_2$ in a dose-dependent manner as viewed using confocal microscopy.
Figure 20:
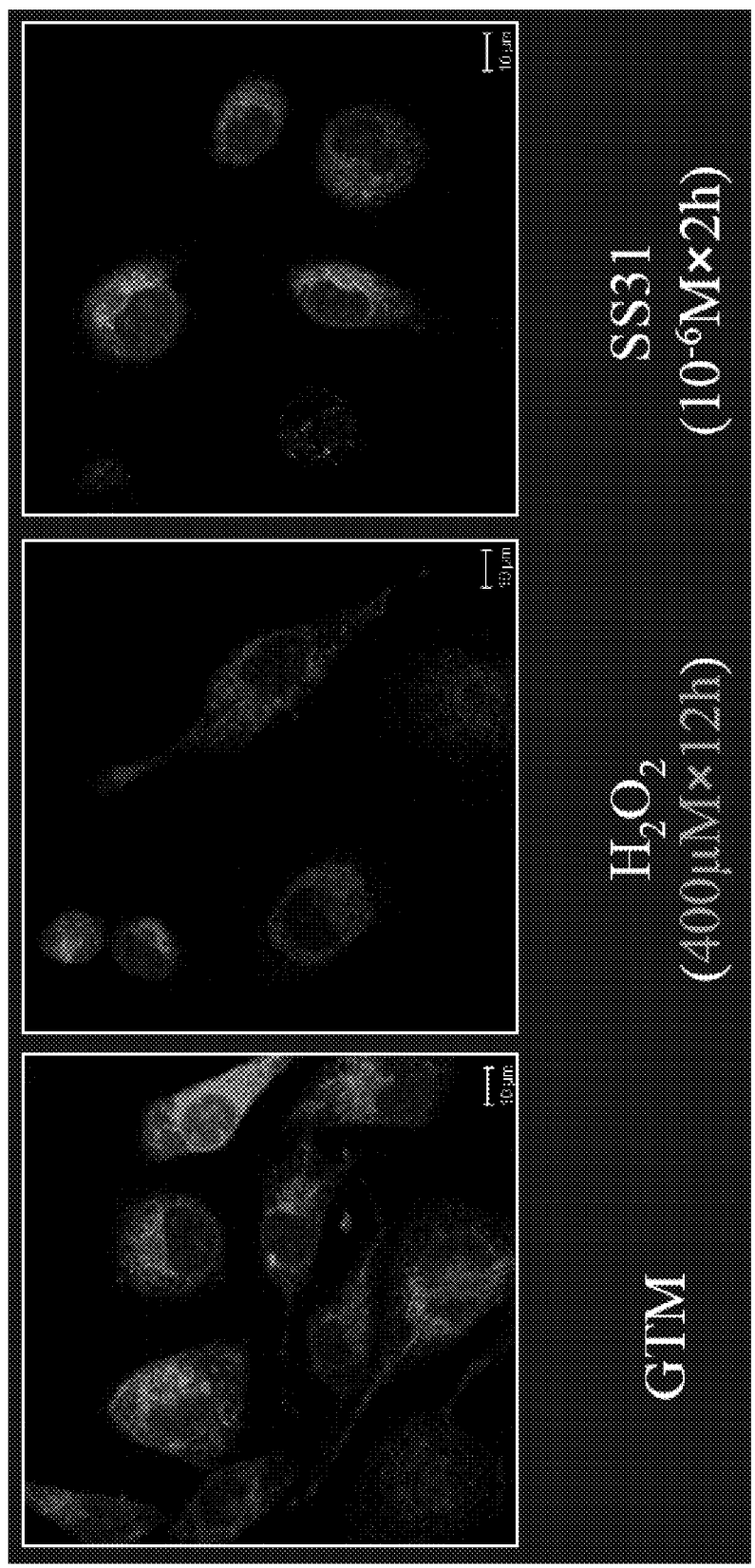
FIG. 20 is a series of micrographs showing co-treatment with SS-31 reduced the loss of mitochondrial membrane potential ($\Delta\psi m$) in GTM cells caused by 400 $\mu M$ $H_2O_2$ as viewed by TMRM and confocal microscopy (200× magnification).
Figure 21:
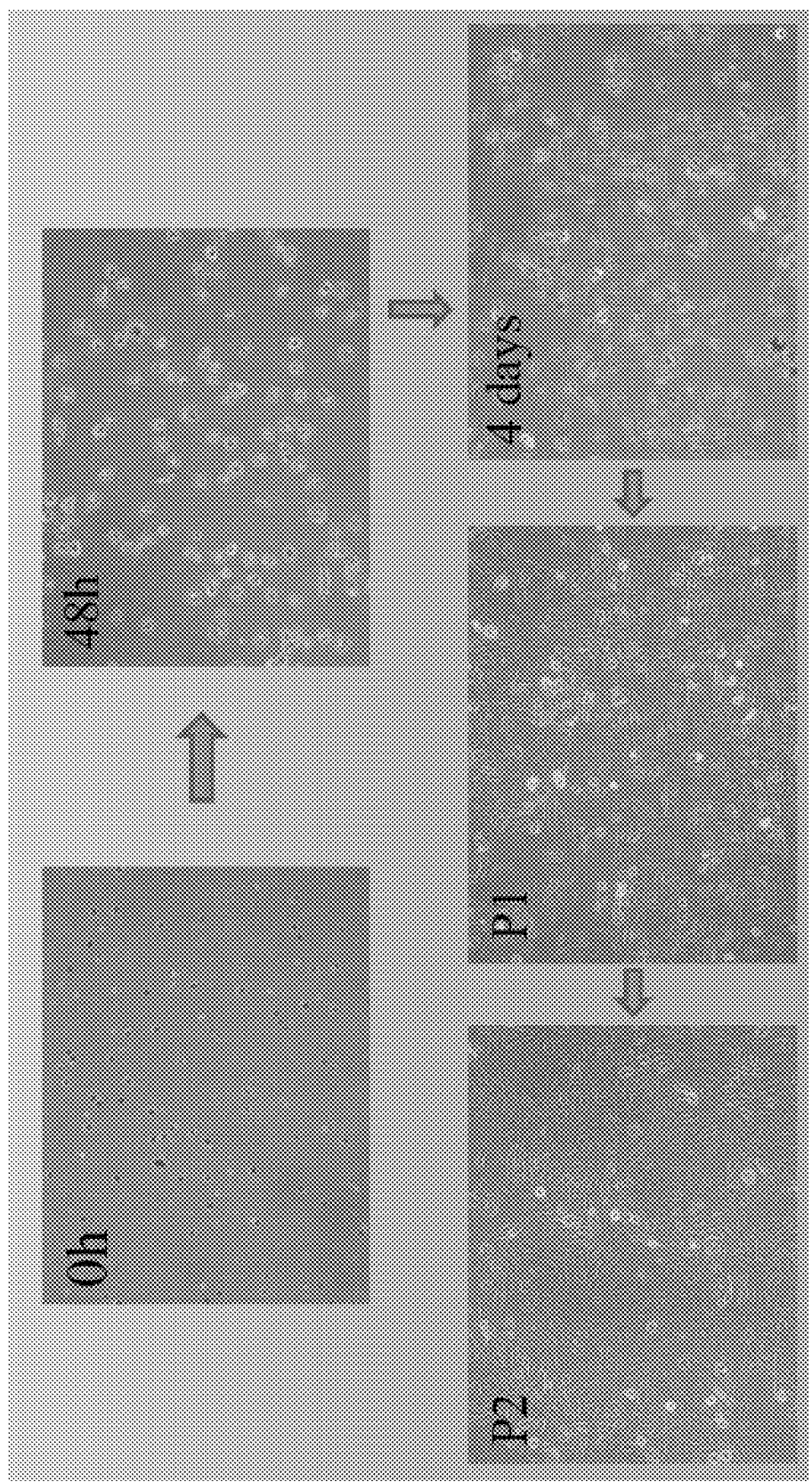
FIG. 21 is a series of micrographs showing the morphology changes in GTM cells in response to SS-31 treatment as viewed using inverted phase contrast microscopy.

The morphology of GTM cells was investigated when those cells were exposed to SS-31 prior to administration of hydrogen peroxide. FIG. 18 shows the results of inverted phase contrast microscopy of cells administered various concentrations of SS-31. The results indicate that SS-31 protects cells from hydrogen peroxide-mediated morphlogical changes in a concentration-dependent and time-dependent manner. That is, hydrogen peroxide mediated cell loss and rounding was diminished in cells exposed to SS-31 peptide. The mitochondrial membrane potential (Δψm) of HTM and GTM cells was also investigated when those cells were exposed to SS-31 prior to administration of hydrogen peroxide. The mitochondrial membrane potential was measured using confocal microscopy of cells labeled with tetramethylrhodamine methyl ester (TMRM, 500 nM×30 min) (FIG. 19-21). These results show that pre-treatment with SS-31 dose-dependently improves the mitochondrial membrane potential of cells that were exposed to hydrogen peroxide. As such, SS-31 provides a protective effect against oxidative stress in GTM cells.

Figure 36:
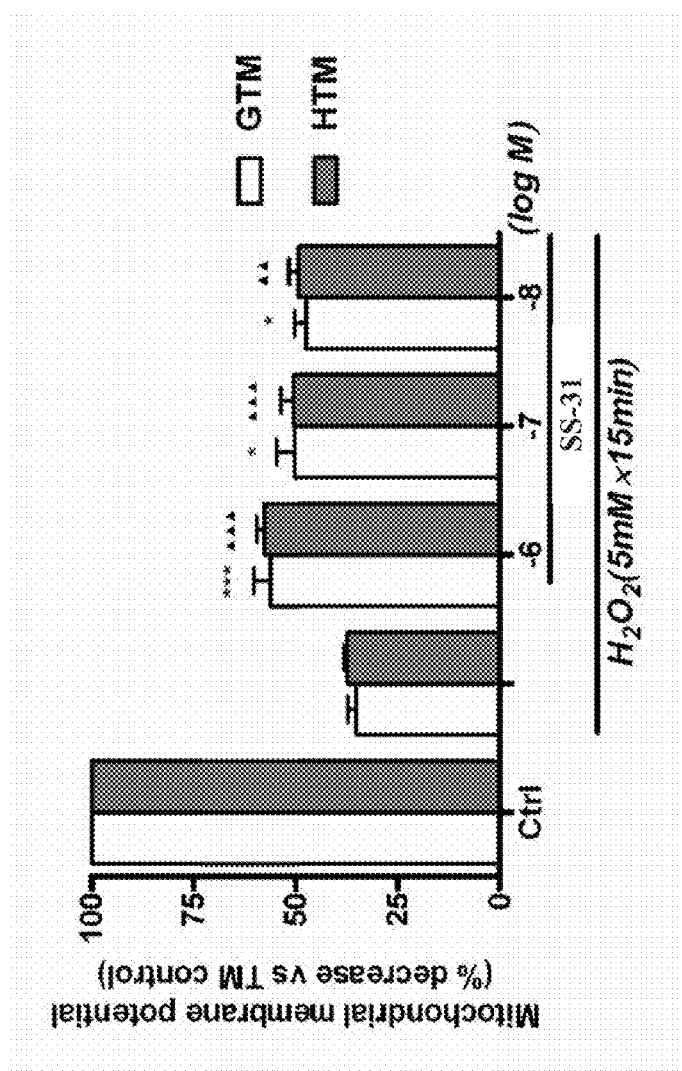
FIG. 36 is a graph showing the fluorescence intensity of TMRM of GTM and HTM cells in control and SS-31-treated groups, as measured using FACS analysis.

The effects of SS-31 at mitigating acute oxidative injury in GTM and HTM cells was investigated. FIG. 36 shows the fluorescence intensity of TMRM of GTM and HTM cells using FACS analysis. The percentage of fluorescence intensity compared to GTM control in $H_2O_2$, SS-31 $10^{-6}$M, SS-31 $10^{-7}$M, SS-31 $10^{-8}$M were 35.2±2.12%, 56.2±4.04%, 50.3±4.46%, 47.5±2.82% respectively, n=4; the HTM groups were 37.4±0.725%, 57.7±1.80%, 50.6±3.06%, 49.4±2.27% respectively, n=4. ** means P<0.01 compared to GTM $H_2O_2$ group; * means P<0.05 compared to GTM $H_2O_2$ group; ▲▲▲ means P<0.001 compared to HTM $H_2O_2$ group.

Figure 37:
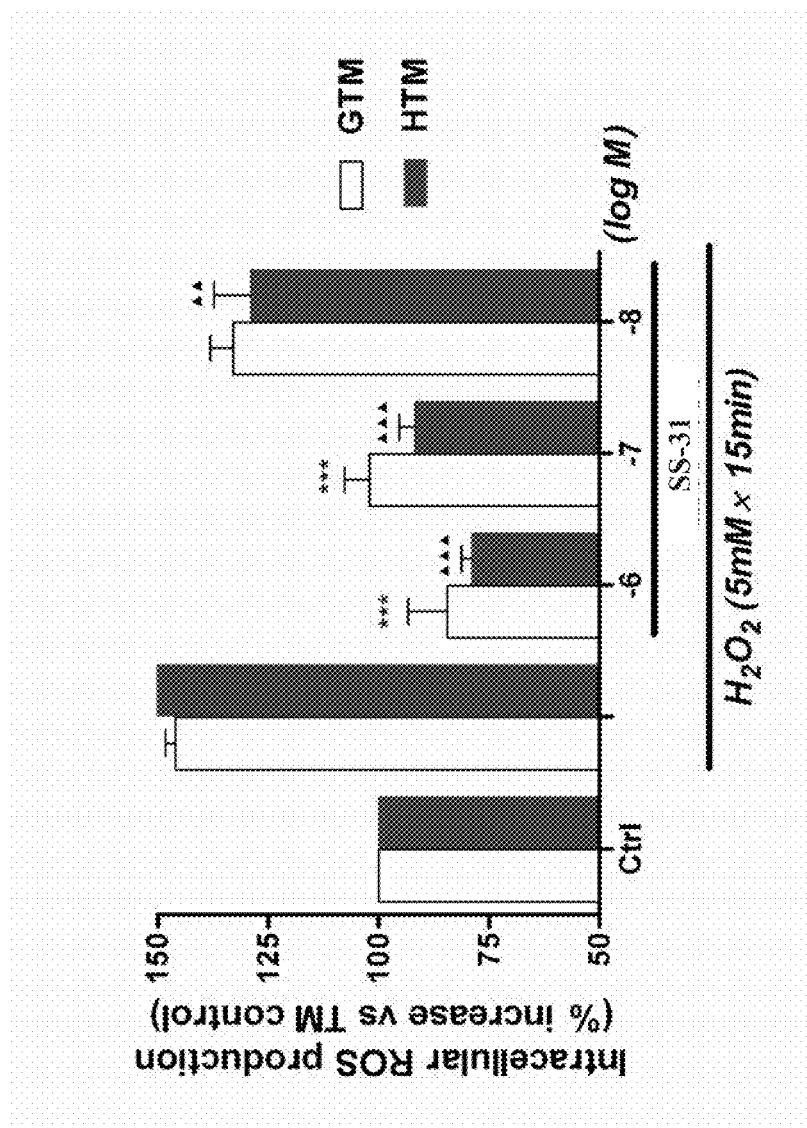
FIG. 37 is a graph showing the fluorescence intensity of ROS of GTM and HTM cells in control and SS-31-treated groups, as measured using FACS analysis.
Figure 38:
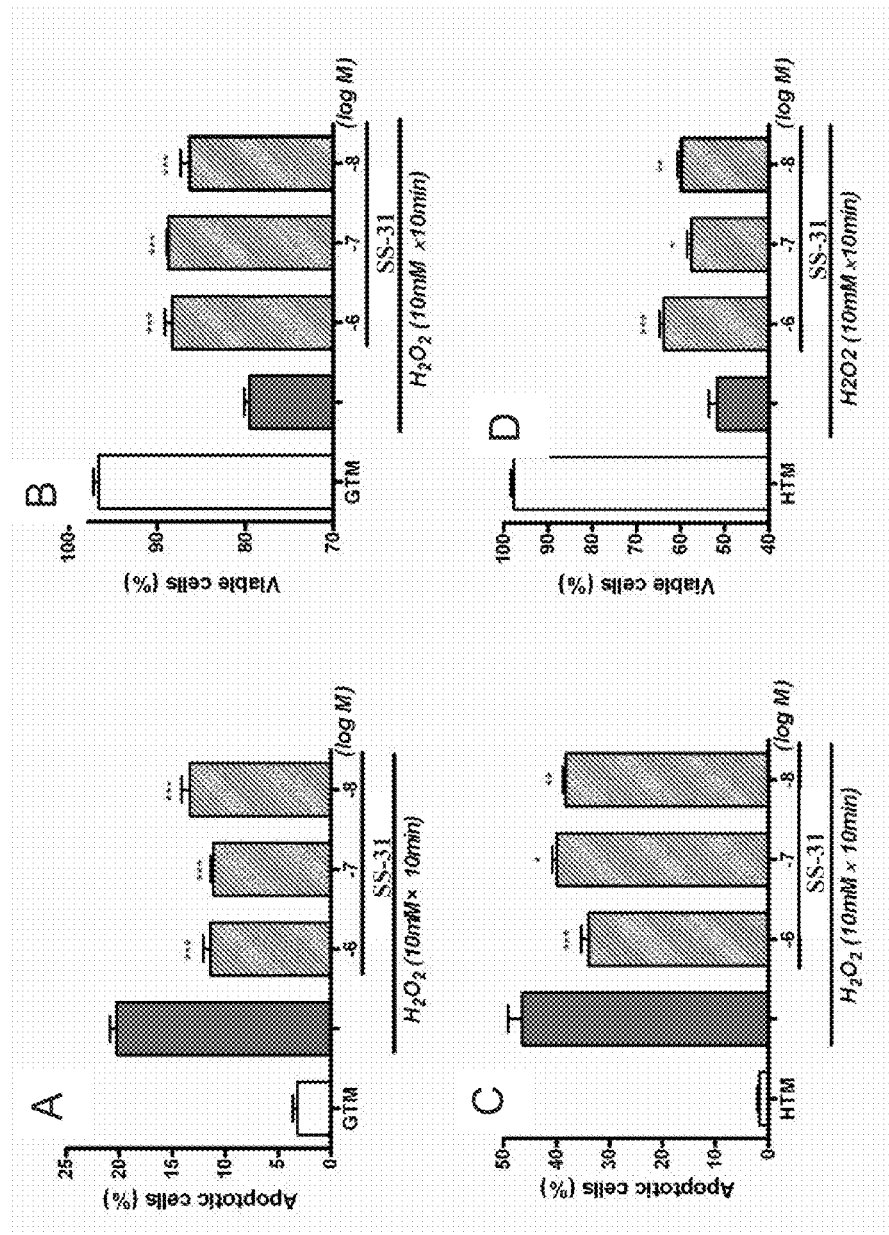
FIG. 38 is a series of graphs showing cell apoptosis of control and SS-31-treated groups valued by percentage of cells in the Q2+Q4 quadrant.

FIG. 37 shows the fluorescence intensity of ROS of GTM and HTM cells in control and SS-31-treated groups using FACS analysis. The percentage of intracellular ROS production compared to GTM control in GTM $H_2O_2$, SS-31 $10^{-6}$M, SS-31 $10^{-7}$M, SS-31 $10^{-8}$M groups were 146.0±2.27%, 84.5±8.75%, 102.0±5.69%, 133.0±5.17% respectively (n=3); the HTM groups were 153.0±3.46%, 79±2.39%, 91.8±3.49%, 129.0±8.24% respectively (n=4). P<0.001 GTM and HTM $H_2O_2$ Group compared to control; *** means P<0.001 compared to GTM $H_2O_2$ group; ▲▲▲ Means P<0.001 compared to HTM $H_2O_2$ group; ▲▲ means P<0.01 compared to HTM $H_2O_2$ group. FIG. 38 shows that SS-31 reduced the amount of cell apoptosis induced by $H_2O_2$.

Figure 39:
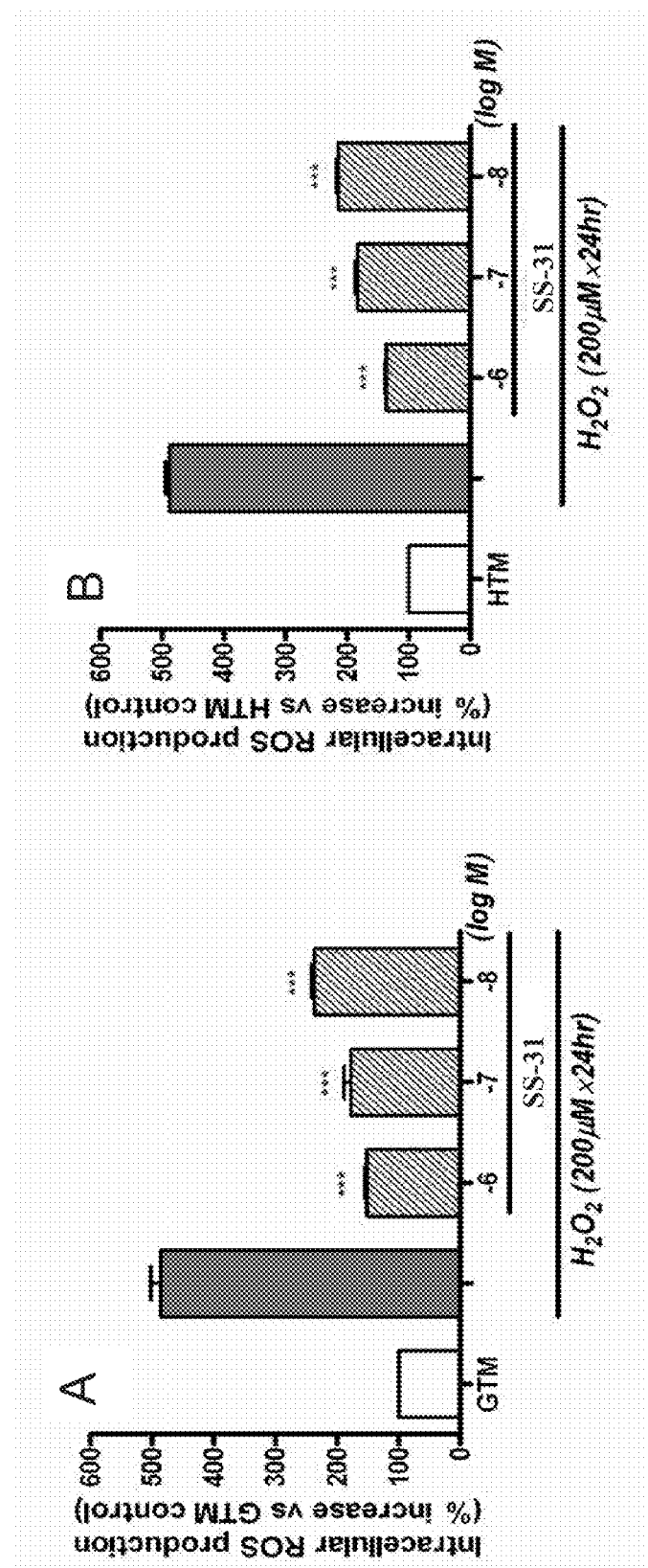
FIG. 39 is a series of graphs showing that SS-31 reduced intracellular ROS production in GTM3 and iHTM cells treated with $H_2O_2$.

The effects of SS-31 on sustained oxidative injury of GTM and HTM cells was examined. Cells were pre-treated with $10^{-6}$, $10^{-7}$, $10^{-8}$ M of SS-31 for 1 h, and then incubated with 200 μM $H_2O_2$ for 24 h to investigate the protective effect of SS-31 in sustained oxidative stress. FIG. 39 and Table 13 shows the effects of SS-31 on ROS production from sustained oxidative injury of GTM and HTM cells. FIG. 40 and Table 14 shows the MMP change in GTM and HTM cells in each treatment group.

TABLE 13

ROS Production in GTM3 and iHTM cells treated with $H_2O_2$.

|  | $H_2O_2$-Ctrl (%) | SS-31 1 μM (%) | SS-31 0.1 μM (%) | SS-31 0.01 μM (%) |
|---|---|---|---|---|
| GTM3 | 376.80 ± 17.47 | 47.40 ± 1.81*** | 68.91 ± 8.62*** | 133.70 ± 3.24*** |
| iHTM | 388.50 ± 5.54 | 36.91 ± 1.47*** | 82.89 ± 3.70*** | 114.30 ± 3.89*** |

TABLE 14

MMP Decline in GTM3 and iHTM cells treated with $H_2O_2$.

|  | H2O2-Ctrl (%) | SS-31 1 μM (%) | SS-31 0.1 μM (%) | SS-31 0.01 μM (%) |
|---|---|---|---|---|
| GTM3 | −39.67 ± 2.33 | −24.33 ± 4.18* | −29.33 ± 2.19* | −31.33 ± 1.20* |
| iHTM | −69.53 ± 2.01 | −44.99 ± 2.19*** | −53.24 ± 2.52** | −58.24 ± 2.62* |

Collectively, these results demonstrate that SS-31 has no cytotoxicity at $10^{-4}$M for both GTM and HTM cells and that sustained and acute oxidative stress induced by hydrogen peroxide can be prevented by SS-31 (>$10^{-9}$ M). As such, the aromatic-cationic peptides of the present invention are useful in methods of preventing or treating glaucoma in human subjects.

Example 4

SS-31 Prevents Oxidative Stress in Primary Retinal Pigment Epithelial Cells

Figure 22:
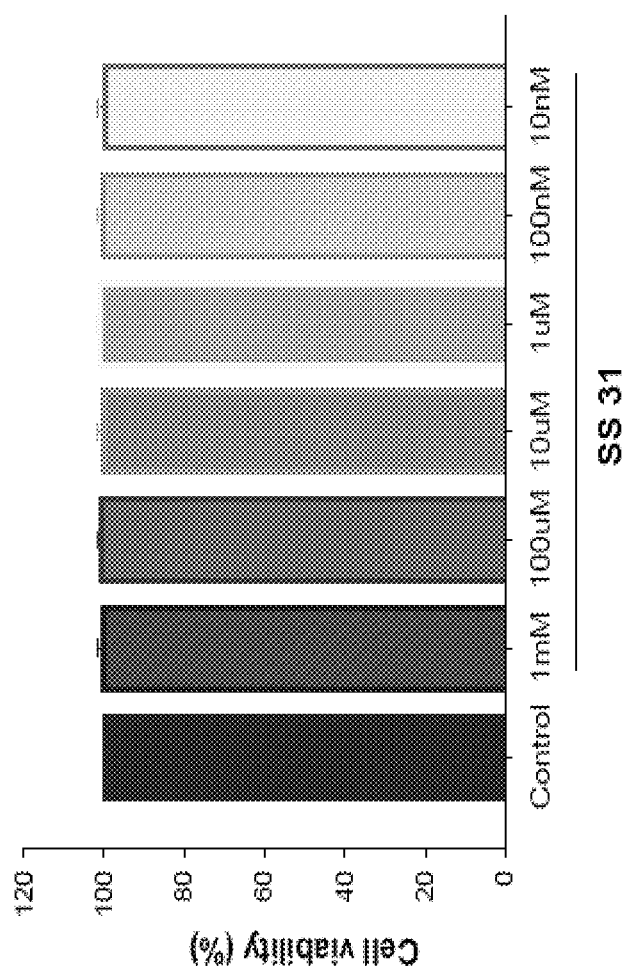
FIG. 22 is a chart showing that SS-31 had no effect on the viability of primary human retinal pigment epithelial (RPE) cells (as measured by the MTT assay).

Primary retinal pigment epithelial (RPE) cells were cultured to test the effects of the aromatic-cationic peptides of the invention in preventing or reducing oxidative damage in these cells. Methods useful for the study of primary retinal pigment epithelial cells have been described. See, Dunn et al., ARPE-19, A Human Retinal Pigment Epithelial Cell Line with Differentiated Properties, *Experimental Eye Research*, 1996, 62(2): 155-170. First, it was shown that SS-31 did not adversely effect these cells. Primary cultured human RPE cells were incubated with different concentrations of SS-31 alone for a period of 24 h, and cell viability was determined by a MTT assay (FIG. 22).

Figure 23:
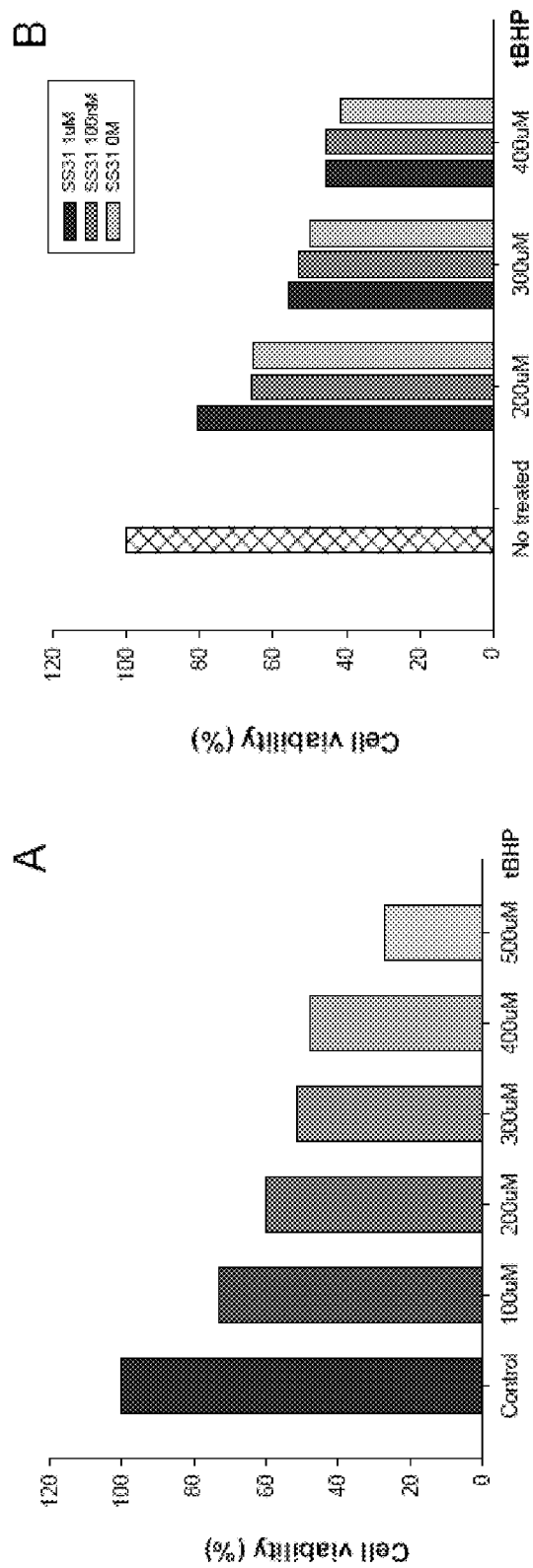
FIG. 23A is a chart showing the effect of different concentrations of tBHP on the viability (as measured by an MTT assay) of RPE cells.
FIG. 23B is a chart showing the effects of different concentrations of SS-31 on cell viability when exposed to increasing concentrations of tBHP.
Figure 31:
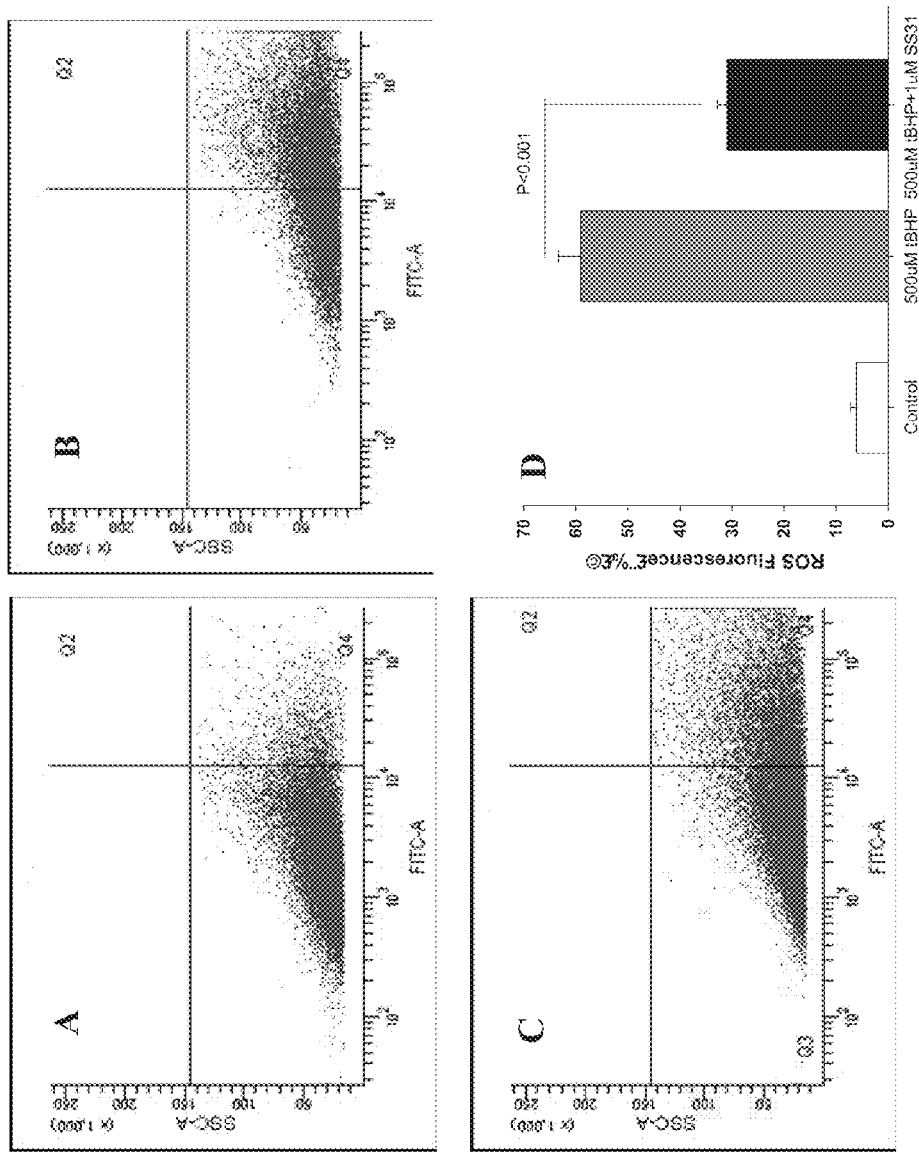
FIG. 31 is a series of graphs showing fluorescence intensity of intracellular ROS production in three groups of RPE cells using FACS analysis.
Figure 32:
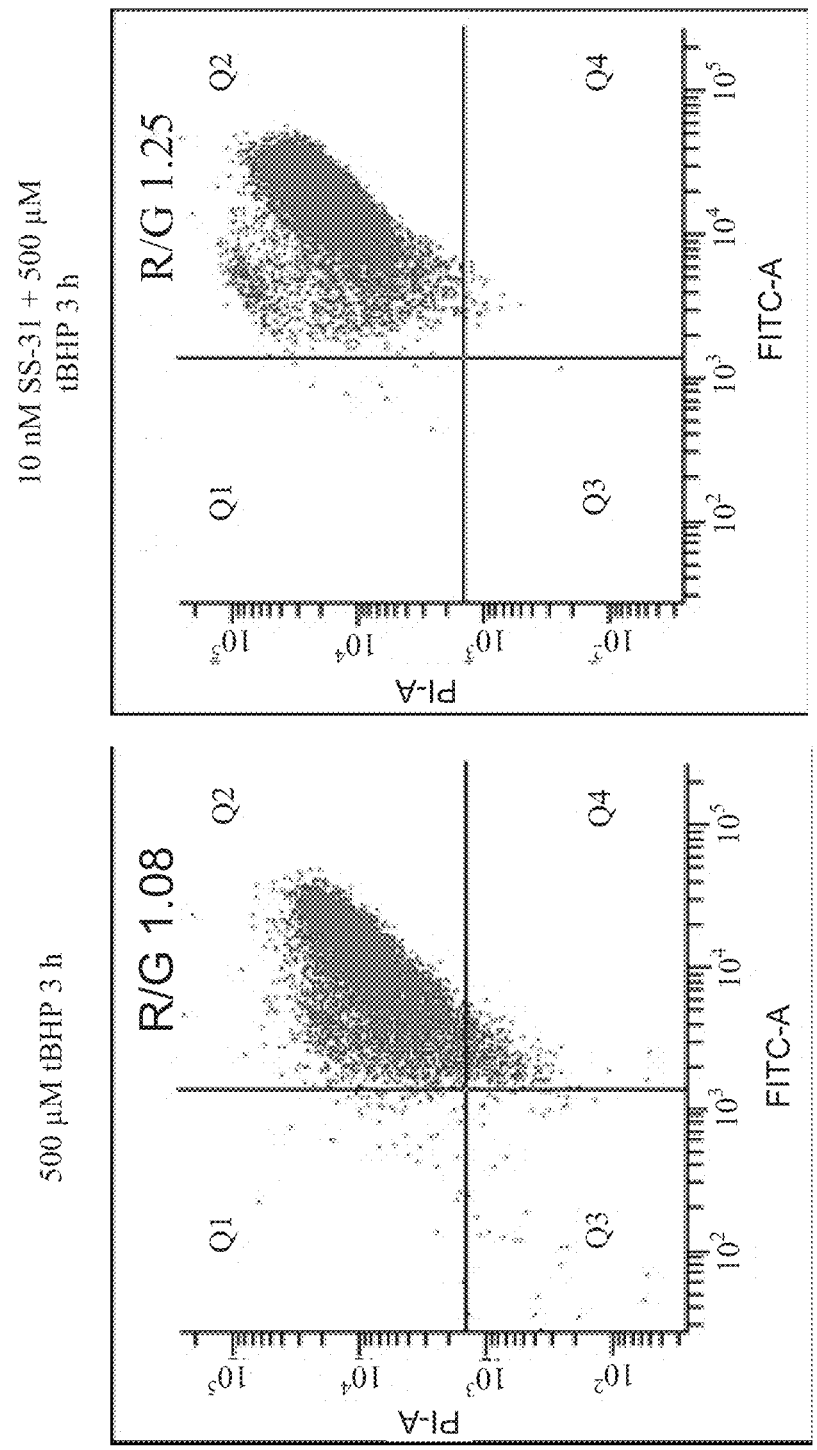
FIG. 32 is a series of graphs showing analysis of MMP labeled by JC-1 in a FACS assay. Three different concentration of SS-31 groups were analyzed.
Figure 32:
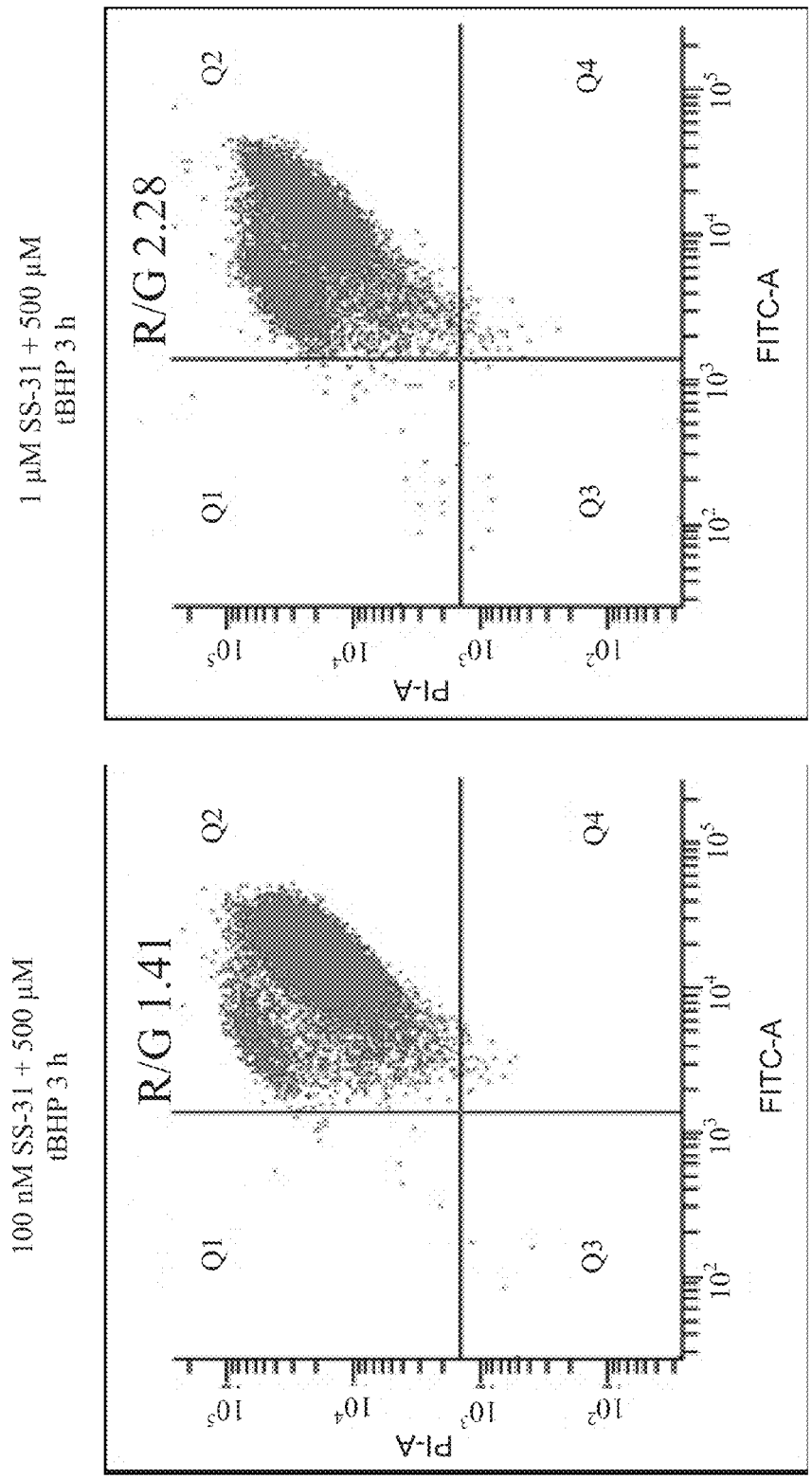
Figure 33:
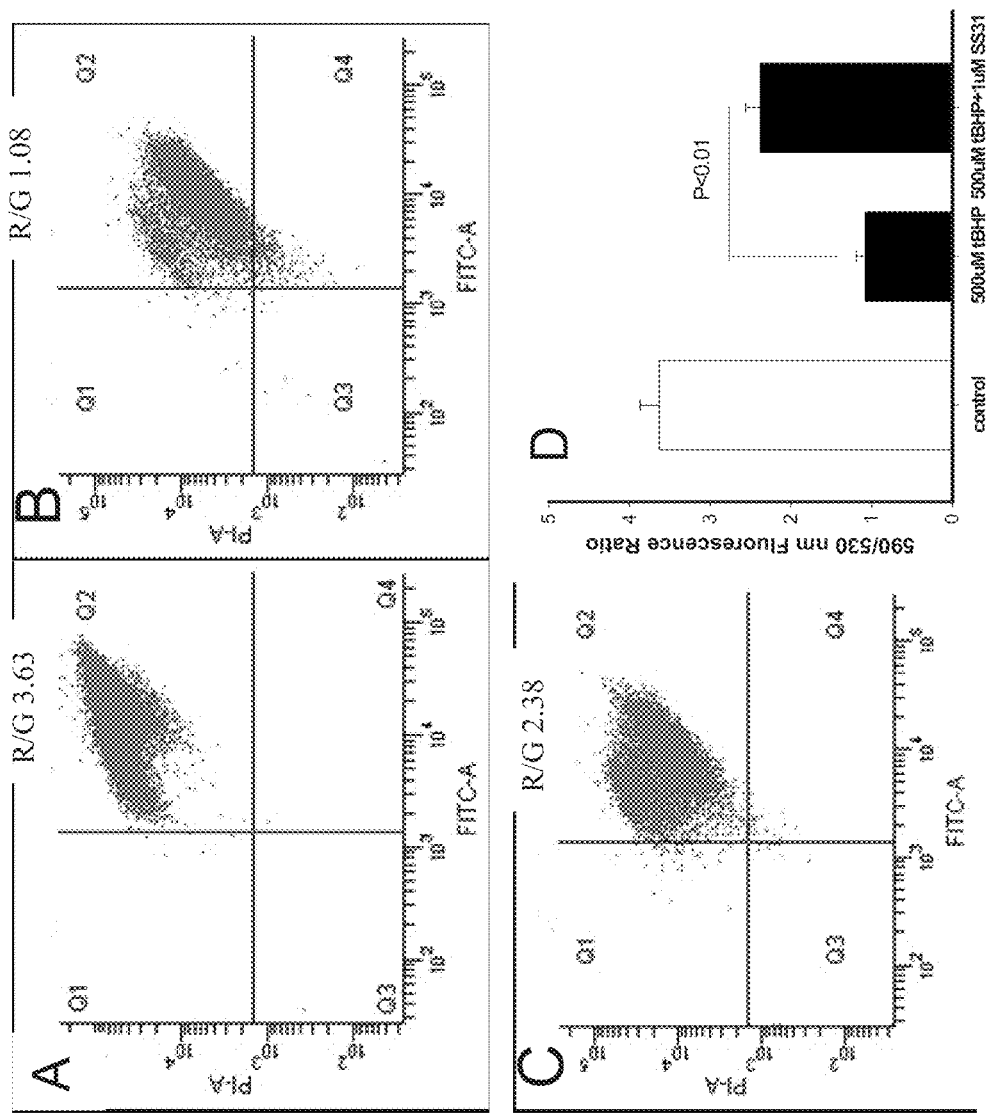
FIGS. 33A-33C is a series of graphs showing the effect of 1 $\mu M$ SS-31 on MMP decline induced by tBHP.
FIG. 33D is a chart comparing the fluorescence ratio for the different groups. *$P<0.01$, C vs. B.

Next, the viability of primary RPE cells was tested in the presence of tBHP and various concentrations of SS-31. Cells were plated at 10,000 cells per well in a 96-well plate and cultured for 24 h, then starved for 24 h. After that, cells were exposed to increasing concentrations of tBHP (FIG. 23A), or preincubated for 4 h with different concentrations of SS-31, then stimulated with tBHP for 6 h (FIG. 23B). These results indicate that SS-31 enhanced cell viability in response to tBHP administration. Intracellular ROS production in three groups of RPE cells was also examined using FACS analysis. FIG. 31A shows ROS production in control RPE cells; FIG. 31B shows ROS production in RPE cells treated with 500 μM tBHP for 3 h; and FIG. 31C shows ROS production in RPE cells treated with 500 μM tBHP for 3 h and 1 μM SS-31. FIG. 32 shows MMP labeled by JC-1 in a FACS analysis. Three different concentration of SS-31 groups were analyzed. The ratio of red to green in 500 μM tBHP for the 3 h group is 1.08, the ratio of red to green in 10 nM SS-31 for 4 h+500 μM tBHP for 3 h group is 1.25; the ratio of red to green in 100 nM SS-31 for 4 hr+500 μM tBHP for 3 h group is 1.4; and the ratio of red to green in 1 μM SS-31 for 4 h+500 μM tBHP for 3 h group is 2.28. FIG. 33 shows the effect of 1 μM SS-31 on MMP decline induced by tBHP. FIG. 33A: Control group, R/G is 3.63±0.24; FIG. 33B: 500 μM tBHP for 3 h group, R/G is 1.08±0.11; FIG. 33C: 1 μM SS-31 for 4 h+500 μM tBHP for 3 h group, R/G is 2.38±0.18. FIG. 33D is a chart comparing the fluorescence ratio for the different groups. *P<0.01, C vs. B.

Figure 34:
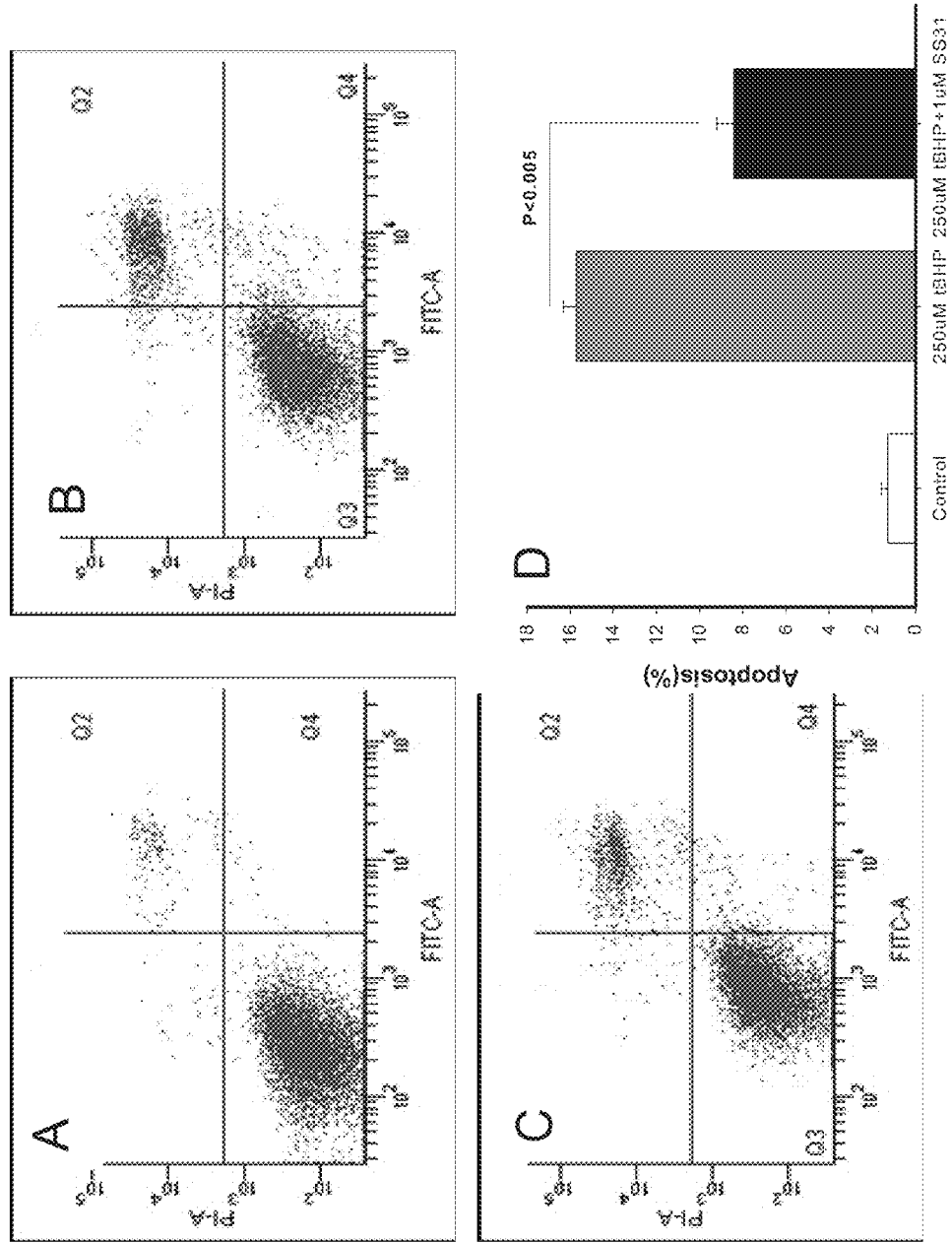
FIGS. 34A-34C is a series of graphs showing the effect of SS-31 on cell apoptosis induced by 250 $\mu M$ tBHP for 24 h.
FIG. 34D is a chart comparing the fluorescence ratio for the different groups. *$P<0.05$ C vs. B.
Figure 35:
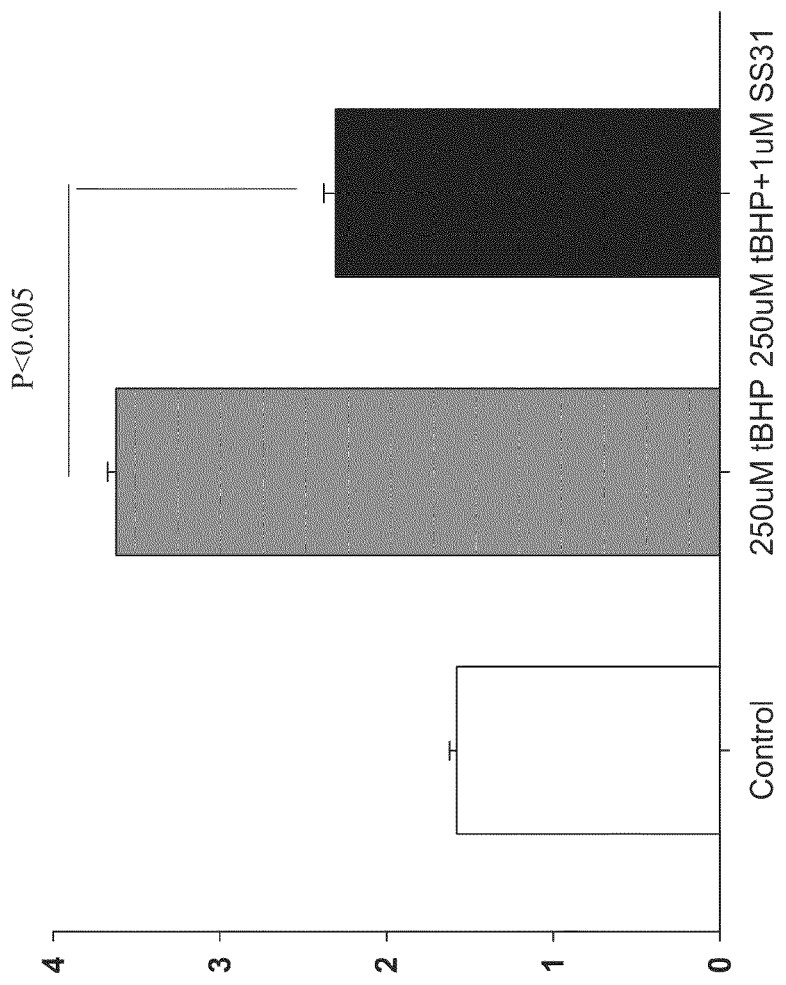
FIG. 35 is a chart showing the MDA level induced by tBHP in 3 groups of RPE cells. *$P<0.05$, 1 $\mu M$ SS-31 for 4 h+250 $\mu M$ tBHP for 24 h group vs 250 $\mu M$ tBHP for 24 h.

FIG. 34 shows the effect of SS-31 on cell apoptosis induced by 250 μM tBHP for 24 h. FIG. 34A: control group; (Q2+Q4) %=1.27±0.3%; FIG. 34B: 250 μM tBHP for 24 h group; (Q2+Q4) %=15.7±0.6%; FIG. 34C: 1 μM SS-31 for 4 h+250 μM tBHP for 24 h group; (Q2+Q4) %=8.4±0.8%. FIG. 34D is a chart comparing the fluorescence ratio for the different groups. *P<0.05 C vs. B. FIG. 35 is a chart showing the MDA level induced by tBHP in 3 groups of RPE cells. (*P<0.05).

Collectively, these results demonstrate that SS-31 prevents oxidative stress in primary retinal pigment epithelial cells. As such, the aromatic-cationic peptides of the present invention are useful in methods of preventing or treating damage to retinal cells in human subjects.

Example 5

Figure 24:
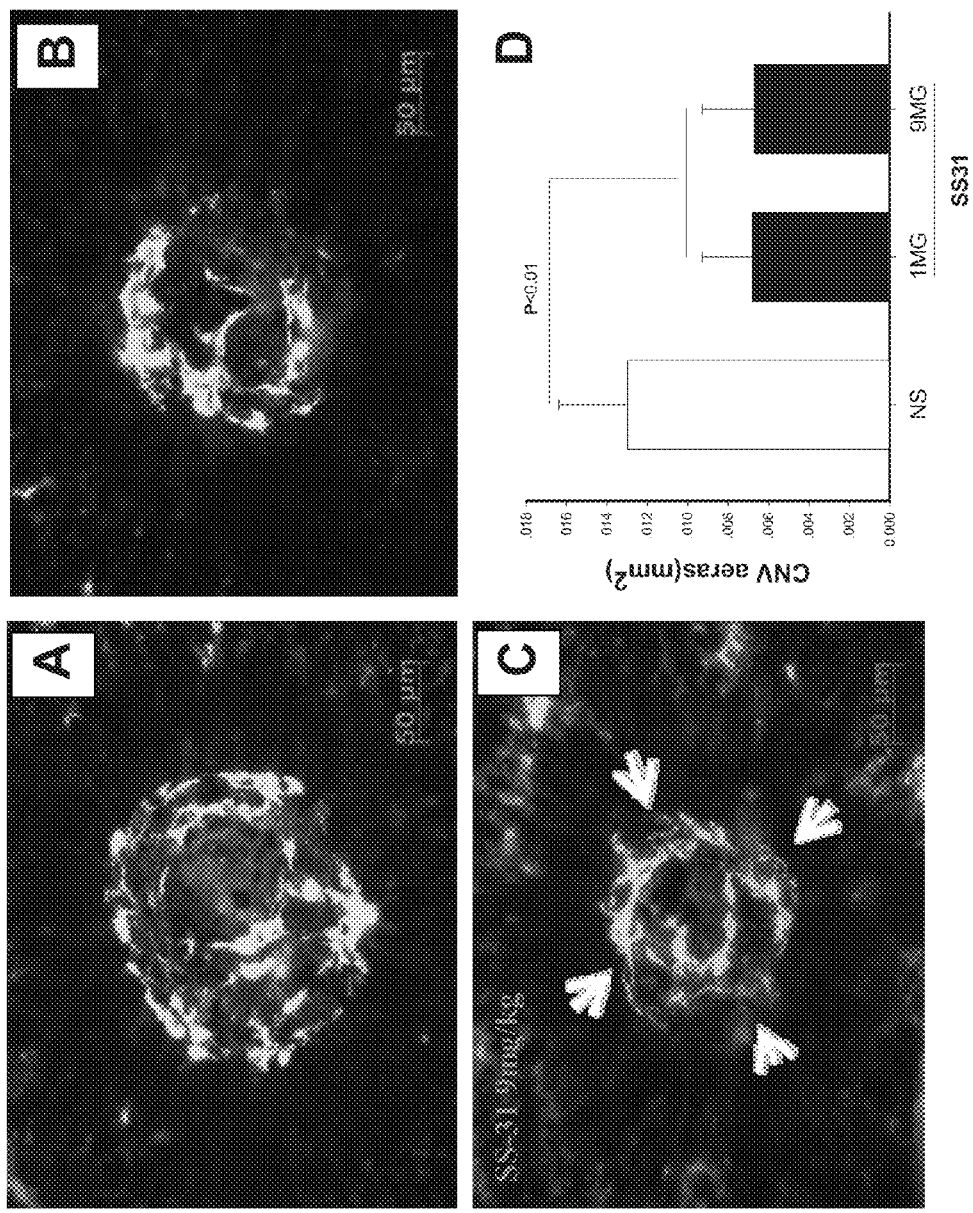
FIG. 24A-24C is a series of micrographs illustrating the pathological effects in a choroidal neovascularization (CNV) mouse model.
FIG. 24D is a graph showing CNV area in treated and control groups.

Prevention and Treatment of Choroidal Neovascularization by Aromatic-Cationic Peptides of the Invention in a CNV Mouse Model To further demonstrate the prevention of choroidal neovascularization (CNV) on the one hand, and treatment of CNV on the other hand, the aromatic-cationic peptides of the invention were tested on a mouse model of CNV (FIG. 24). CNV were induced in the eye with laser burns. Methods useful in the present studies have been described by Reich, *Mol Vis* 2003; 9:210-216.

Briefly, five to six-week-old C57BL/6 male mice were anesthetized with chloral hydrate and the pupils were dilated with tropicamide. With a coverslip used as a contact lens, four laser spots (532 nm, 260 mw, 0.01 s, 50 μm; Novus Spectra, Lumenis, USA) were applied to the fundus in a circle around the optic disc in the right eye. Daily intraperitoneal injections of 1 mg/kg, 9 mg/kg SS-31 or vehicle were started the day prior to laser photocoagulation.

After one week, mice were deeply anaesthetized and perfused through the left ventricle with 1 ml (50 mg/ml) of PBS-buffered fluorescein-dextran. Eyes were enucleated and fixed in 4% paraformaldehyde for 2 h. The eyes were sectioned at the equator, and the anterior half and retina were removed. The posterior eye segment containing the sclera and choroid was dissected into quarters by four to five radial cuts and mounted on a slide. All flatmounts were examined by a fluorescence microscope (AxioCam MRC; Carl Zeiss). Image-Pro Plus software (Media Cybernetics, Silver Spring, Md.) was used to measure the area of each CNV lesion.

There were 48 locations of neovascularization in each group. The area of neovascularization was calculated using IMAGE-PROPLUS6.0 software. The area of neovascularization in the CNV model, 1 mg/kg SS-31 and 9 mg/kg SS-31 groups were 0.0130±0.0034, 0.0068±0.0025, 0.0067±0, respectively. These results indicate that the two concentrations of SS-31 significantly reduced the area of choroidal neovasculatization (P<0.05) (FIG. 24).

Example 6

Figure 25:
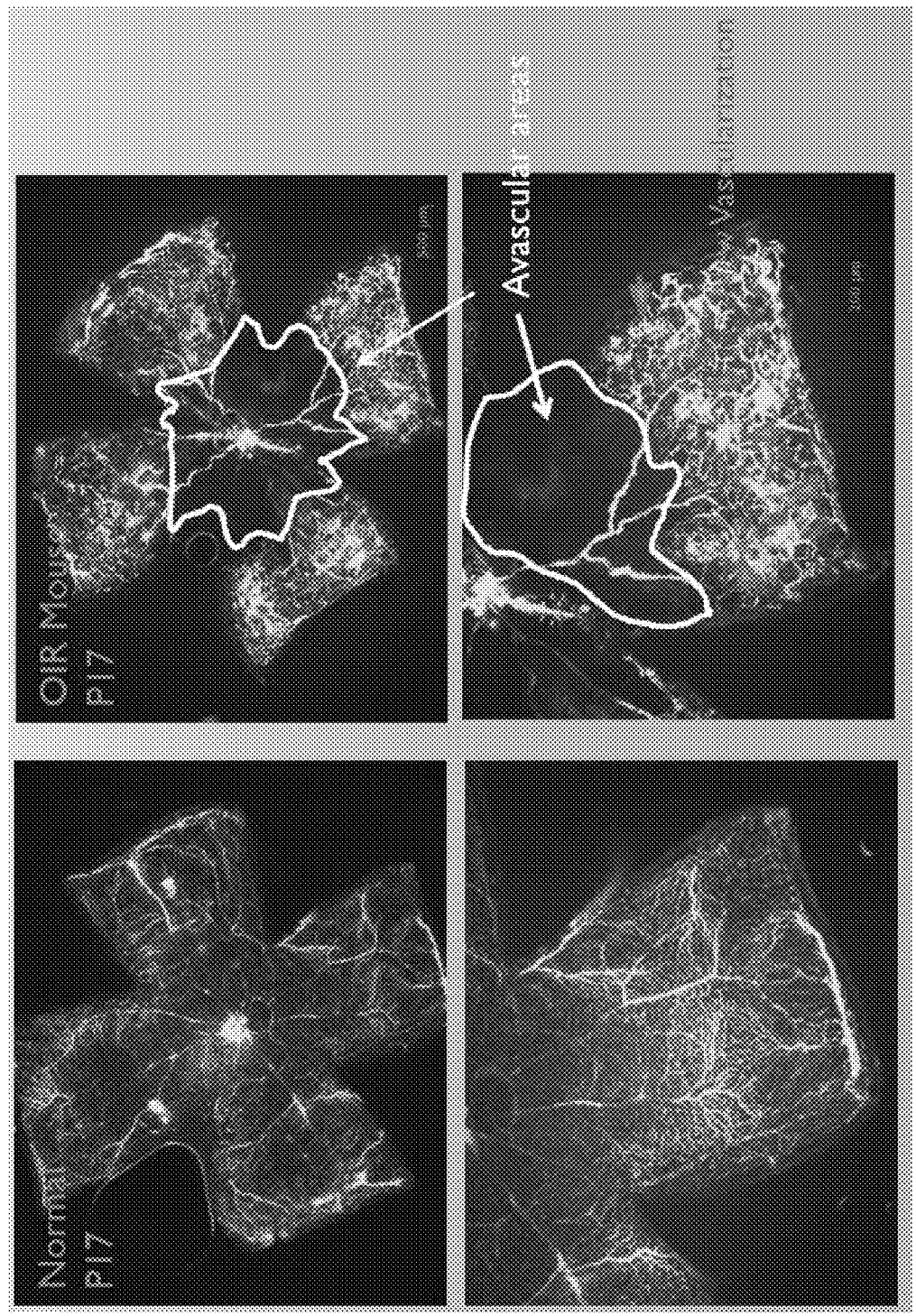
FIG. 25 is a series of micrographs illustrating different pathological findings in an oxygen-induced retinopathy (OIR) mouse model. Note areas of avascularity and new vascularization in a P17 OIR mouse as compared to a P17 normal mouse.

Prevention and Treatment of Oxygen-Induced Retinopathy (OIR) by Aromatic-Cationic Peptides of the Invention in an OIR Mouse Model To further demonstrate the prevention of oxygen-induced retinopathy (OIR), the aromatic-cationic peptides of the invention were tested on a mouse model of OIR (FIG. 25). In this model, 7-day-old mouse pups with partially developed retinal vasculature were subjected to hyperoxia (75% oxygen) for 5 days, which stops retinal vessel growth and causes significant vaso-obliteration. On postnatal day 12, the pups were returned to room air, and by postnatal day 17, a florid compensatory retinal neovascularization occurred. This model of pathological neovascularization has been widely used as a substitute for proliferative diabetic retinopathy (DR).

Figure 26:
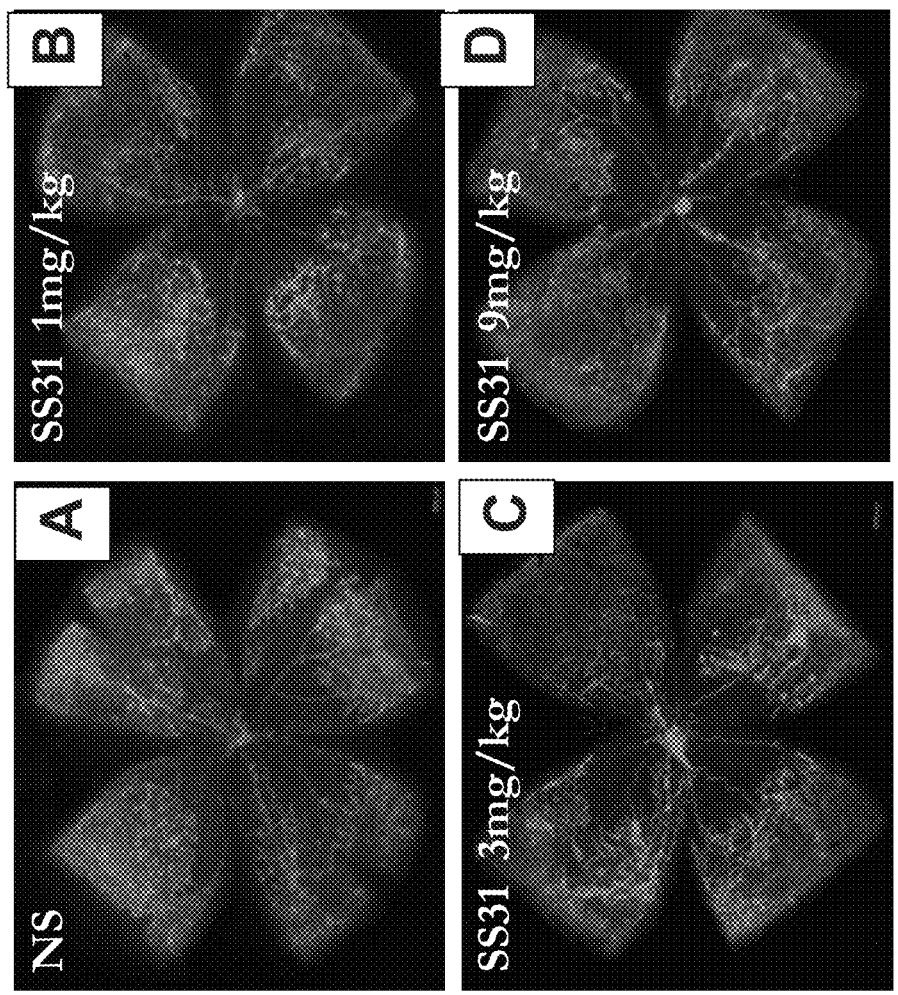
FIG. 26A-26D is a series of micrographs showing the effects of administering SS-31 in the OIR mouse model.
FIG. 26E is a graph showing the neovascular area of the control and treated groups. SS-31 reduced the avascular area.
Figure 26:
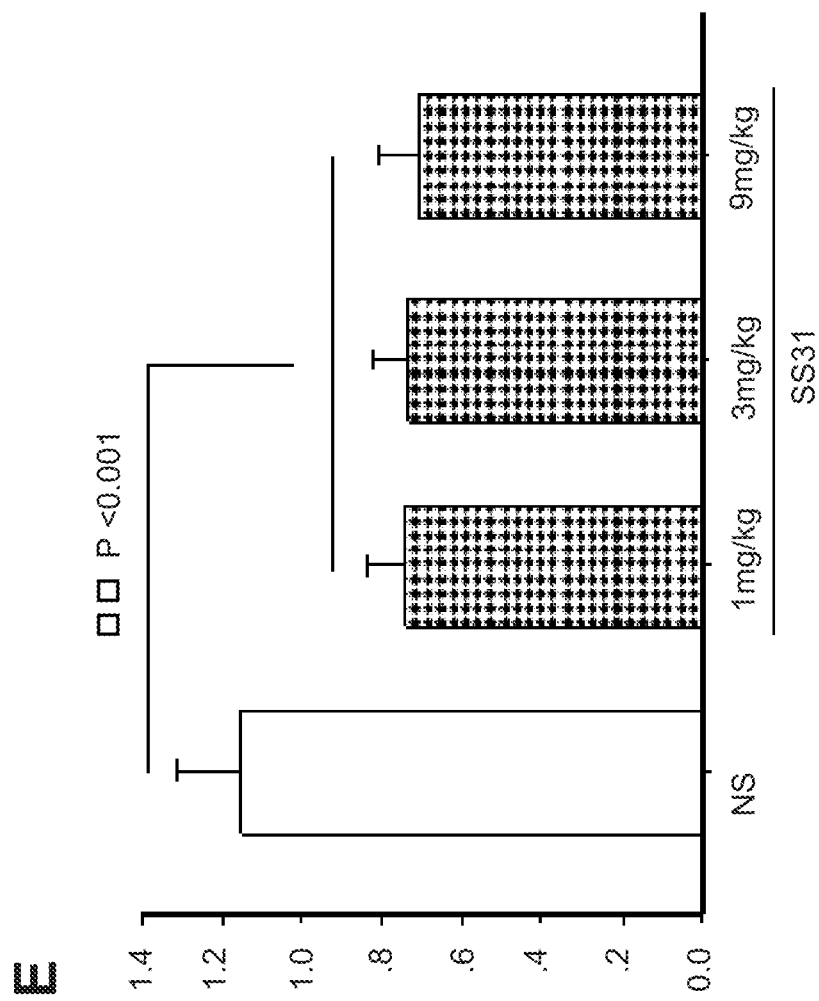

To examine the effects of the aromatic-cationic peptides of the invention on prevention of OIR, OIR was induced in mouse pups and the mice were simultaneously administered an aromatic-cationic peptide (e.g., SS-20 or SS-31) for approximately 6 weeks. The results are shown in FIG. 26 and indicate that treatment with SS-31 prevented the compensatory retinal neovascularization. As such, the aromatic-cationic peptides of the invention are useful in methods of preventing proliferative diabetic retinopathy in mammalian subjects.

Example 7

Antioxidants Reduce Photoreceptor Cell Death in a Model of Retinitis Pigmentosa

A cone cell specific line 661W was derived from a mouse retinal tumor. Methods useful in the present studies of 661W cells have been described previously. See generally, Gearóid Tuohy, Sophia Millington-Ward, Paul F. Kenna, Peter Humphries and G. Jane Farrar, Sensitivity of Photoreceptor-Derived Cell Line (661W) to Baculoviral p35, Z-VAD.FMK, and Fas-Associated Death Domain, *Investigative Ophthalmology and Visual Science*. 2002; 43:3583-3589. These cells were cultured to test the effects of the aromatic-cationic peptides of the invention in preventing or reducing oxidative damage in the cone cells (FIG. 27). First, it was shown that tBHP affected survival of 661W cells (FIG. 27A). Different doses of tBHP were administered to the cells for 3 h. Next, it was shown that different doses of SS-31 reduced tBHP-induced 661W cell death (FIG. 27B).

Figure 30:
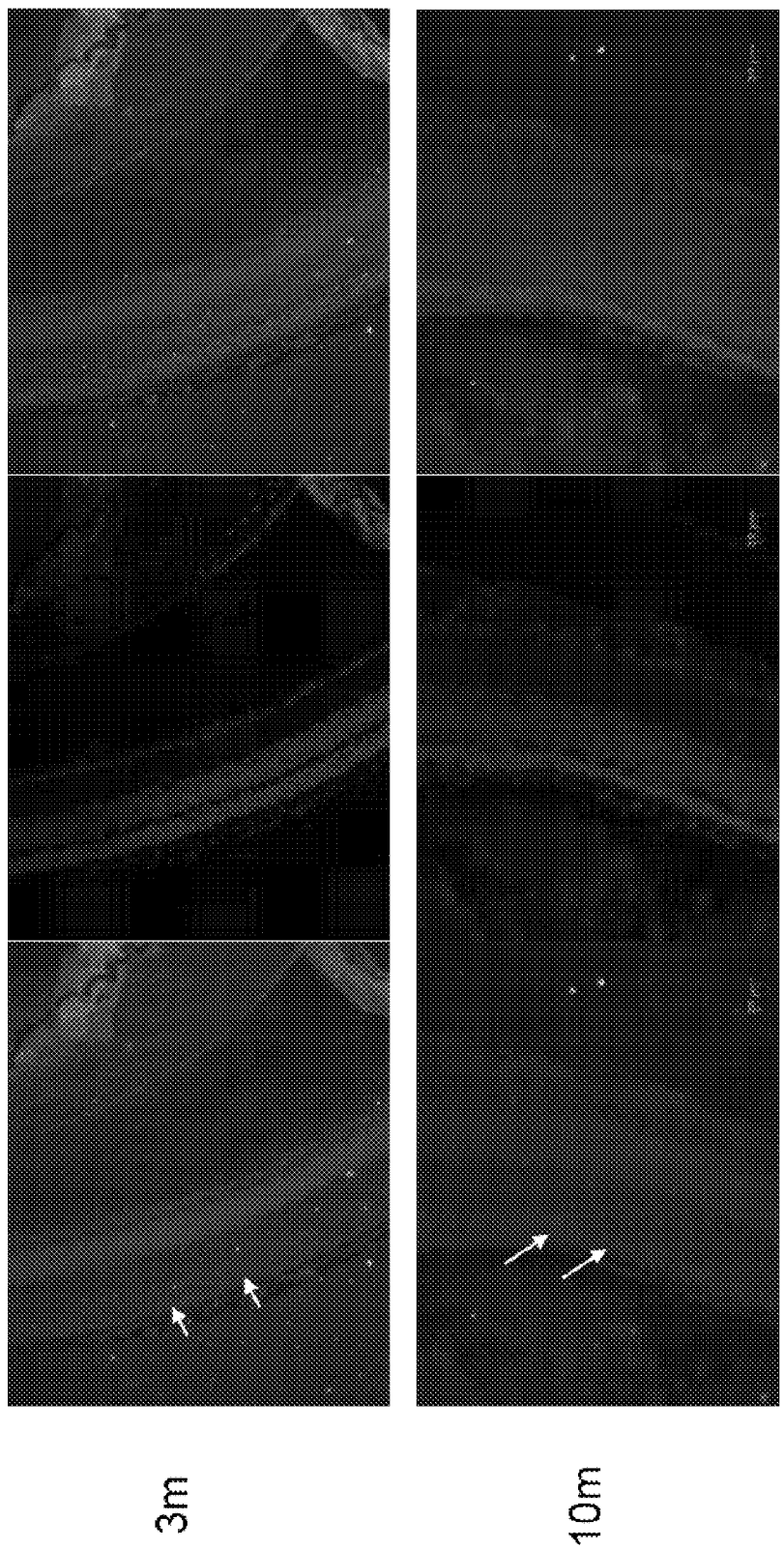
FIG. 30 is a series of micrographs showing staining for acolein, a marker for oxidative lipid damage in a mouse model of retina degeneration.

The potential of SS-31 to protect against loss of mitochondrial viability induced by tBHP, 100 nmol/L SS-31 was administered to the cultures of 661w cells. The results are shown in FIG. 30 and indicate that SS-31 significantly enhanced mitochondrial viability compared to cells not administered SS-31, as shown by a JC-1 assay.

Example 8

Effects of SS-31 in a Mouse Model of Retina Degeneration

To further demonstrate the prevention of retinal degeneration, the aromatic-cationic peptides of the invention were tested on a mouse model of retina degeneration. CNV is induced in the eye with laser burns. (see Example 5). Mouse models of retinal degeneration have been investigated for many years in the hope of understanding the causes of photoreceptor cell death. Naturally occurring mouse mutants that manifest degeneration of photoreceptors in the retina with preservation of all other retinal cell types have been found: retinal degeneration (formerly rd, identical with rodless retina, r, now Pde6b rd1); Purkinje cell degeneration (pod); nervous (nr); retinal degeneration slow (rds, now Prph Rd2); retinal degeneration 3 (rd3); motor neuron degeneration (mnd); retinal degeneration 4 (Rd4); retinal degeneration 5 (rd5); vitiligo (vit, now Mitf mi-vit); retinal degeneration 6 (rd6); retinal degeneration 7 (rd7); neuronal ceroid lipofuscinosis (nclf); retinal degeneration 8 (rd8); retinal degeneration 9 (Rd9); retinal degeneration 10 (rd10); and cone photoreceptor function loss (cpfl1).

Figure 28:
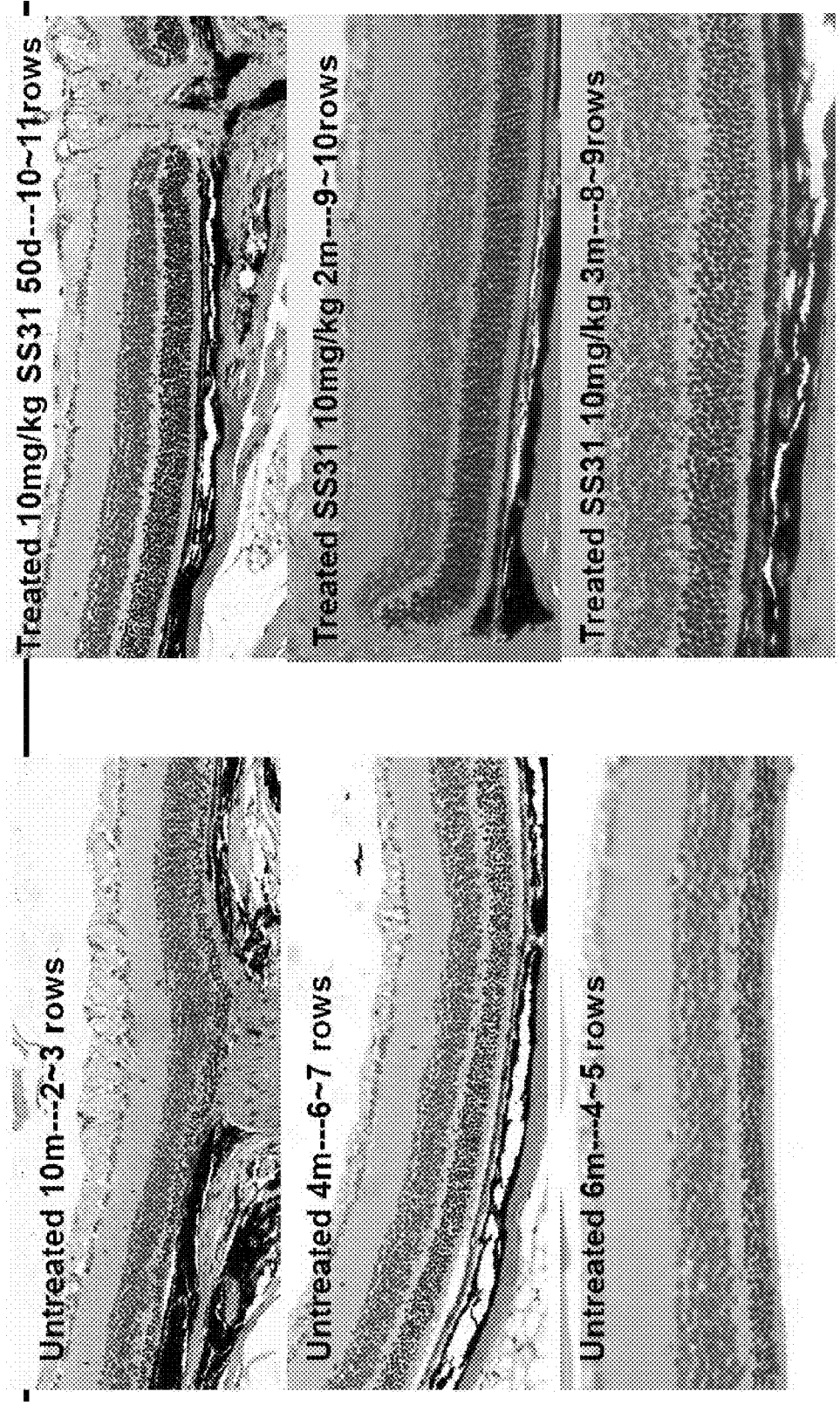
FIG. 28 is a series of micrographs showing the thickness of the retinal outer nuclear layer (ONL) in a mouse model of retina degeneration in control and SS-31-treated mice.
Figure 29:
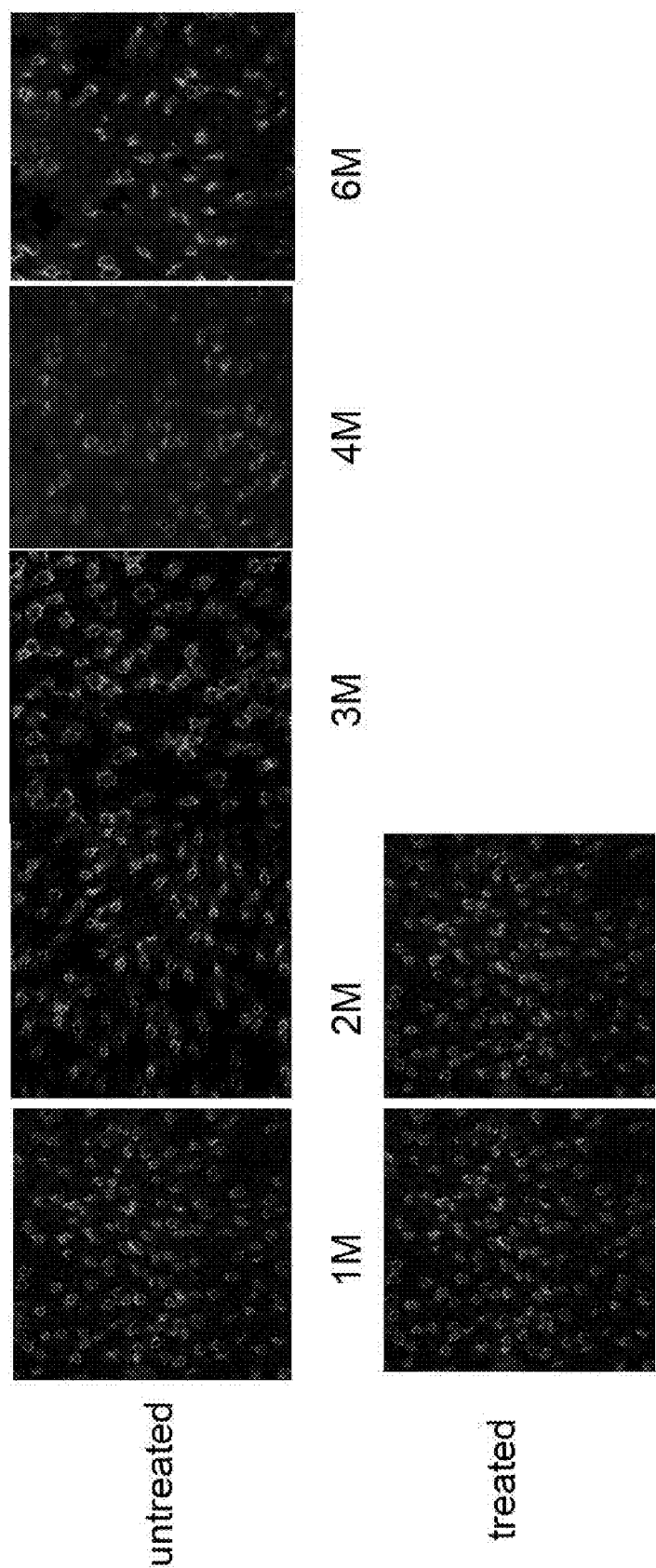
FIG. 29 is a series of micrographs showing the cone cell density in retinal flat mounts stained with peanut agglutinin (PNA), which selectively stains cone inner and outer segments in control and SS-31-treated mice.

FIG. 28 is a series of micrographs showing the thickness of the retinal outer nuclear layer (ONL) in a mouse model of retina degeneration in control and SS-31-treated mice. The results indicate that SS-31 treated mice retained a greater number of rows of cells in the ONL compared to untreated mice. Retinal flat mounts stained with peanut agglutinin (PNA), which selectively stain core inner and outer segments also show that cone cell density is greater in SS-31 treated mice (FIG. 29). These results indicate that treatment with SS-31 prevented the compensatory damage to the retinal outer nuclear layer in a mouse model of retinal degeneration. As such, the aromatic-cationic peptides of the invention are useful in methods of preventing retinal degeneration in mammalian subjects.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for treating an ophthalmic condition in a mammalian subject in need thereof, comprising administering to the subject a therapeutically effective amount of a peptide represented by the formula D-Arg-2'6'-Dmt-Lys-Phe-NH$_2$ or Phe-D-Arg-Phe-Lys-NH$_2$, and further comprising separately, sequentially, or simultaneously administering a second active agent, wherein the second active agent is selected from the group consisting of vitamin A, vitamin C, vitamin E, lycopene, selenium, α-lipoic acid, coenzyme Q, glutathione, a carotenoid, aceclidine, acetazolamide, anecortave, apraclonidine, atropine, azapentacene, azelastine, bacitracin, befunolol, betamethasone, betaxolol, bimatoprost, brimonidine, brinzolamide, carbachol, carteolol, celecoxib, chloramphenicol, chlortetracycline, ciprofloxacin, cromoglycate, cromolyn, cyclopentolate, cyclosporin, dapiprazole, demecarium, dexamethasone, diclofenac, dichlorphenamide, dipivefrin, dorzolamide, echothiophate, emedastine, epinastine, epinephrine, erythromycin, ethoxzolamide, eucatropine, fludrocortisone, fluorometholone, flurbiprofen, fomivirsen, framycetin, ganciclovir, gatifloxacin, gentamycin, homatropine, hydrocortisone, idoxuridine, indomethacin, isoflurophate, ketorolac, ketotifen, latanoprost, levobetaxolol, levobunolol, levocabastine, levofloxacin, lodoxamide, loteprednol, medrysone, methazolamide, metipranolol, moxifloxacin, naphazoline, natamycin, nedocromil, neomycin, norfloxacin, ofloxacin, olopatadine, oxymetazoline, pemirolast, pegaptanib, phenylephrine, physostigmine, pilocarpine, pindolol, pirenoxine, polymyxin B, prednisolone, proparacaine, ranibizumab, rimexolone, scopolamine, sezolamide, squalamine, sulfacetamide, suprofen, tetracaine, tetracyclin, tetrahydrozoline, tetryzoline, timolol, tobramycin, travoprost, triamcinulone, trifluoromethazolamide, trifluridine, trimethoprim, tropicamide, unoprostone, vidarabine, xylometazoline, pharmaceutically acceptable salts thereof, and combinations thereof.

2. The method of claim 1, wherein the ophthalmic condition is selected from the group consisting of: cataracts, retinitis pigmentosa, glaucoma, choroidal neovascularization, retinal degeneration, and oxygen-induced retinopathy.

3. The method of claim 1, wherein the peptide is D-Arg-2'6'-Dmt-Lys-Phe-NH$_2$.

4. The method of claim 1, wherein the peptide is Phe-D-Arg-Phe-Lys-NH$_2$.

5. The method of claim 1, wherein the subject is a human.

6. The method of claim 1, wherein the peptide is administered intraocularly, iontophoretically, orally, topically, systemically, intravenously, subcutaneously, or intramuscularly.

* * * * *